United States Patent
Nakata et al.

(10) Patent No.: US 11,350,849 B2
(45) Date of Patent: Jun. 7, 2022

(54) SYSTEMS AND METHODS FOR NON-CONTACT MULTIPARAMETER VITAL SIGNS MONITORING, APNEA THERAPY, APNEA DIAGNOSIS, AND SNORE THERAPY

(71) Applicant: RESMED SENSOR TECHNOLOGIES LIMITED, Clonskeagh (IE)

(72) Inventors: Robert Haruo Nakata, Honolulu, HI (US); Isar Mostafanezhad, Honolulu, HI (US); Scott Tadashi Miyasato, Mililani, HI (US); Erik Vossman, Honolulu, HI (US)

(73) Assignee: ResMed Sensor Technologies Limited

( * ) Notice: Subject to any disclaimer, the term of this patent is extended or adjusted under 35 U.S.C. 154(b) by 832 days.

(21) Appl. No.: 16/110,974

(22) Filed: Aug. 23, 2018

(65) Prior Publication Data

US 2019/0159960 A1    May 30, 2019

Related U.S. Application Data

(63) Continuation of application No. 14/208,173, filed on Mar. 13, 2014, now abandoned, which is a
(Continued)

(51) Int. Cl.
*A61B 5/08* (2006.01)
*A61H 23/02* (2006.01)
(Continued)

(52) U.S. Cl.
CPC .......... *A61B 5/0816* (2013.01); *A61B 5/0036* (2018.08); *A61B 5/113* (2013.01);
(Continued)

(58) Field of Classification Search
CPC ....... A61B 5/08; A61B 5/1114; A61B 5/7203; A61B 5/1113; A61B 5/113; A61B 5/165;
(Continued)

(56) References Cited

U.S. PATENT DOCUMENTS

| | | |
|---|---|---|
| 4,715,367 A | 12/1987 | Crossley |
| 4,757,825 A | 7/1988 | Diamond |

(Continued)

FOREIGN PATENT DOCUMENTS

| | | |
|---|---|---|
| WO | 2011082346 A2 | 7/2011 |
| WO | 2016124739 A1 | 8/2016 |

OTHER PUBLICATIONS

A. Droitcour "Non-contact measurement of heart and respiration rates with single-chip microwave Doppler radar," PhD thesis, Stanford University, 2006. (Year: 2006).*
(Continued)

*Primary Examiner* — Eric J Messersmith
(74) *Attorney, Agent, or Firm* — Botos Churchill IP Law LLP

(57) ABSTRACT

Aspects of the of the disclosure relate to a non-contact physiological motion sensor and a monitor device that can incorporate use of the Doppler effect. A continuous wave of electromagnetic radiation can be transmitted toward one or more subjects and the Doppler-shifted received signals can be digitized and/or processed subsequently to extract information related to the cardiopulmonary motion in the one or more subjects. The extracted information can be used, for example, to determine apneic events and/or snoring events and/or to provide apnea or snoring therapy to subjects when used in conjunction with an apnea or snoring therapy device. In addition, methods of use are disclosed for sway cancellation, realization of cessation of breath, integration with multi-parameter patient monitoring systems, providing posi-
(Continued)

US 11,350,849 B2
Page 2 tive providing patient identification, or any combination thereof.

48 Claims, 52 Drawing Sheets

Related U.S. Application Data continuation of application No. PCT/US2012/055648, filed on Sep. 14, 2012, which is a continuation-in-part of application No. 13/298,248, filed on Nov. 16, 2011, now abandoned, which is a continuation-in-part of application No. 13/108,795, filed on May 16, 2011, now abandoned, which is a continuation-in-part of application No. PCT/US2011/036543, filed on May 13, 2011.

(60) Provisional application No. 61/535,943, filed on Sep. 16, 2011, provisional application No. 61/535,937, filed on Sep. 16, 2011, provisional application No. 61/370,457, filed on Aug. 4, 2010, provisional application No. 61/345,070, filed on May 15, 2010, provisional application No. 61/345,065, filed on May 14, 2010.

(51) Int. Cl.

| | |
|---|---|
| *A61B 5/00* | (2006.01) |
| *A61H 21/00* | (2006.01) |
| *A61N 1/36* | (2006.01) |
| *G01S 7/00* | (2006.01) |
| *G01S 13/50* | (2006.01) |
| *G01S 13/82* | (2006.01) |
| *G01S 13/87* | (2006.01) |
| *G01S 13/88* | (2006.01) |
| *A61B 5/113* | (2006.01) |
| *A61N 1/372* | (2006.01) |
| *A61B 5/0507* | (2021.01) |
| *A61B 5/085* | (2006.01) |
| *A61B 5/087* | (2006.01) |
| *A61B 5/11* | (2006.01) |
| *A61B 5/1455* | (2006.01) |
| *G01S 7/41* | (2006.01) |

(52) U.S. Cl.
CPC .......... *A61B 5/4818* (2013.01); *A61B 5/4836* (2013.01); *A61H 21/00* (2013.01); *A61H 23/02* (2013.01); *A61N 1/3601* (2013.01); *A61N 1/36031* (2017.08); *G01S 7/003* (2013.01); *G01S 13/50* (2013.01); *G01S 13/825* (2013.01); *G01S 13/87* (2013.01); *G01S 13/88* (2013.01); *A61B 5/0507* (2013.01); *A61B 5/085* (2013.01); *A61B 5/087* (2013.01); *A61B 5/112* (2013.01); *A61B 5/14551* (2013.01); *A61B 5/486* (2013.01); *A61B 5/6823* (2013.01); *A61B 5/6831* (2013.01); *A61B 5/7257* (2013.01); *A61N 1/37282* (2013.01); *G01S 7/41* (2013.01)

(58) Field of Classification Search
CPC ....... A61B 5/1118; A61B 5/05; A61B 5/7221; A61B 5/726; A61B 5/7207; A61B 5/7239; A61B 5/1102; A61B 2560/0204; A61B 5/7257; G01S 13/56; G01S 13/583; G01S 13/88

See application file for complete search history.

(56) References Cited

U.S. PATENT DOCUMENTS

| | | | |
|---|---|---|---|
| 5,329,931 | A | 7/1994 | Imran |
| 5,483,969 | A | 1/1996 | Testerman |
| 5,844,996 | A | 12/1998 | Enzmann |
| 5,961,447 | A | 10/1999 | Raviv |
| 6,062,216 | A | 5/2000 | Corn |
| 6,093,158 | A | 7/2000 | Morris |
| 6,314,324 | B1 | 11/2001 | Lattner |
| 6,587,725 | B1 | 7/2003 | Durand |
| 6,935,335 | B1 | 8/2005 | Lehrman |
| 2003/0199945 | A1 | 2/2003 | Ciulla |
| 2006/0145878 | A1 | 7/2006 | Lehrman |
| 2007/0150022 | A1 | 6/2007 | Ujhazy et al. |
| 2008/0074307 | A1 | 3/2008 | Boric-Lubecke |
| 2009/0078257 | A1 | 3/2009 | Bhat |
| 2010/0131029 | A1 | 5/2010 | Durand |
| 2010/0152600 | A1* | 6/2010 | Droitcour ............. A61B 5/1114 600/534 |
| 2010/0198083 | A1* | 8/2010 | Lin ......................... G06F 17/14 600/484 |
| 2010/0217345 | A1 | 8/2010 | Wolfe |
| 2011/0218684 | A1 | 9/2011 | Genaro |
| 2012/0192874 | A1 | 8/2012 | Bolea |

OTHER PUBLICATIONS

First Examination Report issued in corresponding Indian application No. 7077/DELNP/2010 dated Feb. 16, 2018.

Jordon et al., "Treating Obstructive Sleep Apnea With Hypoglossal Nerve Stimulation", pp. 1479-1481, published Jul. 2011.

Steier, John , et al., Steier, et al., Continuous Transcutaneous Submental Electrical Stimulation in Obstructive Sleep Apnea : A Feasibility Study, www.chestjournal.chestpubs.org by Holger Woehrle, Oct. 5, 2011.

EP Office Action dated Sep. 22, 2021 for EP Application No. 12832297.1.

\* cited by examiner

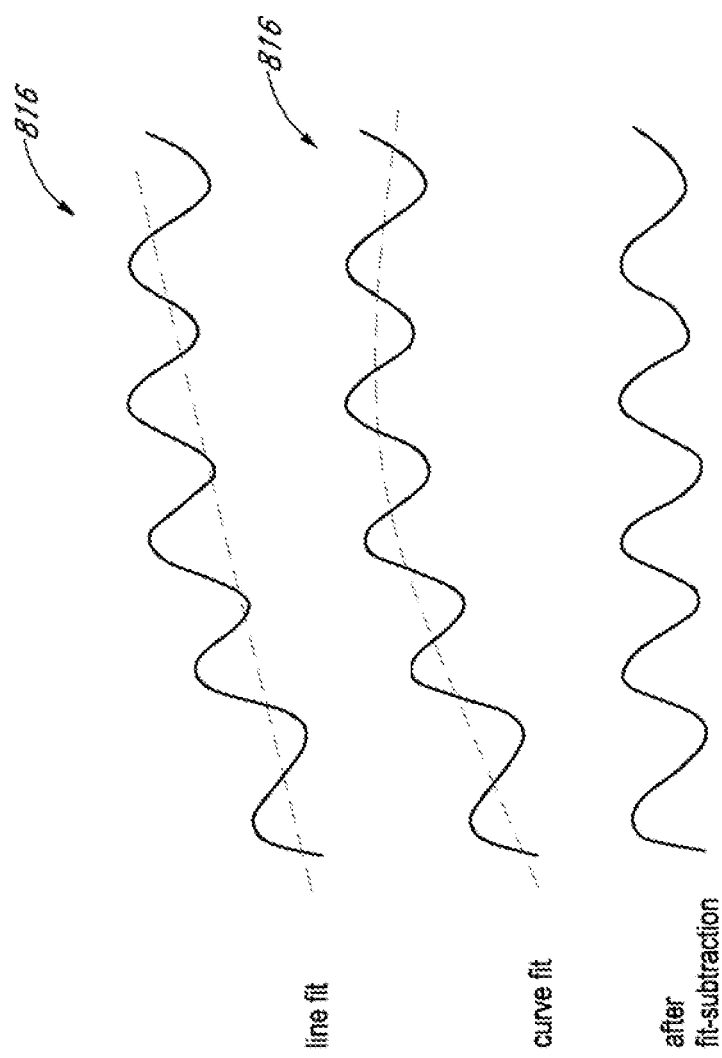

Flowchart (B)

Flowchart (D)

TOP VIEW

FRONT VIEW

SIDE VIEW

BOTTOM VIEW

SYSTEMS AND METHODS FOR NON-CONTACT MULTIPARAMETER VITAL SIGNS MONITORING, APNEA THERAPY, APNEA DIAGNOSIS, AND SNORE THERAPY

CROSS-REFERENCE TO RELATED APPLICATIONS

This application is a continuation of U.S. application Ser. No. 14/208,173, filed on Mar. 13, 2014, which is a continuation of International Application No. PCT/US2012/055648 filed on Sep. 14, 2012, which is a continuation-in-part application of U.S. application Ser. No. 13/298,248 filed on Nov. 16, 2011, which is a continuation-in-part application of U.S. patent application Ser. No. 13/108,795 filed on May 16, 2011, which claims priority to U.S. Provisional Application No. 61/345,065 filed on May 14, 2010; U.S. Provisional Application No. 61/345,070, filed on May 15, 2010; U.S. Provisional Application No. 61/370,457 filed on Aug. 4, 2010; and U.S. patent application Ser. No. 13/108,795 also claims the benefit of priority of International Application No. PCT/US2011/36543 filed on May 13, 2011 and U.S. patent application Ser. No. 13/298,248 filed on Nov. 16, 2011 which claims priority to U.S. Provisional Application No. 61/535,937 filed on Sep. 16, 2011 and U.S. Provisional Application No. 61/535,943 filed on Sep. 16, 2011, each of the disclosures of the foregoing applications are hereby incorporated herein by reference.

This application is also a continuation of International Application No. PCT/US2012/055648, filed on Sep. 14, 2012 which also claims the benefit under 35 U.S.C. § 119(e) as a nonprovisional application of U.S. Provisional Application No. 61/535,937 filed on Sep. 16, 2011 and U.S. Provisional Application No. 61/535,943 filed on Sep. 16, 2011. Each of the foregoing priority applications is incorporated herein by reference in its entirety.

This application also incorporates by reference in their entireties all of the following: U.S. application Ser. No. 12/575,447, filed on Oct. 7, 2009, titled "Non-Contact Physiologic Motion Sensors and Methods For Use;" U.S. application Ser. No. 12/418,518, filed on Apr. 3, 2009, titled "Non-Contact Physiologic Motion Sensors and Methods For Use;" U.S. Provisional Application No. 61/072,983, filed on Apr. 3, 2008, titled "Doppler Radar System for Local and Remote Respiration Signals Monitoring"; U.S. Provisional Application No. 61/072,982, filed on Apr. 3, 2008, titled "Method for Detection of Cessation of Breathing"; U.S. Provisional Application No. 61/123,017, filed on Apr. 3, 2008, titled "Method for Detection of Motion Interfering with Respiration"; U.S. Provisional Application No. 61/123,135, filed on Apr. 3, 2008, titled "Method for Detection of Presence of Subject"; U.S. Provisional Application No. 61/125,021, filed on Apr. 21, 2008, titled "Non-contact Spirometry with a Doppler Radar"; U.S. Provisional Application No. 61/125,019, filed on Apr. 21, 2008, titled "Monitoring Physical Activity with a Physiologic Monitor"; U.S. Provisional Application No. 61/125,018, filed on Apr. 21, 2008, titled "Non-contact Method for Calibrating Tidal Volume Measured with Displacement Sensors"; U.S. Provisional Application No. 61/125,023, filed on Apr. 21, 2008, titled "Use of Empirical Mode Decomposition to Extract Physiological Signals from Motion Measured with a Doppler Radar"; U.S. Provisional Application No. 61/125,027, filed on Apr. 21, 2008, titled "Use of Direction of Arrival and Empirical Mode Decomposition Algorithms to Isolate and Extract Physiological Motion Measured with a Doppler Radar"; U.S. Provisional Application No. 61/125,022, filed on Apr. 21, 2008, titled "Data Access Architectures for Doppler Radar Patient Monitoring Systems"; U.S. Provisional Application No. 61/125,020, filed on Apr. 21, 2008, titled "Use of Direction of Arrival Algorithms to Isolate and Separate Physiological Motion Measured with a Doppler Radar"; U.S. Provisional Application No. 61/125,164, filed on Apr. 22, 2008, titled "Biometric Signature Collection Using Doppler Radar System"; U.S. Provisional Application No. 61/128,743, filed on May 23, 2008, titled "Doppler Radar Based Vital Signs Spot Checker"; U.S. Provisional Application No. 61/137,519, filed on Jul. 30, 2008, titled "Doppler Radar Based Monitoring of Physiological Motion Using Direction of Arrival"; U.S. Provisional Application No. 61/137,532, filed on Jul. 30, 2008, titled "Doppler Radar Respiration Spot Checker with Narrow Bean Antenna Array"; U.S. Provisional Application No. 61/194,838, filed on Sep. 29, 2008, titled "Doppler Radar-Based Body Worn Respiration Sensor"; U.S. Provisional Application No. 61/194,836, filed on Sep. 29, 2008, titled "Wireless Sleep Monitor Utilizing Non-Contact Monitoring of Respiration Motion"; U.S. Provisional Application No. 61/194,839, filed on Sep. 29, 2008, titled "Continuous Respiratory Rate and Pulse Oximetry Monitoring System"; U.S. Provisional Application No. 61/194,840, filed on Sep. 29, 2008, titled "Separation of Multiple Targets' Physiological Signals Using Doppler Radar with DOA Processing"; U.S. Provisional Application No. 61/194,848, filed on Sep. 30, 2008, titled "Detection of Paradoxical Breathing with a Doppler Radar System"; U.S. Provisional Application No. 61/196,762, filed on Oct. 17, 2008, titled "Monitoring of Chronic Illness Using a Non-contact Respiration Monitor"; U.S. Provisional Application No. 61/200,761, filed on Dec. 2, 2008, titled "Detection of Paradoxical Breathing with a Paradoxical Breathing Indicator with a Doppler Radar System"; U.S. Provisional Application No. 61/200,876, filed on Dec. 3, 2008, titled "Doppler Radar Based Monitoring of Physiological Motion Using Direction of Arrival and An Identification Tag"; U.S. Provisional Application No. 61/141,213, filed on Dec. 29, 2008, titled "A Non-Contact Cardiopulmonary Sensor Device for Medical and Security Applications"; U.S. Provisional Application No. 61/204,881, filed on Jan. 9, 2009, titled "Doppler Radar Based Continuous Monitoring of Physiological Motion"; U.S. Provisional Application No. 61/204,880, filed on Jan. 9, 2009, titled "Doppler Radar Respiration Spot Checker with Narrow Beam Antenna Array"; U.S. Provisional Application No. 61/206,356, filed on Jan. 30, 2009, titled "Doppler Radar Respiration Spot Check Device with Narrow Beam Antenna Array: Kai Sensors Non-Contact Respiratory Rate Spot Check"; U.S. Provisional Application No. 61/154,176, filed on Feb. 20, 2009, titled "A Non-Contact Cardiopulmonary Monitoring Device for Medical Imaging System Applications"; U.S. Provisional Application No. 61/154,728, filed on Feb. 23, 2009, titled "Doppler Radar-Based Measurement of Vital Signs for Battlefield Triage"; U.S. Provisional Application No. 61/154,732, filed on Feb. 23, 2009, titled "Doppler Radar-Based Measurement of Presence and Vital Signs of Subjects for Home Healthcare"; U.S. Provisional Application No. 61/178,930, filed on May 15, 2009, titled "Aiming or Aligning Methods and Indicator Display for a Doppler Radar System;" U.S. Provisional Application No. 61/181,289, filed on May 27, 2009, titled "Intermittent Doppler Radar Respiration Spot Check;" U.S. Provisional Application No. 61/184,315, filed on Jun. 5, 2009, titled "Doppler Radar Respiration Spot Check with Automatic Measurement Length;" and U.S. Provisional Application No. 61/226,707, filed on Jul. 18, 2009, titled "Spiral Antenna for a Contacting Cardiopulmonary Sensor."

BACKGROUND

I. Field

This application in general relates to one, two, or more monitors that can assess the physiological and/or psychological state of a subject. In particular, some implementations relate to non-contact and radar-based physiologic sensors and their method of use that can provide, apnea monitoring, apnea therapy to subjects, sway cancellation, multi-parameter systems, realize cessation of breath, identify patients, or any combination thereof.

II. Description of the Related Art

Motion sensors that can obtain physiological information of a subject, such as respiratory activity, cardiac activity, cardiovascular activity, and cardiopulmonary activity on a continuous or intermittent basis can be useful in various medical applications. Unfortunately, such physiologic activity often occurs in the presence of various other motions, such as, for example, rolling over while sleeping, etc. Thus, data from such motion sensors can typically include desired components corresponding to the physiological activity being measured, and undesired components corresponding to other motions, noise, etc. Some existing systems do not adequately separate the desired components from the undesired components.

SUMMARY

One or more of these and/or other problems can be solved by a system that uses a radar-based sensor to sense physiological motion and a processing system that analyzes the data from the radar to distinguish desired data components corresponding to various physiological activity from undesired data components due to other activity, motions, noise, etc. The system can be used to obtain respiratory rate, heart rate, and physiological waveforms including, but not limited to, heart waveforms, pulse waveform, and/or a respiratory waveform. These rates and waveforms can be analyzed to assess various physiological and medical parameters such as, for example, respiratory rates, cardiac rates, respiratory effort, depth of breath, tidal volume, vital signs, medical conditions, psychological state, or location of the subject, etc. These waveforms can also be used to synchronize ventilation or medical imaging with respiratory and/or cardiac motion. The information in these rates and waveforms can be used in many embodiments, including vital signs assessments, apnea monitors, general patient monitoring, neonatal monitoring, burn victim monitoring, home monitoring of the elderly or disabled, triage, chronic illness management, post-surgical monitoring, monitoring of patients during medical imaging scans, disease detection, assessment of psychological state, psychological or psychiatric evaluation, pre-resuscitation assessment, post-resuscitation assessment, and/or lie detection. Various embodiments of the motion sensors can be used in medical applications in various environments including, but not limited to, hospitals, clinics, homes, skilled nursing facilities, assisted living facilities, health kiosks, emergency rooms, emergency transport, patient transport, disaster areas, and battlefields. Various embodiments of the motion sensors can be used for security applications including, but not limited to, security screening at airports, borders, sporting events and other public events, or as a lie detector. Various embodiments of the physiological motion sensors can distinguish valid measurement of heart and respiratory activity from interference, noise, or other motion, and it can provide continuous, point in time, intermittent and/or piecemeal data from which rates, signatures, and key variations can be recognized. Various embodiments of the physiological motion sensor can operate with no contact and work at a distance from a subject. Some embodiments of the physiological motion sensor can also operate when placed on the subject's chest in contact with the body. Various embodiments of the physiological motion sensor can operate on subjects in any position, including lying down, reclined, sitting, or standing. Various embodiments of the physiological motion sensor can operate on subjects from different positions relative to the subject, including from the subject's, from the subject's side, from the subject's back, from above the subject, and from below the subject.

Various embodiments of the motion sensors can operate as an apnea therapeutic device which may include a wireless or wired device which can be triggered during an apneic event detected by the motion sensor to provide a stimulus to the point where the subject resumes normal breathing without sleep arousal, or awakening or substantially awakening the patient from sleep.

Various embodiments of the motion sensor can include a system comprising two or more vital signs sensors and a processing unit capable of detecting, estimating and cancelling the subject's possible sway motion from the subject's vital signs.

Various embodiments of the motion sensor can implement a method of detecting apneic events, including, but not limited to, cessation of breath is based on estimating the relative amplitude of the respiratory waveform during the times of valid physiological motion that are more than a certain length of time.

Various embodiments of the motion sensors can be integrated into a separate contact based patient monitoring device and/or contact based vital signs measurement device, that can be further analyzed to provide other or more detailed vital signs.

Various embodiments of the motion sensors include one or more sensors that can be wirelessly connected to a patient identification device that can be placed on or near the subject that emits and/or re-emits a signal to provide positive patient identification.

In one aspect, a system for treating sleep apnea is provided. The system can include a wireless sleep monitor. The wireless sleep monitor can include one or more antennas, with each of the one or more antennas configured to receive electromagnetic radiation and/or transmit electromagnetic radiation. The wireless sleep monitor can also include one or more processors configured to extract information related to cardiopulmonary motion by executing at least one of a demodulation module, a non-cardiopulmonary motion detection module, and a rate estimation module. The one or more processors can be further configured to detect an apneic event. In addition, the wireless sleep monitor can include a communications module configured to communicate with a therapeutic device. The therapeutic device can be configured to perform at least one action related to a sleep apnea state of the subject. The wireless sleep monitor can also include a therapeutic device comprising a bio-feedback mechanism configured to stimulate the patient in order to treat an anatomic or physiologic condition associated with apnea, such as stimulating a nerve and/or muscle, such as the hypoglossal nerve region in the patient's neck when an apneic event is detected. The stimulant causes the patient to shift position, swallow, cough, move the palate or tongue, or restore muscle tone in the genioglossus muscle in the patient's neck, thereby restoring the upper airway passage. In some embodiments, the therapeutic device can be configured to stimulate one or more regions of a patient's brain to treat central apnea.

According to another aspect, a system for sensing a physiological motion is provided. The system can include one or more sources for generating electromagnetic radiation, wherein the frequency of the generated electromagnetic radiation is in the radio frequency range. The system can also include one or more communications modules configured to perform at least one of the following: transmit the generated electromagnetic radiation towards a subject and receive a radiation scattered at least by the subject. In addition, the system can include one or more antennas, where each of the one or more antenna is configured to transmit electromagnetic radiation and/or receive electromagnetic radiation. The system can further include one or more processors configured to: extract information related to cardiopulmonary motion by executing at least one of a demodulation algorithm, a non-cardiopulmonary motion detection algorithm, a rate estimation algorithm, a paradoxical breathing algorithm and a direction of arrival algorithm; analyze the signal to obtain information corresponding to a non-cardiopulmonary motion or other signal interference; extract a Doppler shifted signal from the scattered radiation; and transform the Doppler shifted signal to a digitized motion signal, said digitized motion signal comprising one or more frames, wherein the one or more frames comprise time sampled quadrature values of the digitized motion signal; isolate a signal corresponding to a physiological movement at least a portion part of the subject; obtain information corresponding to the physiological movement of at least a portion of the subject based on the isolated signal, said information substantially separate from at least one of said non-cardiopulmonary motion and other signal interference; and estimate one or more of the group consisting of: non-contact, spot, interval and continuous vital signs parameters and communicate the information to an output system that is configured to perform an output action. The system can be configured to perform at least one of the following: screen a sleep disorder, diagnose a sleep disorder, and provides therapy to the sleep disorder.

Another aspect is a method for treating sleep apnea. The method can include detecting, via a wireless sleep monitor, an apneic event associated with a subject; transmitting information related to the apneic event to a therapeutic device configured to stimulate the patient in order to treat an anatomic or physiologic condition associated with apnea, including a nerve or muscle, such as the hypoglossal nerve or other nerve in the subject's neck all without necessarily arousing the patient from sleep but terminating the apneic event.

Yet another aspect is a vital-signs monitoring system. The system can include a first vital sign sensor and a second vital sign sensor, the second vital sign sensor spaced apart from the first vital sign sensor, the first vital sign sensor and the second vital sign sensor comprising one or more antennas configured to perform one or more of the following: transmit electromagnetic radiation and receive electromagnetic radiation. In addition, the system can include one or more processors configured to extract information related to cardiopulmonary motion by executing at least one of a demodulation module, a non-cardiopulmonary motion detection module, and a rate estimation module; wherein the one or more processors are further configured to cancel the sway motion associated with a subject and generate a cardiopulmonary signal associated with the subject.

Another aspect is a method for detecting, estimating and cancelling sway motion of a subject from vital sign measurements associated with the subject. The method can include receiving signals generated by two or more sensors including at least a first sensor and a second sensor, wherein the received signals include at least one of demodulated signals and signals associated with an I path and a Q path; and performing a linear combination of the received signals such that signal power associated with the received signals is substantially minimized.

In accordance with yet another aspect, a method of detecting an apneic event is provided. The method can include monitoring an instantaneous amplitude over time of a respiratory signal by squaring the respiratory signal and filtering the respiratory signal via a moving average filter; generating a cumulative histogram of the instantaneous amplitude; setting one or more thresholds for a low breathing amplitude based on the cumulative histogram; determining one or more apneic timespans based on comparing the instantaneous amplitude to at least one of the one or more thresholds within the time span associated with valid physiological motion; and reporting timestamps corresponding to at least one apneic event.

According to another aspect, a system for integrated monitoring of physiological parameters of a subject is provided. The system can include one or more non-contact vital sign sensors configured to: generate a signal, such as an electromagnetic signal, e.g., a radio frequency (RF) signal; transmit the generated RF signal towards a subject; receive radiation scattered by the subject; extract a Doppler shifted signal from the scattered radiation; and derive information corresponding to physiological movement of at least a portion of the subject that is substantially separate from non-cardiopulmonary motion. The system can also include at least one of a separate contact based patient monitoring device and a separate contact based vital signs measurement device.

Yet another aspect is a system for monitoring physiological signs associated with a subject and positively identifying the subject. The system can include at least one of a contact based patient monitoring device, a non-contact based patient monitoring device, and a vital sign measurement sensor. The system can also include a patient identification device in communication with at least one of the contact based patient monitoring device, the non-contact based patient monitoring device, and the vital sign measurement sensor.

In one aspect, another system for detecting and treating sleep apnea is provided. The system can include one or more of a sensor, such as, for example, a non-contact radar sensor aimed at the chest to detect ventilatory effort, a microphone embedded in a therapeutic device such as an anatomic such as a neck patch sensor to monitor airflow, a nasal airflow sensor as an auxiliary airflow monitor, a pulse oximeter sensor to detect oxygen saturation and heart rate, and/or an accelerometer to detect body motion. One or more of the sensors can be coupled with a sensor processing unit that can be worn on the patient's arm or another location that may detect apneic events. One or more of the sensors may be wired to the sensor processing unit or may wirelessly communicate to the sensor processing unit. In addition, the sensor processing unit can include a communications module configured to communicate with a therapeutic device. The therapeutic device can be configured to perform at least one action related to a sleep apnea state of the subject. The wireless sleep monitor can also include a therapeutic device comprising a bio-feedback mechanism configured to stimulate the patient in order to treat an anatomic or physiologic condition associated with apnea, such as the brain, a nerve or a muscle, including but not limited to the hypoglossal nerve region in the patient's neck when an apneic event is detected causing the patient to shift position, swallow, cough, move the palate or tongue, or restore muscle tone in the genioglossus muscle in the patient's neck, thereby restoring the upper airway passage. The sensor processing unit may detect the end of the apnea event and cease any electrical signal and mechanical stimulation in the neck patch. The system may include application software for sleep quality analysis, e.g., web, PC, tablet, or smartphone-based software.

In one aspect, another system for diagnosing sleep apnea is provided. The system can include one or more sensors, such as a non-contact radar sensor aimed at the chest to detect ventilatory effort, a nasal airflow sensor as an auxiliary airflow monitor, a pulse oximeter sensor to detect oxygen saturation and heart rate, and/or an accelerometer to detect body motion. One or more of the sensors can be coupled with a sensor processing unit, e.g., worn on the patient's arm or other location that may detect apneic events. One or more of the sensors may be wired to the sensor processing unit or may wirelessly communicate to the sensor processing unit. The system may include a web based or PC based application software to assist the clinician in assessing subject's apnea severity by reporting sleep breathing disorder events and computing and reporting the AHI (apnea-hypopnea index), event duration, and timestamps, and/or other patient-related information.

In one aspect, a system for detecting and treating snoring is provided. The system can include a sensor, such as an auditory or vibratory sensor, such as a microphone embedded in the therapeutic device such as a neck patch sensor to detect snoring events. The therapeutic device can be configured to perform at least one action related to detecting and treating a snoring event. The therapeutic device may comprise a bio-feedback mechanism configured to stimulate the hypoglossal nerve region in the patient's neck when a snoring event is detected causing the patient to shift position, swallow, cough, move the palate or tongue, or restore muscle tone in the genioglossus muscle in the patient's neck, thereby restoring the upper airway passage and possibly terminating the snoring event. The therapeutic device may detect the end of the snoring event and cease any electrical signal and/or mechanical stimulation in the therapeutic device. The device may be coupled with a separate stand-alone device, such as a sensor, smartphone, or computer tablet with its own display, user interface and controls, clock, recording hardware and software, and/or communications hardware and software.

BRIEF DESCRIPTION OF THE DRAWINGS

FIG. 6C illustrates the acquired signal fit to a curve or a line.

DETAILED DESCRIPTION

I. Non-Contact Vital Signs Monitoring

Figure 1A:
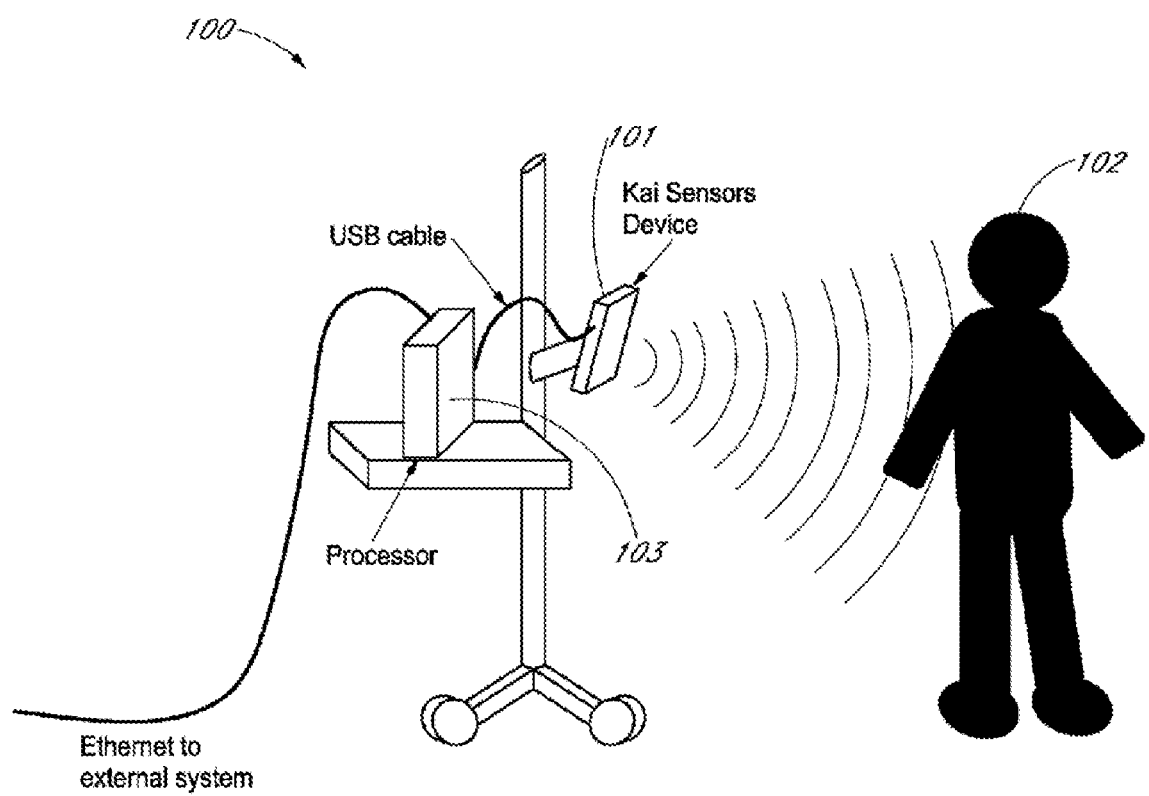
FIG. 1A schematically illustrates an embodiment of a physiological motion sensor system comprising radar.

One embodiment includes a method of sensing motion using a motion sensor, the method can include generating electromagnetic radiation from a source of radiation, wherein the frequency of the electromagnetic radiation is in the radio frequency range, transmitting the electromagnetic radiation towards a subject using one or more transmitters, receiving a radiation scattered at least by the subject using one or more receivers, extracting a Doppler shifted signal from the scattered radiation, transforming the Doppler shifted signal to a digitized motion signal, the digitized motion signal comprising one or more frames, wherein the one or more frames include time sampled quadrature values of the digitized motion signal, demodulating the one or more frames using a demodulation algorithm executed by one or more processors to isolate a signal corresponding to a physiological movement of the subject or a part of the subject, analyzing the signal to obtain information corresponding to a non-cardiopulmonary motion or other signal interference, processing the signal to obtain information corresponding to the physiological movement of the subject or a part of the subject, substantially separate from the non-cardiopulmonary motion or other signal interference, and communicating the information to an output system that is configured to perform an output action.

In one embodiment, the output system includes a display unit configured to display the information. In one embodiment, the output system includes an audible system that is configured to report information or alerts audibly based on the information. In one embodiment, the output system includes an external medical system that is configured to perform an action based on the information. In one embodiment, the demodulating algorithm includes a linear demodulation algorithm, an arc-based demodulation algorithm or a non-linear demodulation algorithm. In one embodiment, the information is displayed at least alphanumerically, graphically and as a waveform.

In various embodiments the demodulating algorithm includes projecting the signal in a complex plane on a best-fit line, projecting the signal in a complex plane on a principal eigenvector, or aligning a signal arc to a best-fit circle and using the best-fit circle parameters to extract the angular information from the signal arc.

In various embodiments demodulating includes computing in one or more processors a first set of covariance matrices of a first subset of frames selected from the one or more frames, determining a first A-matrix, wherein the first A-matrix includes a weighted sum of the first set of covariance matrices, determining a first parameter vector corresponding to a first primary value of the first A matrix, storing the first parameter vector in a memory device which is in communication with the one or more processors. In one embodiment, demodulation includes, computing in the one or more processors a second set of covariance matrices of a second subset of frames selected from the one or more frames, determining a second A-matrix, wherein the second A-matrix includes a weighted sum of the second set of covariance matrices, determining a second parameter vector corresponding to a second primary value of the second A-matrix, calculating an inner product of the first parameter vector and the second parameter vector, multiplying the second parameter vector by the sign of the inner product, and projecting the values of the second frame on the second parameter vector to obtain the demodulated signal. In one embodiment, the first primary value includes the largest eigenvalue of the first A-matrix and the first primary vector includes an eigenvector corresponding to the eigenvalue. In one embodiment, the second primary value includes the largest eigenvalue of the second A-matrix and the second primary vector includes an eigenvector corresponding to the eigenvalue.

In one embodiment, the source of radiation includes an oscillator. In one embodiment, the one or more transmitters include one or more antennae. In one embodiment, the one or more receivers include one or more antennae or arrays of antennae. In one embodiment, the transmitting and receiving antennae are the same antennae. In one embodiment, the receiver includes a homodyne receiver. In one embodiment, the receiver includes a heterodyne receiver. In one embodiment, the receiver includes a low-IF receiver configured to transform the Doppler-shifted signal to a Doppler-shifted signal comprising frequencies in a low intermediate frequency range, which is digitized and digitally transformed to a digitized motion signal.

In one embodiment, the one or more processors include at least one of a digital signal processor, a microprocessor and a computer. In one embodiment, the output system includes a display unit configured to display information regarding the physiological movement of a user at a remote location.

In one embodiment, analyzing the signal includes executing a non-cardiopulmonary motion detection algorithm configured to detect the absence of non-cardiopulmonary motion is detected if the signal includes a single stable source or the presence of non-cardiopulmonary signal if at least the signal is unstable or at least the signal has multiple sources.

In one embodiment, analyzing the signal includes executing a non-cardiopulmonary motion detection algorithm configured to detect the presence of non-cardiopulmonary motion if the signal indicates an excursion larger than the subject's maximum chest excursion from cardiopulmonary activity.

In one embodiment, analyzing the signal includes executing a non-cardiopulmonary motion detection algorithm configured to detect the presence of non-cardiopulmonary motion if a best-fit vector related to linear demodulation changes significantly.

In one embodiment, analyzing the signal includes executing a non-cardiopulmonary motion detection algorithm configured to detect the presence of non-cardiopulmonary motion if a RMS difference between a complex constellation of the signal and a best fit vector related to linear demodulation changes significantly.

In one embodiment, analyzing the signal includes executing a non-cardiopulmonary motion detection algorithm configured to detect the presence of non-cardiopulmonary motion if an origin or radius of a best-fit circle related to arc-based demodulation changes significantly.

In one embodiment, analyzing the signal includes executing a non-cardiopulmonary motion detection algorithm configured to detect the presence of non-cardiopulmonary motion if a RMS difference between a complex constellation of the signal and a best-fit circle related to arc-based demodulation changes significantly.

In one embodiment, analyzing the signal includes executing a non-cardiopulmonary motion detection algorithm by one or more processors to detect the presence or absence of non-cardiopulmonary motion or other signal interference from the digitized motion signal, wherein the non-cardiopulmonary motion detection algorithm includes a first mode which detects a presence of non-cardiopulmonary motion or other signal interference and a second mode which detects a cessation of non-cardiopulmonary motion or other signal interference.

In one embodiment, the first mode includes selecting a first subset of frames from the one or more frames and computing in the one or more processors a first set of covariance matrices of the first subset of frames filtered by a low-pass filter, determining a first A-matrix wherein the A-matrix includes a weighted sum of the first set of covariance matrices, determining a first parameter vector corresponding to a first primary value of the first A matrix, storing the first parameter vector in a memory device which is in communication with the one or more processors. One embodiment further includes computing in the one or more processors a second set of covariance matrices of a second subset of frames filtered by the low-pass filter, determining a second A-matrix, wherein the A-matrix includes a weighted sum value of the second set of covariance matrices, determining a first and a second primary value of the second A-matrix, determining a second parameter vector corresponding to the first primary value of the second A-matrix, calculating an inner product of the first parameter vector and the second parameter vector, calculating a ratio of the first primary value of the second A matrix to the second primary value of the second A matrix, calculating a first energy corresponding to the average energy of a third subset of frames filtered by a high-pass filter and a second energy corresponding to the average energy of a fourth subset of frames filtered by a high-pass filter, and calculating a ratio of the second energy to the first energy. In one embodiment, the first primary value includes the largest eigenvalue of the first A-matrix and the first primary vector includes an eigenvector corresponding to the eigenvalue. In one embodiment, the first primary value of the second A-matrix includes the second largest eigenvalue of the second A-matrix, the second primary value of the second A-matrix includes the largest eigenvalue of the second A-matrix and the second primary vector of the second A-matrix includes an eigenvector corresponding to the first primary value of the second A-matrix.

One embodiment includes computing in the one or more processors a first condition, the first condition being the inner product is less than a first threshold value or the ratio of the first primary value of the second A matrix to the second primary value of the second A matrix is less than a second threshold value or the ratio of the second energy to the first energy is greater than a third threshold value, wherein the presence of non-cardiopulmonary motion or other signal interference is detected if the first condition is true and the ratio of the second energy to the first energy is greater than a fourth threshold value. In one embodiment, the first threshold value is approximately between 0.6 and 1.

In one embodiment, the second threshold value is approximately between 4 and 12. In one embodiment, the third threshold value is approximately between 4 and 20. In one embodiment, the fourth threshold value is approximately between 0.1 and 0.8.

In one embodiment, the second mode includes selecting in the one or more processors each and every consecutive subset of frames within a fifth subset of frames, computing in the one or more processors covariance matrices for every subset of frames computing in the one or more processors an A'-matrix for each subset of frames, wherein the A'-matrix is the weighted average of the covariance matrices in the subset, computing in the one or more processors a rho-matrix, wherein each element of the rho-matrix corresponds to a first primary vector of the corresponding A'-matrix, computing the inner product of each pair of primary vectors in the rho-matrix and selecting a minimum absolute value of the inner products, calculating an A matrix which is the sum of the covariance matrices in a sixth subset of frames, determining the first primary value of the A-matrix and the second primary value of the A matrix, calculating the ratio of the first primary value of the A matrix to the second primary value of the A matrix, One embodiment includes computing in the one or more processors a second condition, the second condition being the minimum absolute value of the inner products is greater than a first threshold value and the ratio of the first primary value to the second primary value is greater than a second threshold value, wherein the cessation of non-cardiopulmonary motion or other signal interference is detected if the second condition is true. In one embodiment, the fifth threshold value is approximately between 0.6 and 1. In one embodiment, the sixth threshold value is approximately between 4 and 12. In one embodiment, the first primary vector includes an eigenvector corresponding to the largest eigenvalue of the corresponding A'-matrix. In one embodiment, the first primary value includes the largest eigenvalue of the A-matrix and the second primary value includes the second largest eigenvalue of the A-matrix. One embodiment includes computing a frame from the one or more frames when the non-cardiopulmonary motion substantially ceased. In one embodiment, one or more frames preceding the frame are discarded.

One embodiment includes a method of estimating the rate of a physiological motion using a motion sensor, generating an electromagnetic radiation from a source of radiation, wherein the frequency of the electromagnetic radiation is in the radio frequency range, transmitting the electromagnetic radiation towards a subject using one or more transmitters, receiving a radiation scattered at least by the subject using one or more receivers, extracting a Doppler shifted signal from the scattered radiation, transforming and digitizing the Doppler shifted signal to a digitized motion signal, the digitized motion signal comprising one or more frames, wherein the one or more frames include time sampled quadrature values of the digitized motion signal, demodulating the one or more frames using a demodulation algorithm executed by one or more processors to isolate a signal corresponding to a physiological movement of the subject or a part of the subject, executing a non-cardiopulmonary motion detection algorithm by the one or more processors to identify from the digitized motion signal one or more non-cardiopulmonary motion detection events or other signal interference events corresponding to the presence or absence of a non-cardiopulmonary motion or other signal interference, executing by one or more processors a rate estimation algorithm to estimate a rate of the physiological movement, and providing information related to at least the rate of the physiological movement of the subject or a part of the subject to an output unit that is configured to output the information.

In one embodiment, the rate estimation algorithm includes collecting a plurality of samples from the demodulated frames, identifying one or more samples from the plurality of samples corresponding to non-cardiopulmonary motion detection events and setting to zero the one or more samples from the plurality of samples to obtain at least a first subset of the plurality of samples, and subtracting in the one or more processors a mean of the first subset from the first subset. One embodiment includes calculating in the one or more processors a Fourier transform of the samples included in the first subset to obtain a magnitude spectrum of the samples in the first subset. In one embodiment, the estimated frequency domain rate of the physiological movement corresponds to the largest magnitude component in the spectrum of the samples in the first subset. One embodiment includes identifying either at least three positive zero crossings or at least three negative zero crossings in the first subset, identifying at least a first value for the samples within a first and a second zero crossing, the first value being the largest magnitude positive value or largest magnitude negative value, identifying at least a second value for the samples within a second and a third zero crossing, the second value being the largest magnitude positive value or largest magnitude negative value comparing the first and second values against a threshold value, identifying at least a first breathing event if the first value is greater than a threshold value, identifying at least a second breathing event if the second value is greater than a threshold value, and estimating a time domain respiration rate based on at least the first and second breathing events and the time interval between the first, second and third zero crossings. One embodiment includes calculating in the one or more processors a Fourier transform of the samples included in the first subset to obtain a magnitude spectrum of the samples in the first subset, estimating a frequency domain respiration rate of the physiological movement that corresponds to the largest magnitude spectrum of the samples in the first subset, and comparing the time domain rate and the frequency domain rate to verify an accuracy of the time domain rate and the frequency domain rate.

In one embodiment, the rate estimation algorithm includes identifying at least three consecutive peaks from the plurality of samples, such that a valley is included between two consecutive peaks, and determining a respiration rate based on a number of consecutive peaks detected and the time interval between a first and a last peak.

In one embodiment, the rate estimation algorithm includes identifying at least three consecutive valleys from the plurality of samples, such that a peak is included between two consecutive valleys, and determining a respiration rate based on a number of consecutive valleys detected and the time interval between a first and a last valley. In one embodiment, the rate algorithm selects whether to identify peaks or valleys depending on which occurs first. In one embodiment, the rate estimation algorithm averages the respiration rate based on a number of consecutive peaks and the respiration rate based on a number of consecutive valleys to improve the robustness of the rate estimate.

Figure 1B:
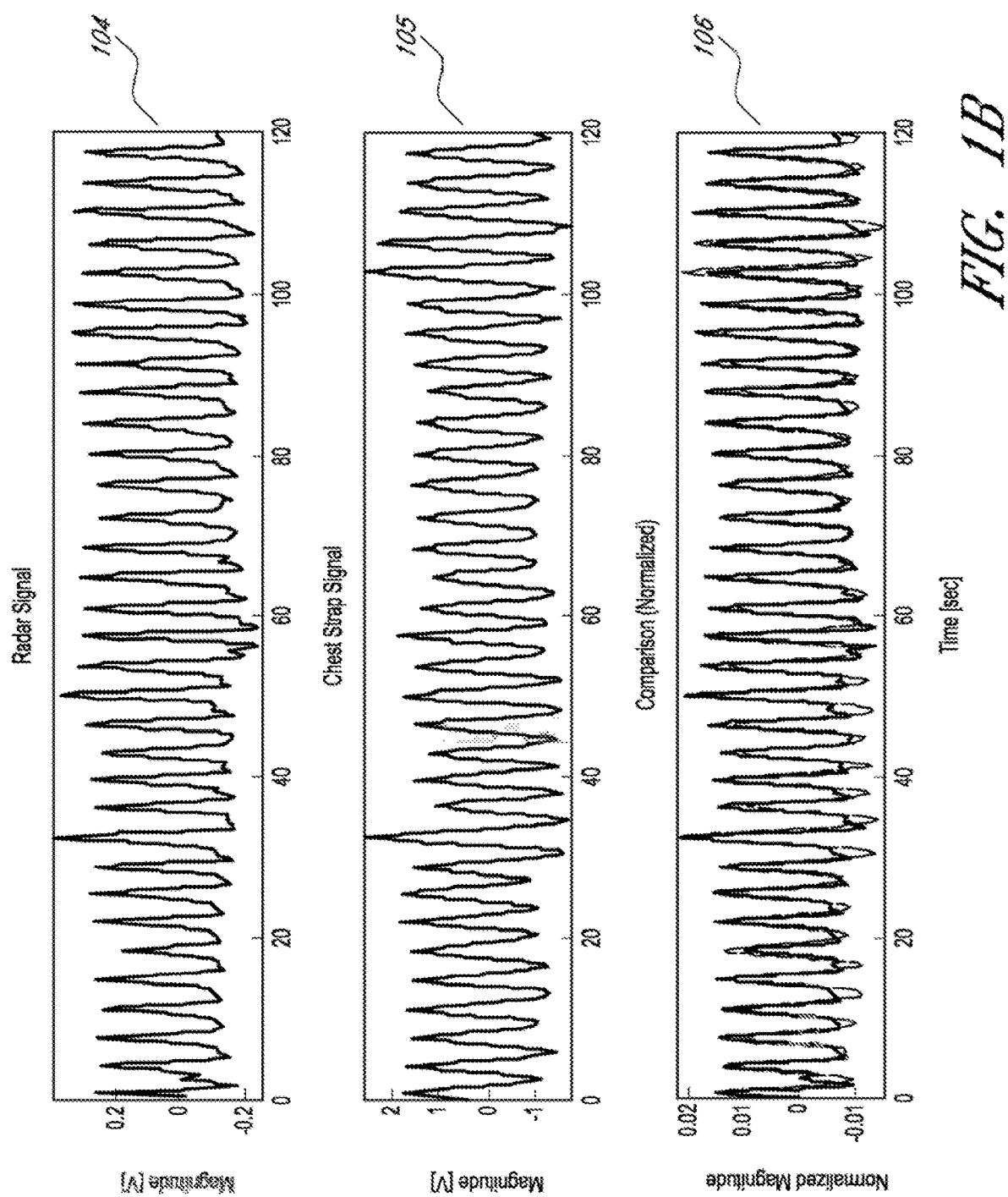
FIGS. 1B-1F graphically illustrate measurements obtained by the system illustrated in FIG. 1A.

FIG. 1A shows a physiological motion sensor system 100 wherein a radar 101 senses motion and/or physiologic activity of a subject 102. Data from the radar 101 is provided to a processing system 103 configured to analyze the radar data to determine various desired physiological parameters and provide output information regarding the physiological parameters to an output system and/or device configured to perform an output action. In various embodiments, the output device can include a display system configured to display an audible system configured to report information or issue alerts or a medical device configured to perform a function based on the information. The system 100 can further include a communications system configured to communicate using wired and/or wireless communication links. The communications system can use standard or proprietary protocols. FIG. 1B shows an example of a measurement obtained by the system 100 as displayed on a display unit.

FIGS. 1B-1F illustrate examples of measurements obtained by the system 100. The measurements can include waveforms due to cardiopulmonary activity of a subject 102 displayed on a display unit.

FIG. 1B illustrates the waveforms obtained by embodiments of the system 100 described above for a 54-year-old male subject with a body mass index (BMI) of 23 with Hypertension and Congestive Heart Failure. Plot 104 of FIG. 1B shows the physiological motion signal (e.g., respiratory rate and the amplitude of respiration) detected by the radar-based physiological motion sensor system. Plot 105 illustrates the physiological motion signal detected by a conventional contact physiological motion sensor (e.g., a chest strap). Plot 106 shows the comparison between the normalized motion signal detected by the radar-based physiological motion sensor and the normalized conventional sensor. Plot 106 shows good correspondence between the two signals.

Figure 1C:
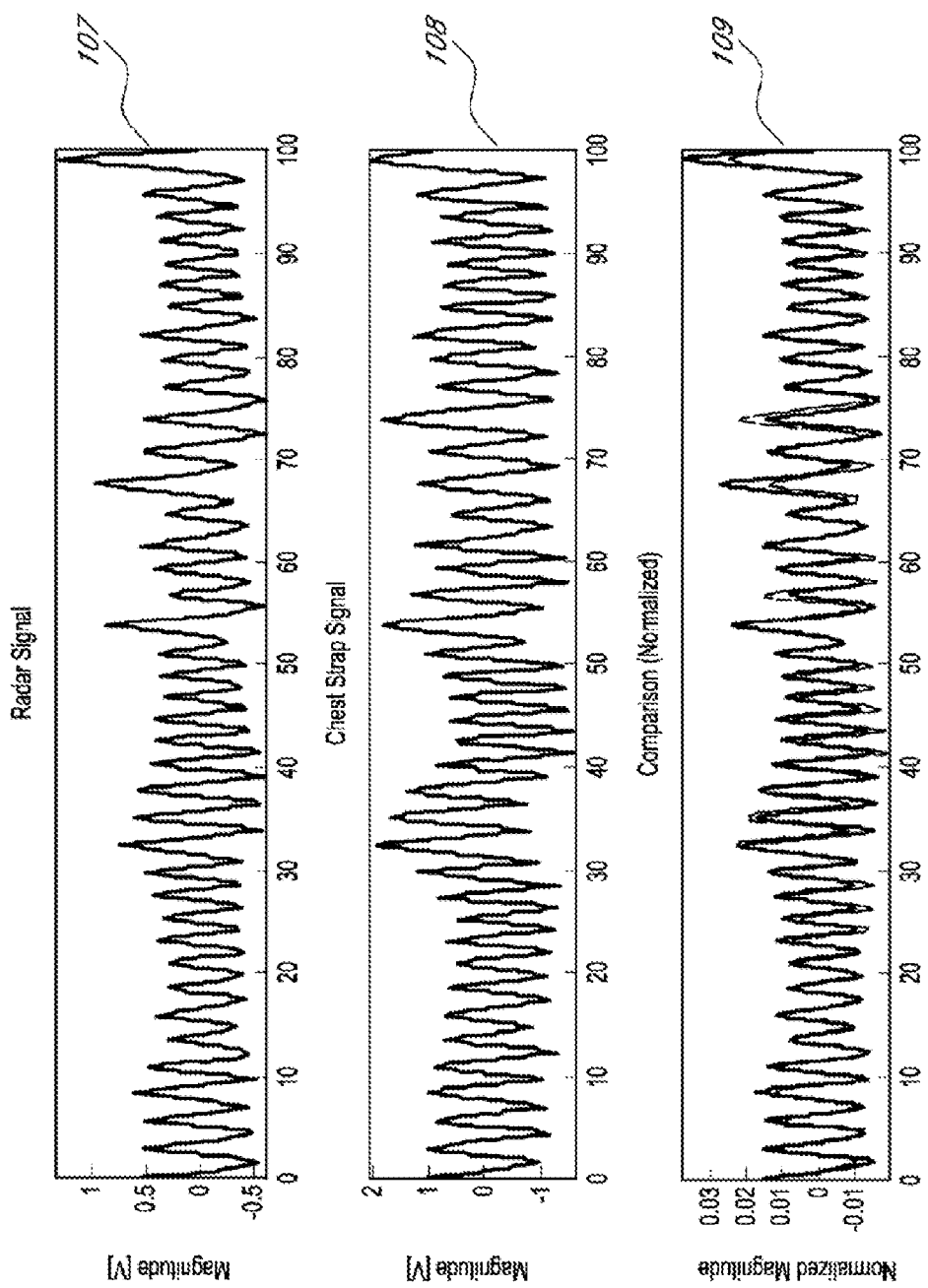

FIG. 1C illustrates variations in the respiratory rate and the amplitude of respiration obtained by embodiments of the system 100 described above for a 44-year-old male with a BMI of 40, with Diabetes, Hypertension, and CAD. Plot 107 of FIG. 1C shows the physiological motion signal (e.g., respiratory rate and the amplitude of respiration) detected by the radar-based physiological motion sensor system. Plot 108 illustrates the physiological motion signal detected by a conventional contact physiological motion sensor (e.g., a chest strap). Plot 109 shows the comparison between the normalized motion signal detected by the radar-based physiological motion sensor and the normalized conventional sensor. Like the plot 106 shown in FIG. 1B, plot 109 shows good correspondence between the two signals.

Figure 1D:
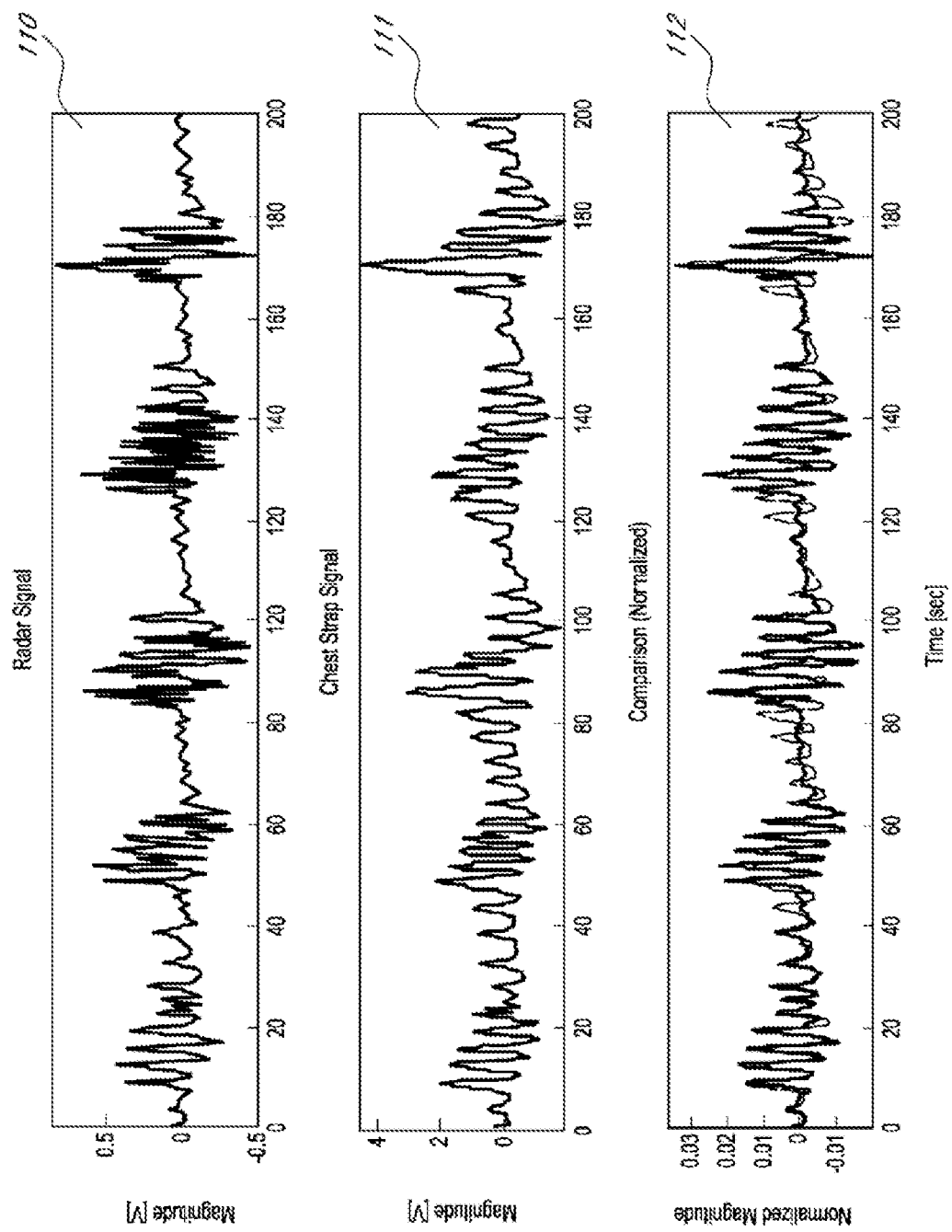

FIG. 1D illustrates the physiological motion signal obtained by an embodiment of the system 100 for a 55-year-old male with a BMI of 40, with High Cholesterol, Hypertension, and CAD, while he was snoring. Plot 110 shows the motion signal detected by the radar-based physiological motion sensor and illustrates detection of apnea (cessation of breathing) and variation in the respiration signal baseline. Plot 111 is a corresponding measurement obtained by a conventional monitor while plot 112 illustrates the comparison between the conventional monitor and the system 100.

Figure 1E:
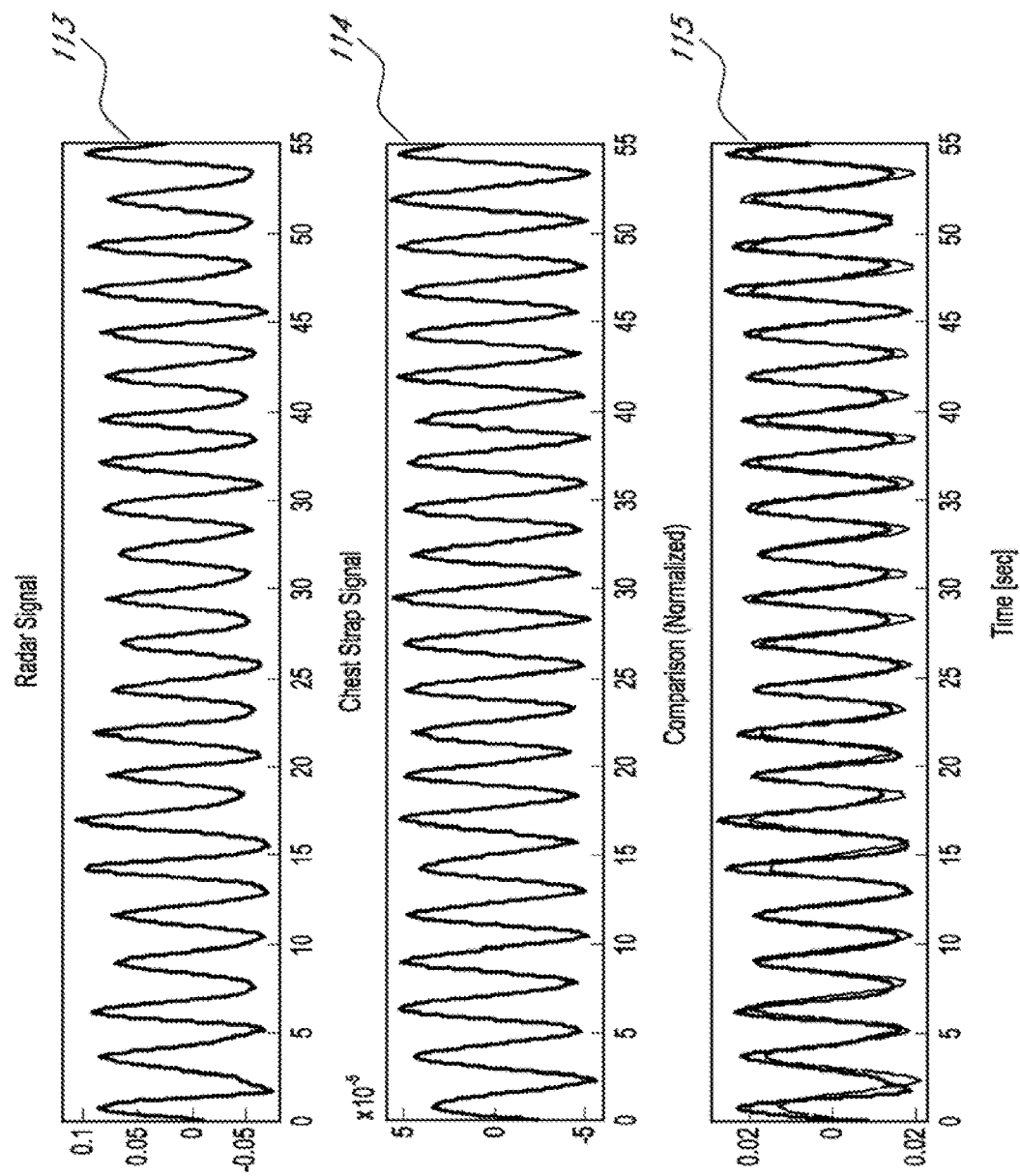

FIG. 1E illustrates the physiological motion signal obtained by an embodiment of the system 100 for a 59-year-old female with a BMI of 30, with COPD and CHF. Plot 113 shows the measurement obtained by the physiological motion sensor of system 100. Plot 114 shows the corresponding measurement obtained by a conventional sensor and plot 115 shows the comparison between the two measurements.

Figure 1F:
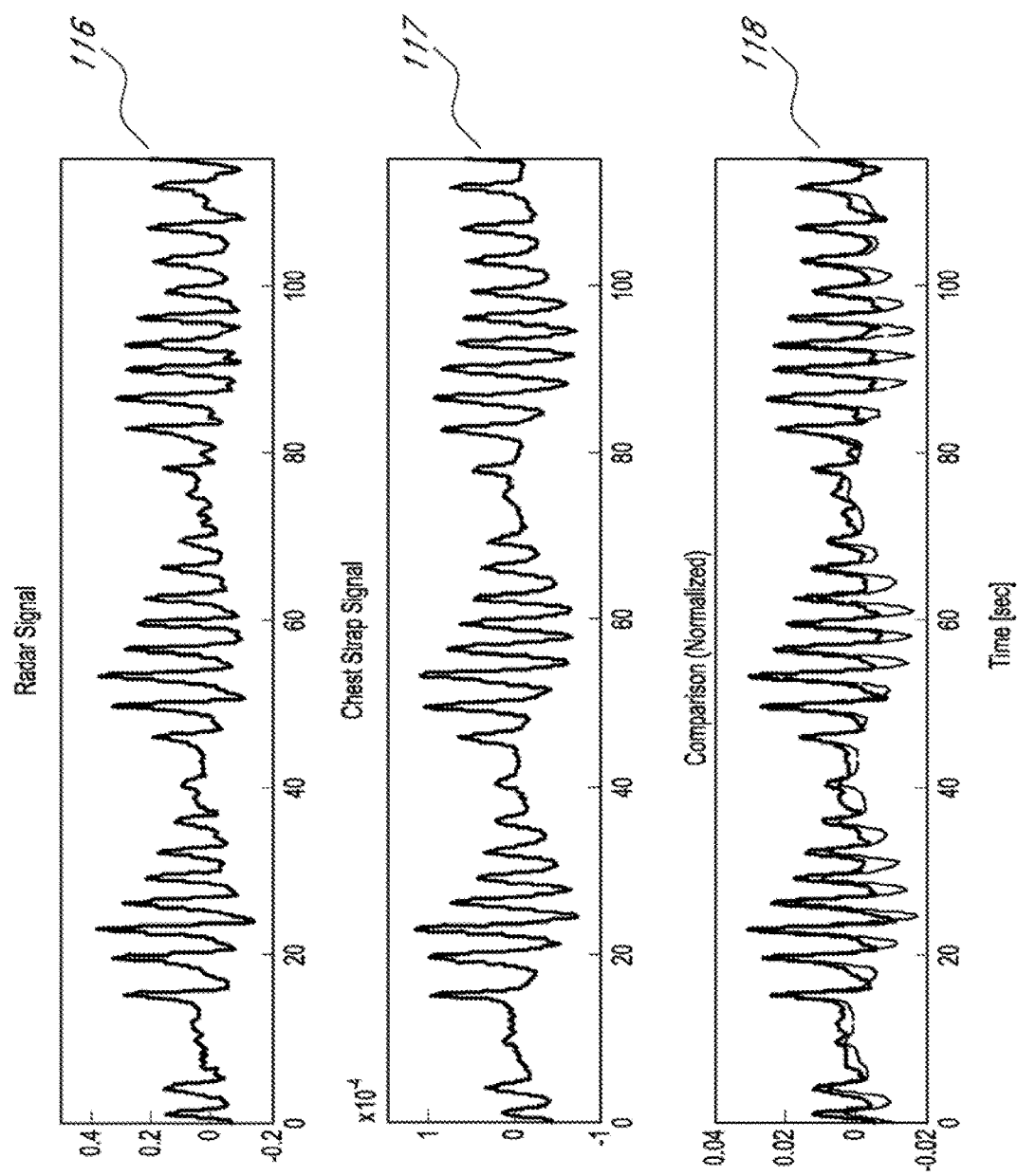

FIG. 1F illustrates the physiological motion signal obtained by an embodiment of the system 100 for a 57-year-old Female with a BMI of 38, with CHF and CAD. Plot 116 illustrates detection of apnea (cessation of breathing) and variation in the respiration signal baseline for the subject. Plot 117 illustrates a corresponding measurement obtained by a conventional sensor and plot 118 shows the comparison between the two.

In various embodiments, the radar-based physiological sensor can include a user interface to allow a user to enter information or to allow the user to enter commands and/or instructions. In various embodiments, the user interface can include a start button and a stop button. In various embodiments, the user interface can include a clear button. In various embodiments, the user interface can include additional buttons (e.g., a save button, a print button, etc.) or a keypad.

Figure 2:
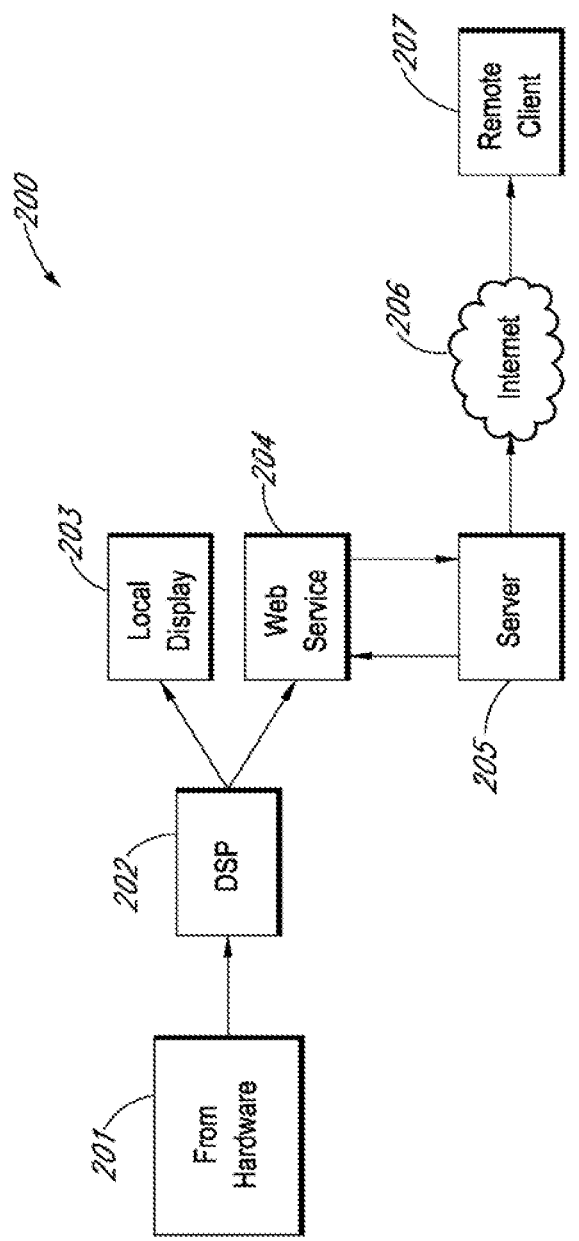
FIG. 2 schematically illustrates a block diagram of a radar-based physiological motion sensor system integrated with a remote interface.

In various embodiments, the system 100 can communicate the information to a remote display and/or a central server or one or more computing devices. In some embodiments, SOAP web service can communicate data to one or more computing devices, such as a server. From the one or more computing devices, the respiration data can be accessed by a remote client with a browser and a network connection, such as an internet connection. FIG. 2 illustrates a block diagram of a system integrated with a remote interface 200. The system illustrated in FIG. 2 includes a radar-based physiological sensor 201 in electrical communication with a signal processor 202. The information from the signal processor can be displayed locally on a local display 203 or can be stored in a server 205 over a web service 204. A remote client 207 can access the information stored on the server using a network, such as the internet 206, or another communication protocol.

Figure 3:
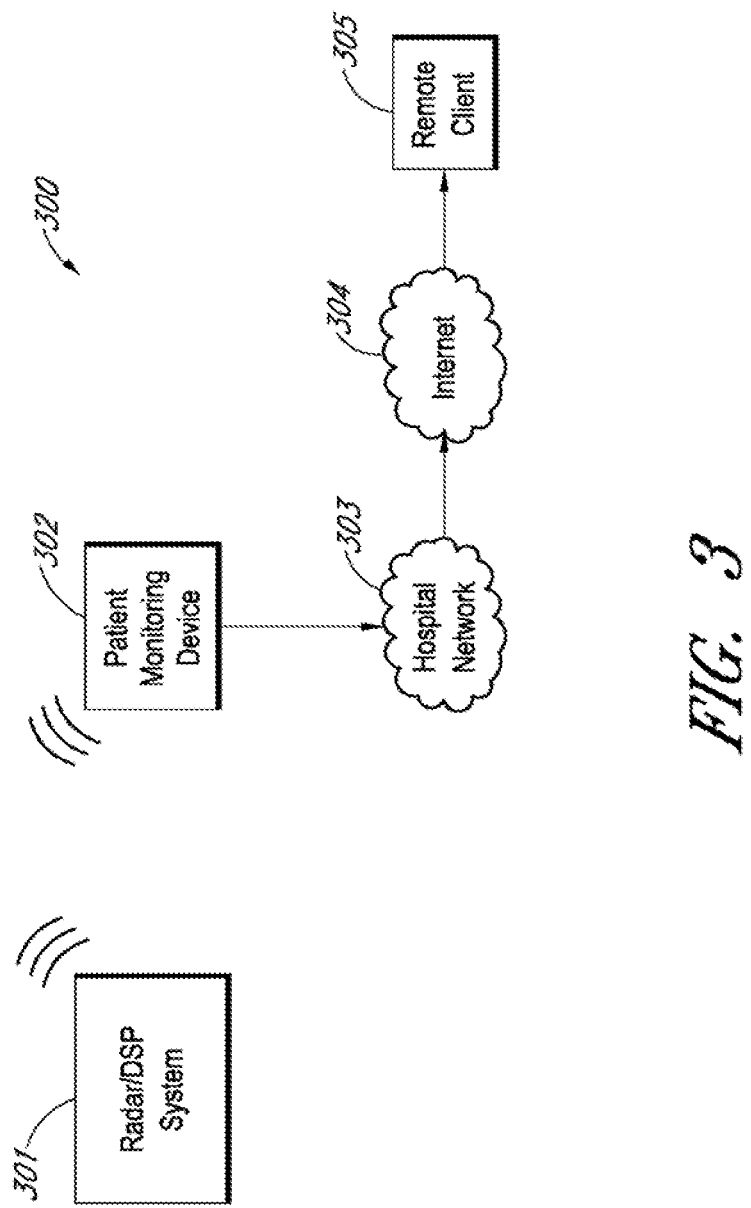
FIG. 3 schematically illustrates a block diagram of a system including radar-based physiological motion sensor including an add-on module.

In various embodiments, the system 100 can include an add-on module with wireless connectivity. FIG. 3 illustrates a block diagram of a system 300 including radar-based physiological sensor including an add-on module. As illustrated in FIG. 3, the device 301 is networked to a patient monitoring system 302 using a personal area network technology such as Bluetooth, Ultra Wide Band, Wireless USB, etc. The patient monitoring system 302 can display the cardiopulmonary motion information on its local interface and/or forward the data to a remote database over a network, such as the internet 304 or a hospital network 303, such that the information can be accessed by a remote client 305.

In various embodiments, the continuous vital signs monitor can also be used in a skilled nursing facility, in a similar embodiment to the hospital monitor. Embodiments of this device can be used for general vital signs monitoring of the elderly or ill, and can also be used for early detection of pneumonia. Embodiments of the continuous vital signs monitor can also be used in emergency vehicles (e.g., ambulances, helicopters, etc.) to monitor a patient during emergency transport. Various embodiments of the system 100 can also determine the duration of subject activity or the percentage of time the subject is active. This information can be used to provide an activity index. Changes in the activity index can be used as indicators of a change in health state. In various embodiments, the physiological motion sensor can be used to detect battlefield survivors and monitor their physiological signals. In various embodiments, a software based array configuration that is executable by one or more processors can be applied to Doppler radar to search for survivors in detecting mode, and to track them in target mode by focusing the beam. Survivor location can be determined from DOA processing at dual or multiple frequencies.

As described in more detail below, the system 100 can implement, which can include storing computer-executable instructions in non-transitory memory, algorithms for calculating respiratory rate, accuracy of the respiratory rate, algorithms to recognize inaccurate data, to recognize interfering motion, to recognize electrical signal interference, to recognize electrical noise, to report varying rates, to analyze the regularity or irregularity of the respiratory rate and to signal or alert a user if the respiratory rate is high or low, etc.

As described in more detail below, the system 100 can include hardware and/or software which is executable by one or more processors to improve signal quality, such as, for example, RF leakage cancellation, DC cancellation, noise cancellation, low IF architecture, homodyne system balancing, etc. Various embodiments of the system 100 described herein can have the capability to discern between cardiopulmonary and other motions. In various embodiments of the system 100, methods and algorithms for motion discrimination and detection can enable increased accuracy of cardiopulmonary data. Various embodiments described herein employ methods of decreasing the delay between the occurrence of an event and the reporting and display of that event by DC cancellation and high speed data acquisition. A low time delay can typically be desirable for applications in which another device uses the reported event to initiate and/or trigger another action. A low time delay can also improve synchronization with other measurements. The respiration and/or heart waveforms that are generated by the various embodiments described herein can be used to trigger actions by other systems. For example, various embodiments relate to triggering medical imaging (e.g., with CT or MRI scans) based on cardiac or respiratory displacement and/or triggering assistive ventilation based on spontaneous respiratory effort. The respiration or heart waveforms that are generated by the various embodiments described herein can be used to provide physiological synchronization with other systems. For example, various embodiments relate to synchronizing cardiopulmonary motion and/or other motion to medical imaging (e.g., CT scans or MM) systems, assistive ventilation systems, polygraph systems, security screening systems, biofeedback systems, chronic disease management systems, exercise equipment, or any combination thereof.

Various embodiments of the system 100 can automatically, using any combination of features of the algorithms related to Direction of Arrival (DOA), track a subject's physiological signals as the subject moves around, e.g., up and down in a bed. Various embodiments of the system 100 can automatically, using any combination of features of the algorithms related to DOA, track a subject's location as the subject moves around, e.g., up and down in a bed. Various embodiments of the system 100 can be configured to cancel extraneous motion when extracting cardiopulmonary motion which can result in greater accuracy of the readings. Various embodiments of the system 100 can also, using algorithms such as DOA, separate and monitor or measure secondary or multiple cardiopulmonary motion sources (e.g., cardiopulmonary motion of a second or multiple subjects nearby can be reported simultaneously). Various embodiments of the system 100 can also, using algorithms such as DOA, separate and suppress secondary or multiple cardiopulmonary motion sources (e.g., cardiopulmonary motion of a second or multiple subjects nearby can be suppressed such that only the intended subject is measured). Various embodiments of the system 100 can include a radio frequency identification (RFID) tag in conjunction with DOA to enable tracking of the desired subject.

Various embodiments described herein can implement various approaches for motion compensation such as empirical mode decomposition (EMD), suppression of secondary motion sources with direction of arrival (DOA) processing, blind signal separation (BSS), independent component analysis (ICA), suppression of motion in the direction of high-frequency received signals, or any combination thereof.

Various embodiments of the system 100 can include radio frequency identification (RFID) tag configured to enable positive identification of a monitored subject. Various embodiments of the system 100 can be adapted to have various sizes, form factors and physical dimensions suitable for including in a bedside unit, a hand held unit, in a PDA, in a smart phone, in a tablet computer, a module as part of larger medical system, etc. Various embodiments of the system 100 can include one or more outputs such that information can be viewed and controlled either locally or remotely. In various embodiments, the system 100 can be a thin client application such that the system 100 can include the sensor, data acquisition, and communications, and demodulation, processing, and output systems would be in another device. For example, in some embodiments, the system 100 can be provided to a network system where controls and processing are centralized for a network of sensors and the sensor and networking/communications part is onsite, near the subject. In some embodiments, the system 100 can automate the initiation of measurements under certain predefined circumstances, e.g., when person is detected in a room, at set time intervals, etc. In various embodiments, the system 100 can be used to perform non-contact measurement of depth of breath and relative tidal volume or absolute tidal volume. Various embodiments of the system 100 can be used as a cardiopulmonary and/or activity monitor.

In various embodiments of the system 100, the signal conditioning does not include high-pass filtering, DC-blocking or DC-cancellation hardware, and the DC offsets are acquired along with the signal, and removed in software. In some embodiments, a two-operation method can be used to suppress the DC component in a signal, in which the first operation concerns the removal of the static DC offset due to the circuit, while the second operation addresses the suppression of the time-varying DC offset due to the clutter, temperature and other factors. In some embodiments, in the first operation, an estimate of the DC offset is determined by various methods including, but not limited to, using the value of the first sample acquired, the mean of the first few samples, or the mean of the first frame. In other embodiments, the DC offset can be measured during calibration at the factory, and this factory value can be subtracted from each frame. In some embodiments, the estimated DC offset is subtracted from the signal prior to demodulation. In some embodiments utilizing quadrature receivers, different values can be calculated and subtracted for each quadrature channel. In some embodiments, the same DC offset can be subtracted from every sample and/or every frame of the signal. In some embodiments utilizing frame-based processing, the second operation can deduce and suppress a DC estimate from every demodulated frame by using the value of the first sample in the frame or the mean of the samples in the frame and suppressing the DC offset by subtracting this value from that frame before further processing. In some embodiments, a band-limited signal can be reconstructed from the zero-mean frames by compensating for the discontinuity across consecutive frames. In some embodiments, discontinuity compensation uses the last sample of the previous frame and the first sample from the current frame, and then adds a constant value to the samples in the current frame such that the difference between the values of the samples specified earlier is close to zero. In some embodiments, the second operation can apply a high-pass filter to the signal after it has been conditioned with the coarse estimate of the DC offset subtraction in the first operation. In some embodiments, the high pass filter can be applied to the signal prior to demodulation; in other embodiments, the high-pass filter can be applied to the signal after demodulation. In various embodiments, the cut-off frequency of the high-pass filter can be adjusted to meet signal requirements. In some embodiments, this cut off frequency can be between approximately 0.01 Hz and 0.1 Hz. In some embodiments, the high-pass filter cutoff can be determined adaptively, such that it is as high as suitable for a given respiratory rate. In various embodiments, the high pass filter can be implemented either as a finite impulse response filter (FIR) or an infinite impulse response filter (IIR).

Figure 6A:
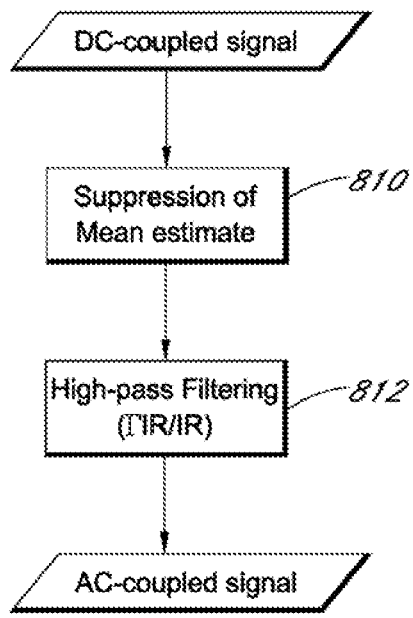
FIGS. 6A and 6B illustrate flowcharts of embodiments of a method of performing DC compensation.

An embodiment of a method for DC compensation is shown in FIG. 6A. As illustrated in FIG. 6A, the DC-coupled signal can have the mean suppressed as shown in block 810, and then high-pass filtered as shown in block 812 to generate an AC-coupled signal.

Figure 6B:
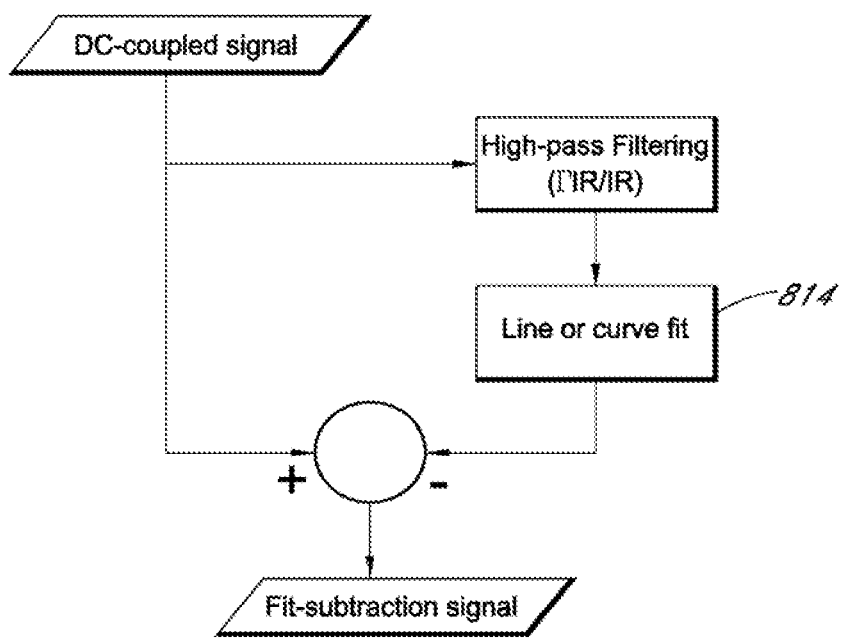

In some embodiments, high-pass filtering the signal can be optional and, instead of high-pass filtering, the signal fitted line or curve can be subtracted. FIG. 6B illustrates a flow chart of an embodiment of a method for DC compensation in which high-pass filtering is optional. In the method illustrated by FIG. 6A, a curve-fitting or line-fitting and subtraction algorithm can be used with a preset amount of recorded data. In various embodiments, the duration of the recorded data can be 15 seconds, 30 seconds, 60 seconds or some other duration. The method can comprise fitting the raw signal, or the signal after the rough DC estimate is removed, or the signal after high-pass filtering to a line or curve as shown in block 814. The fitted line can be subtracted from the signal, removing the slowly-varying DC offset to obtain a fit-subtraction signal. In various embodiments, this fit-subtraction can be obtained before demodulation, and can be applied to the I and Q signals individually. In some other embodiments, this fit-subtraction can be obtained after demodulation. In some embodiments, the signal can be fit to a line as shown by trace 816 of FIG. 6C. In some embodiments, the signal can be fit to a quadratic polynomial or parametric curve, as shown by trace 818 of FIG. 6C.

Figure 6D:
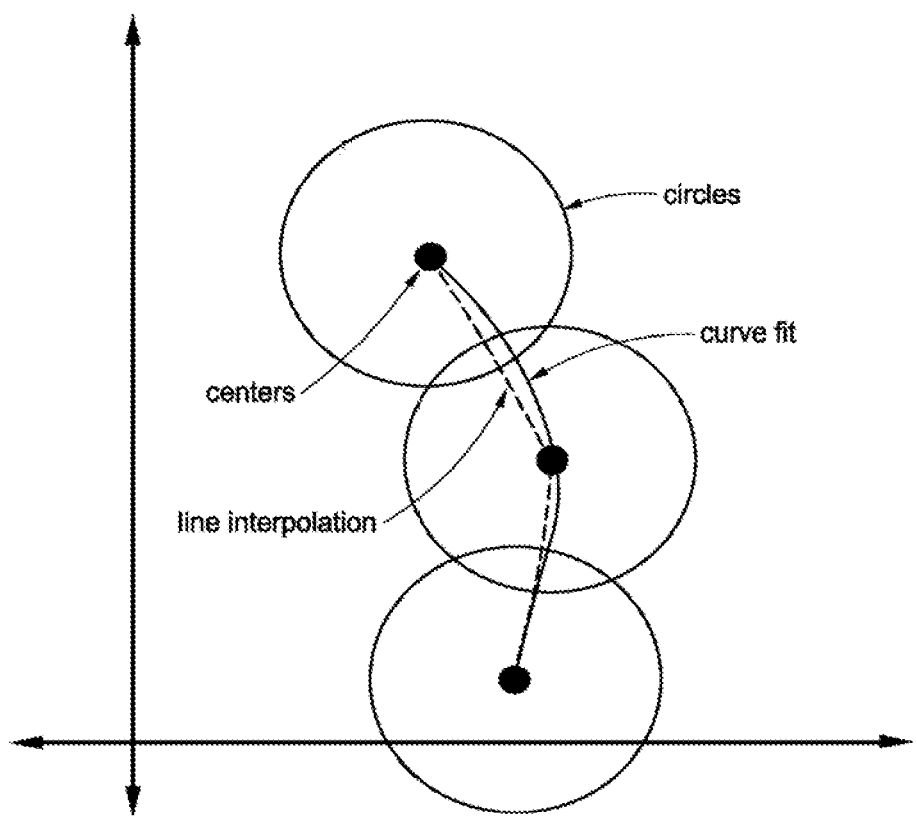
FIG. 6D illustrates a demodulation algorithm utilizing a circle-find or an arc-find function.

In some embodiments, demodulation can involve an arctangent-based demodulation algorithm utilizing a circle-find or arc-find function, which can provide a center and/or a radius as shown in FIG. 6D. In some embodiments utilizing arctangent-based demodulation, the center can be used as the reference point and used to find the phase change generated as an object moves back and forth in space. In some embodiments, the movement of the arc-center can be tracked over time. In some embodiments, the tracked center over time can be fit to a curve which is subtracted in 2 dimensions. In some embodiments, the path can be interpolated between time tracked center key points. In some embodiments, the change in the radius can be tracked over time. In some embodiments, DC offset compensation such as, but not limited to, AC coupling, first sample subtraction, mean value subtraction, or any combination thereof can be utilized after arc-tangent demodulation. In some embodiments, the tracking circle-find algorithm is used instead of another DC offset compensation method. In various embodiments, center-tracking can replace the first operation, the second operation or the first and second operations of the previously described two-operation DC-offset compensation algorithm.

In the system 100, deviation of the phase can be proportional to the chest motion divided by the wavelength of the carrier signal, and the amplitude of the signal may not be significantly affected by chest motion, such that when the phase is plotted in the I/Q plane, the I/Q constellation is distributed along an arc of a circle or a full circle. In embodiments in which the chest motion is small compared to the signal's wavelength, the arc can sweep a small portion of the circle, such that it can be approximated by a line, and the phase can be demodulated through linear methods. Alternatively, if the chest motion is large compared with the carrier signal's wavelength, the I/Q constellation samples can be distributed on a larger arc that cannot be approximated by a line. In some embodiments in which the transceiver operates at approximately 5.8 GHz, when the chest motion due to the respiration is approximately 0.5 cm, the phase deviation due to the chest motion can be approximately 70°; a 70° arc may not be accurately approximated as a line in the complex constellation. In these embodiments, non-linear demodulation based on arctangent function can extract phase information directly from arc-distributed samples.

In various embodiments, the quadrature signals can be demodulated using any of several algorithms, including but not limited to linear demodulation, arc-based demodulation algorithm (e.g., arc-tangent demodulation with center tracking), non-linear demodulation algorithm, or any combination thereof. Demodulation algorithms can include any of the following methods, but not limited to, projecting the signal in the complex plane on a best-fit line, projecting the signal in the complex plane on the principal eigenvector, aligning the signal arc to a best-fit circle and using the circle parameters to extract angular information from the signal arc, or any combination thereof. Linear demodulation can use any of many algorithms, including projecting the signal in the complex plane on the principal eigenvector, projecting the signal on the best-fit line, or any combination thereof. Arctangent demodulation can extract phase information which is corresponding to the chest motion associated with cardiopulmonary activity as described herein. In quadrature systems, data collected by two orthogonal channels (e.g., In-phase (I) and quadrature phase (Q)) can lie on a circle centered at a DC vector of the channels. After tracking center vector of the corresponding circle and subtracting it from the data samples, phase information of received signal can be extracted through an arctangent function.

In some embodiments, linear demodulation is the projection of the signal on a linear vector. In some embodiments, the signal can be rotated until a maximal projection on the x or y plane is achieved. In some embodiments, a best fit line can be estimated, and the data can be projected on the best-fit line. In some embodiments, specific key points, such as the end points of an arc, can be connected to form a line, and the signal can be projected on this line. In some embodiments, the signal can be projected on the line that provides the most variance in the signal.

In some embodiments, the hardware can be used in conjunction with the software to enable linear demodulation. In some embodiments, the carrier radio frequency can be adjusted with a phase-locked-loop and/or another method to put one of the channels in the null, such that most of the signal is on the other channel; the signal in the non-null channel is used. In some embodiments, a phase-shifter in the RF circuit can be tuned to a point where one channel is in the null, and the signal on the other channel can be used.

Figure 7:
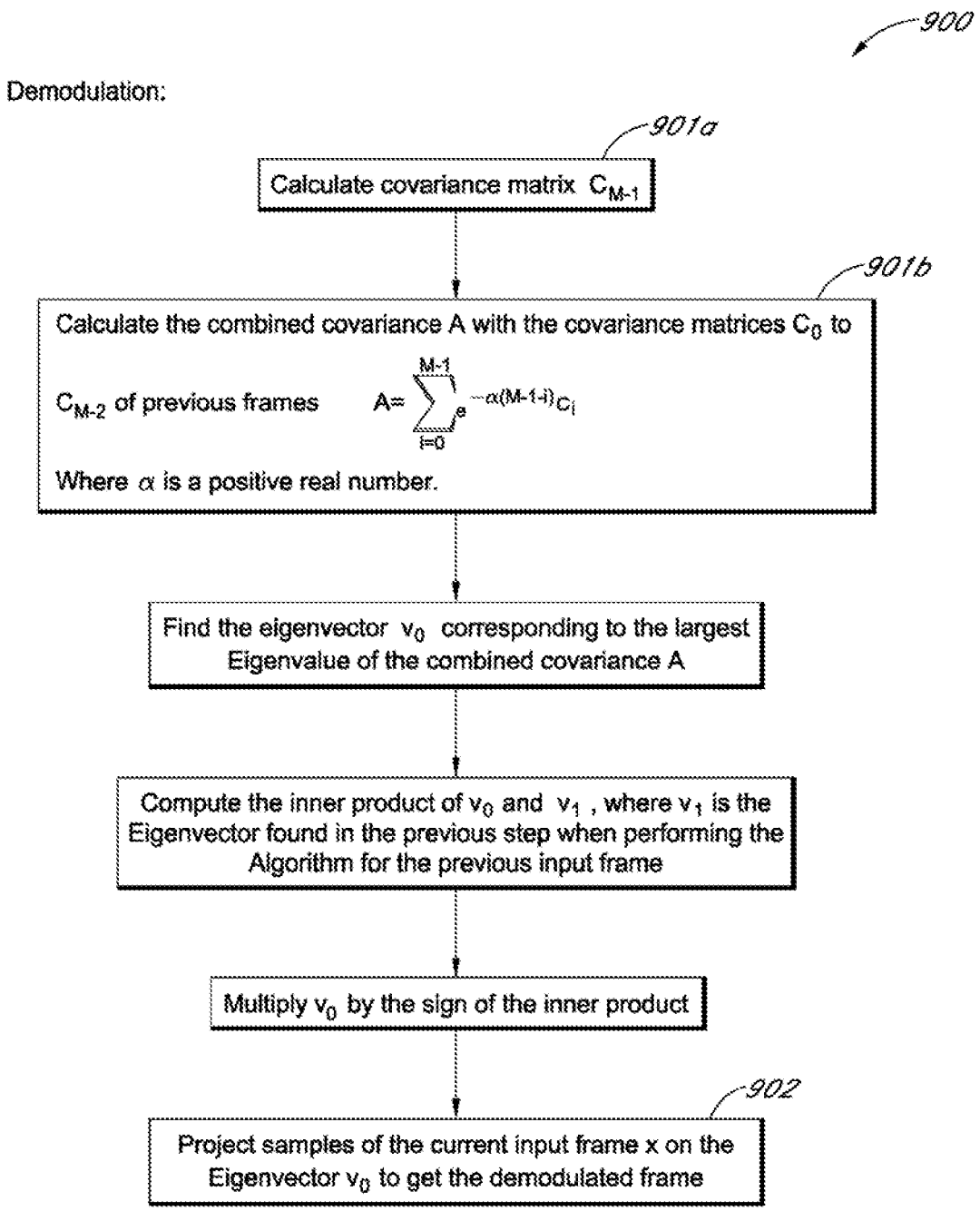
FIG. 7 illustrates an embodiment of a linear demodulation algorithm.

An embodiment of a linear demodulation algorithm is further described below and illustrated in FIG. 7. In one embodiment, the algorithm comprises computing covariance matrices for a subset of input frames as shown in block 901a including the most recent frame and projecting the data on a primary vector or an eigenvector of said covariance matrix as shown in block 902. If it is determined that the current eigenvector is in a reverse direction as compared to a previously determined eigenvector then the algorithm can rotate the current eigenvector by 180 degrees.

In various embodiments, the linear demodulation algorithm can comprise one or more of the following operations:
1. Compute covariance matrix $C_{M-1}$ of the current input frame x as shown in block 901a.
2. Based on $C_{M-1}$ and covariance matrices $C_0$ to $C_{M-2}$ of previous frames, compute an A-matrix as shown in block 901b represented by the equation:

$$A = \sum_{i=0}^{M-1} e^{-\alpha \cdot (M-1-i)} C_i$$

In this equation, $\alpha$ can correspond to a damping factor and can be a positive real number. In various embodiments, the value of $\alpha$ can range from approximately 0.1 to approximately 0.5. In one embodiment, $\alpha$ can be approximately 0.2. M can correspond to the number of frames in the buffer and can range from about 2 to 15. In one embodiment, M can be 10.
3. Find the primary vector or eigenvector $v_0$ corresponding to the largest primary value or eigenvalue of A as shown in block 901c.
4. Compute the inner product of $v_0$ and $v_1$, where $v_1$ can represent the eigenvector found in operation 3 when performing the algorithm for the previous input frame as shown in block 901d.
5. Multiply $v_0$ by the sign of the inner product found in operation 4 as shown in block 901e.
6. Project samples of the current input frame x on the eigenvector $v_0$ calculated in operation 5 to get the demodulated frame as shown in block 902.

If a target's periodic physiological motion variation is represented by x(t), and the wavelength of the radar signal is represented by $\lambda$, the quadrature baseband output, assuming balanced channels, can be expressed as:

$$B(t) = A_r \exp\left(i * \left(\theta + \frac{4\pi \Delta x(t)}{\lambda}\right)\right) + DC$$

In this equation, DC can be a complex number representing the non-time-varying voltage values of the I and Q channels, $\theta$ can represent the constant phase shift due to the transceiver architecture and target range, and Ar can represent the amplitude of the baseband signal. From (1), it will be appreciated that if DC, which can come from clutter, intra-circuit reflection, and self-mixing is estimated and removed, the angle deviation, which can be linearly proportional to actual physical motion of a target x(t), can be extracted simply by the arctangent function. However, if the low-frequency or direct-current component of the phase shift caused by x(t) is removed, or if DC is not removed, arctangent demodulation can be more complicated and is not straightforward.

In some embodiments, the arc can be segmented (divided into sections), and the intersection of the perpendicular vectors of the sections is used to give an estimate of the center using a least mean square error, maximum likelihood estimation, or other method. In some embodiments, the end points of an arc can define a chord of a circle, and the normal vector at the midpoint of the chord can be defined as the perpendicular axis of the arc; segments along the arc each have a normal vector, which intersects the arc's perpendicular axis at the center point. In some embodiments, the mean, midpoint or median of the intersect points along the perpendicular axis can be defined as the center of the arc. In some embodiments, intersection outliers along the axis can be removed before the center-estimation algorithm is applied. In some embodiments, a line fit can be performed to find the perpendicular axis of the arc, which intersects the midpoint between the end points.

In some embodiments where the carrier wavelength is shorter than the displacement of the chest, such that a complete circle is formed in the I/Q plane, the center can be found by a best fit circle, center of mass, geometrical center, 2D low-pass filter with peak-finding, look-up table fitting the data to a variety of circles, or any combination thereof.

In some embodiments, demodulation can be performed in real-time as the center is estimated. In some embodiments, demodulation can be performed retrospectively for an optimal center from a built up buffer in memory. In some embodiments, the center can be tracked periodically over time and fit to a line, quadratic curve, geometric shape, polynomial interpolation, or any combination thereof and used as moving center during demodulation.

Figure 9A:
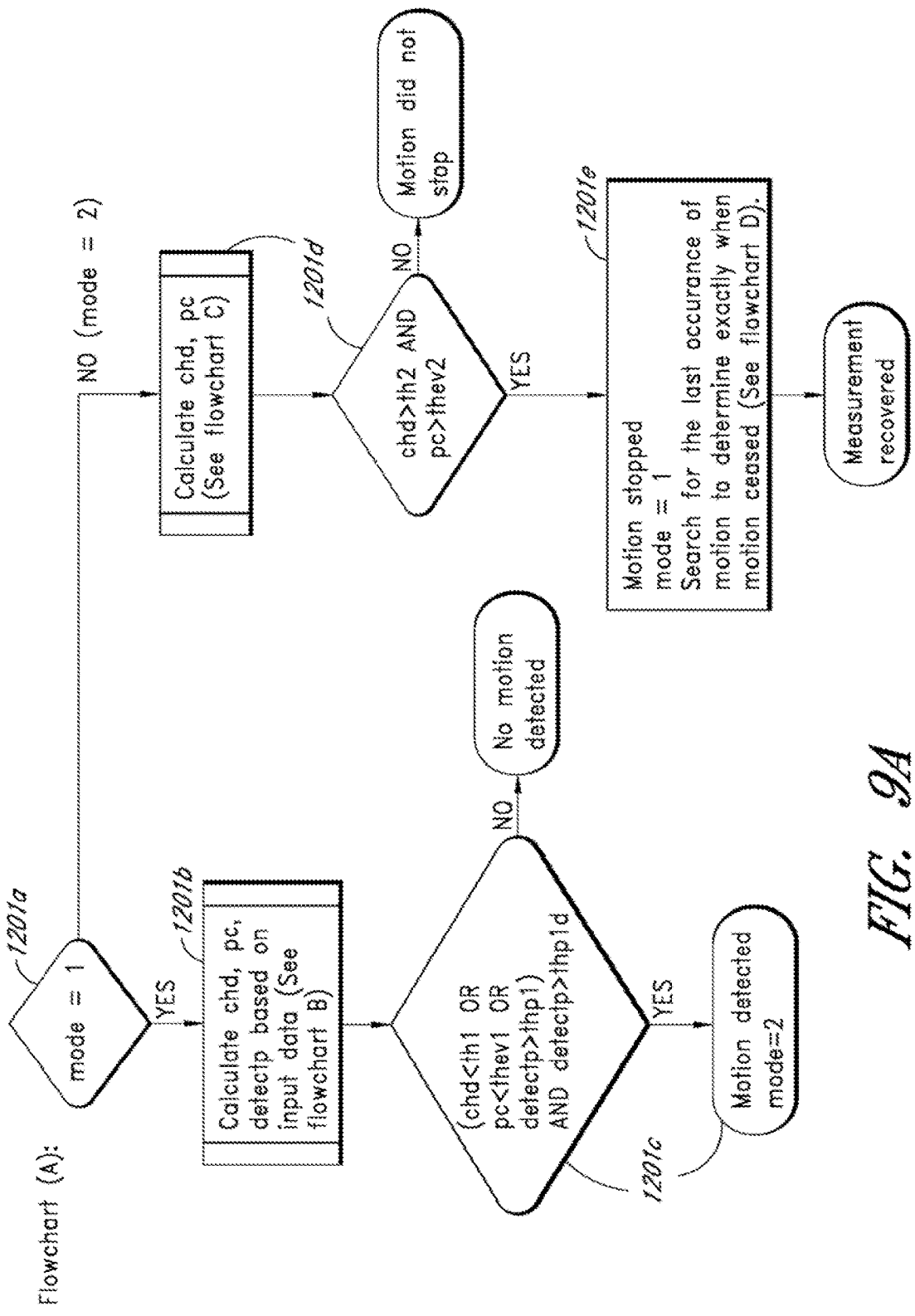
FIGS. 9A-9D illustrate an embodiment of a method configured to detect non-cardiopulmonary motion.
Figure 9B:
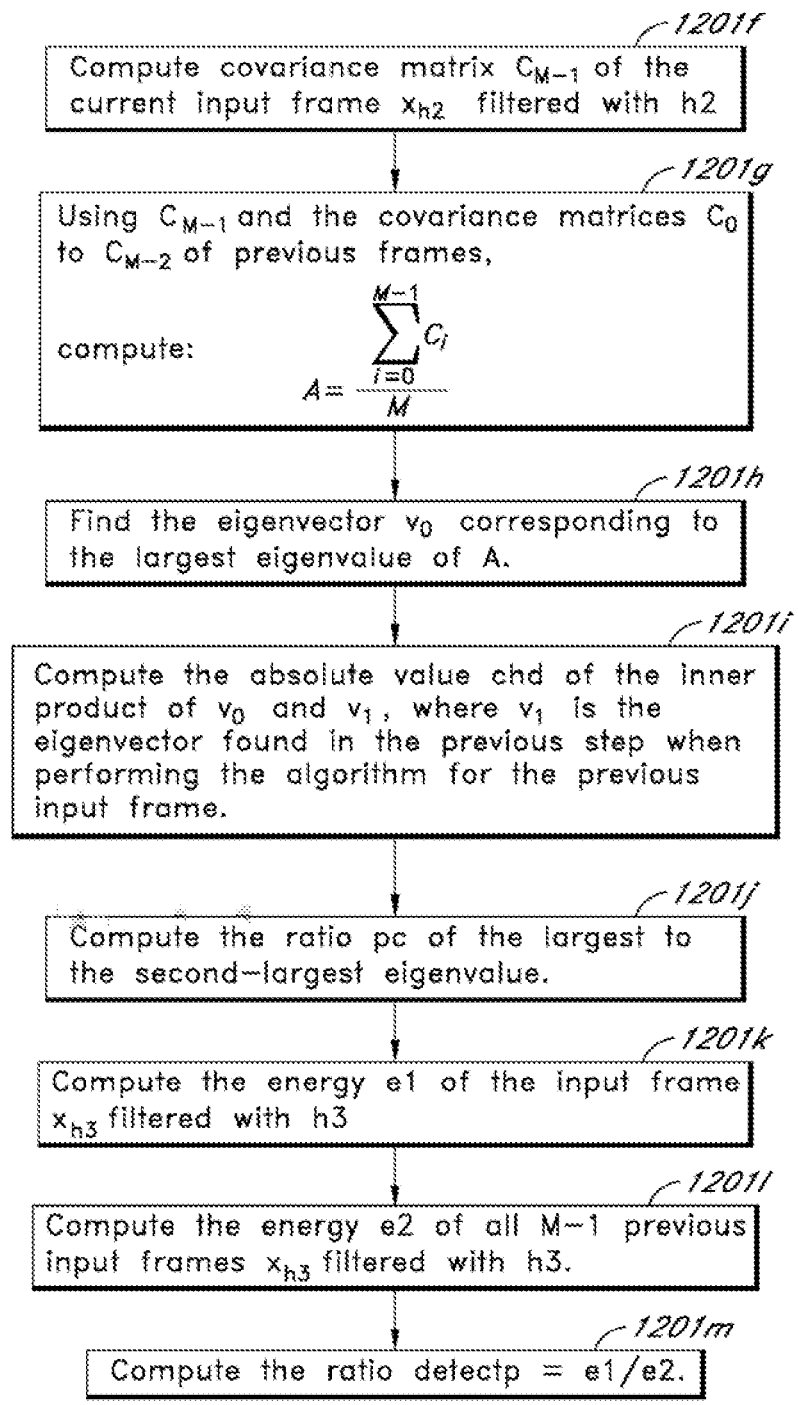
Figure 9C:
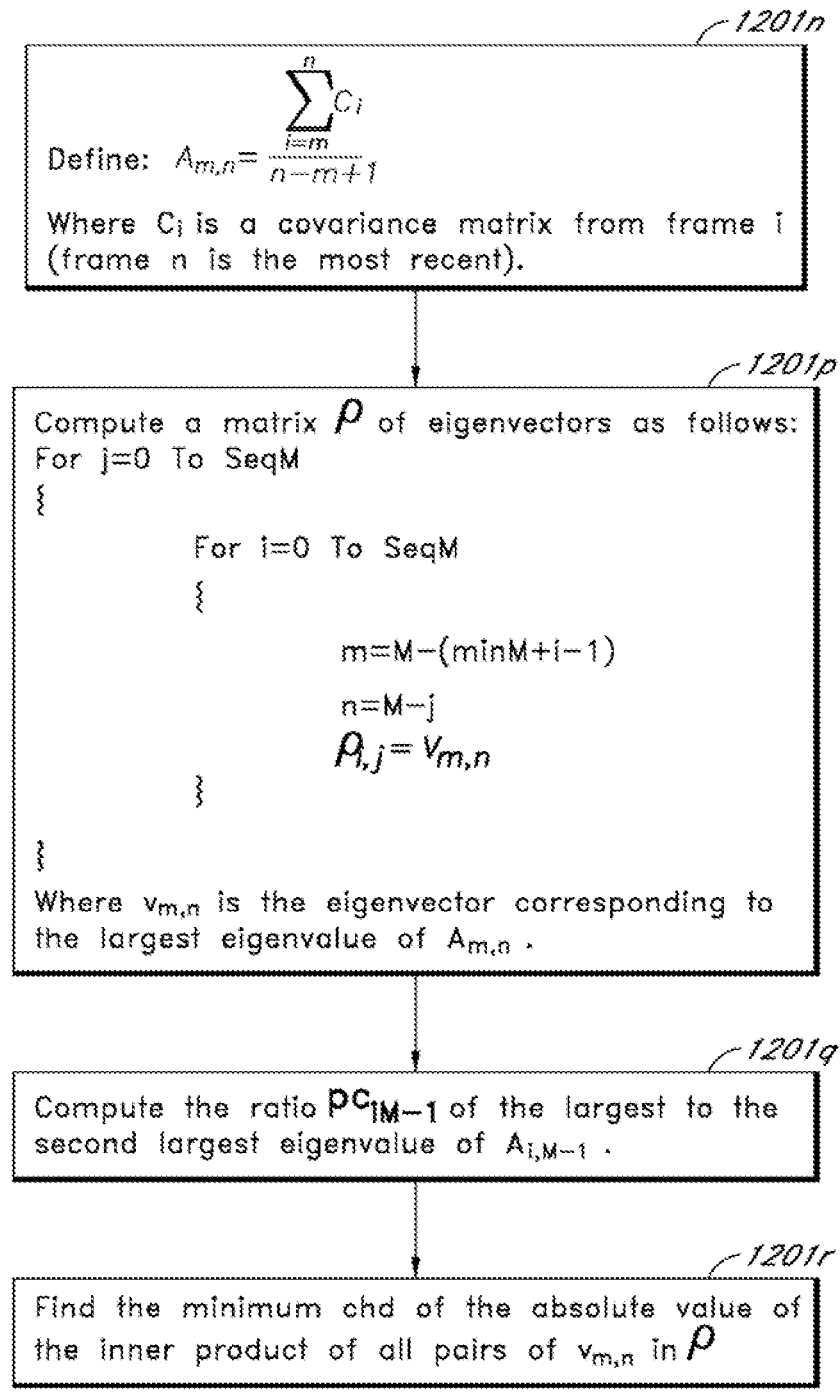
Figure 9D:
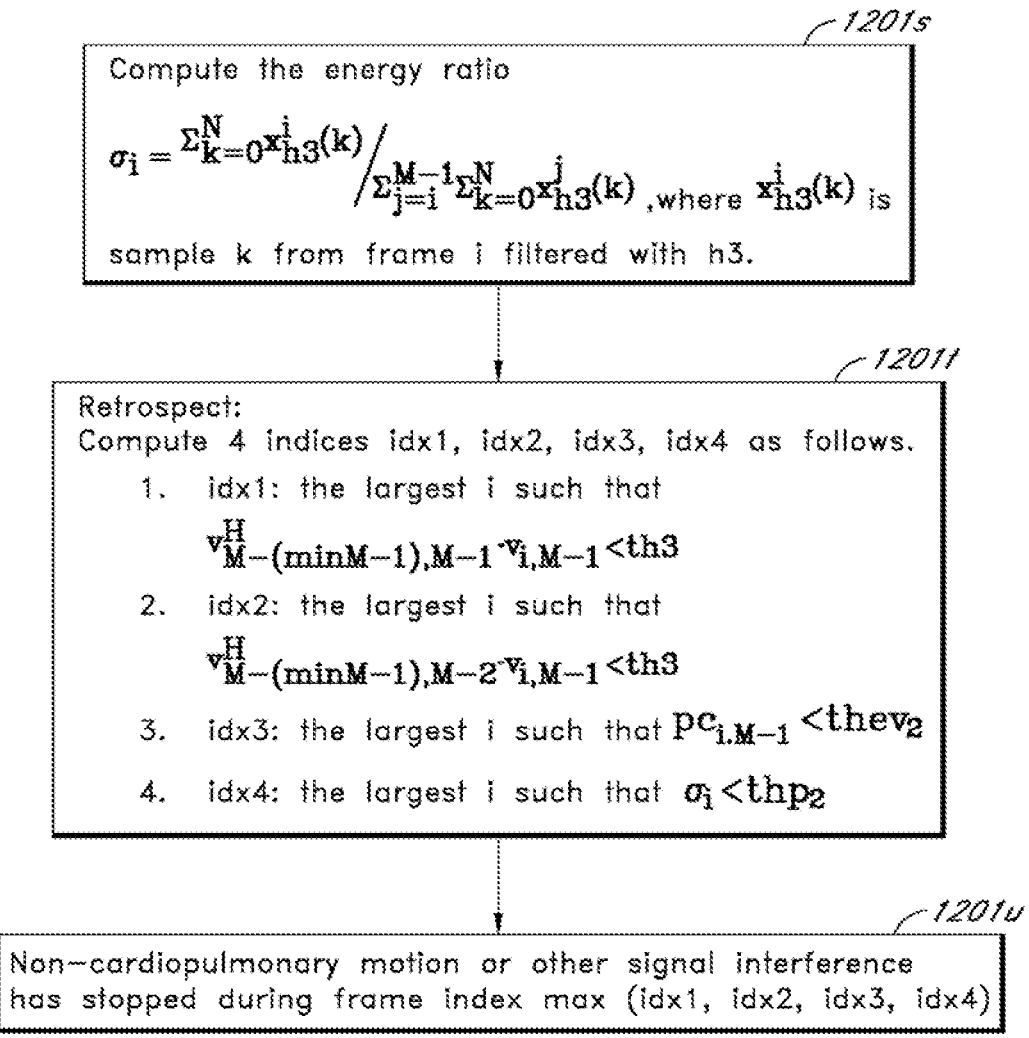
Figure 10A:
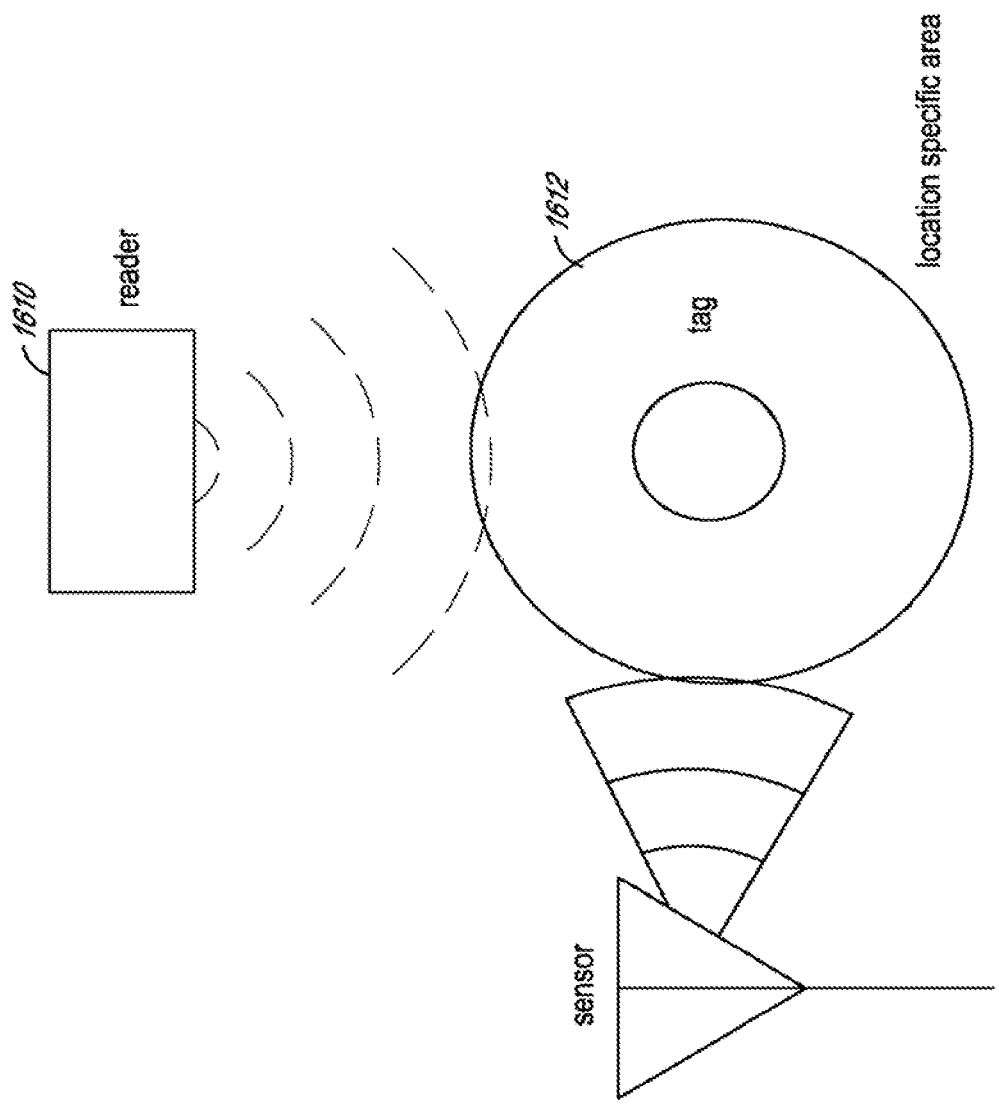
FIGS. 10A-10D illustrate various embodiments of an identification system configured to provide positive patient identification in conjunction with remote vital signal sensing.
Figure 10B:
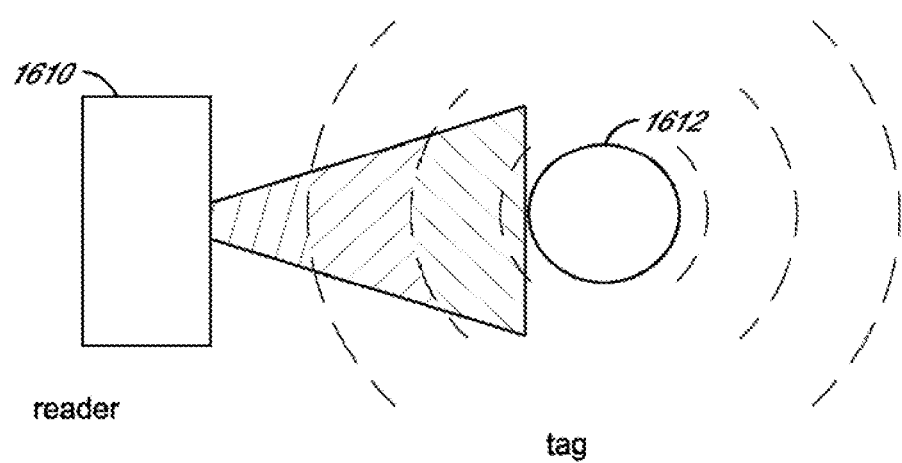
Figure 10C:
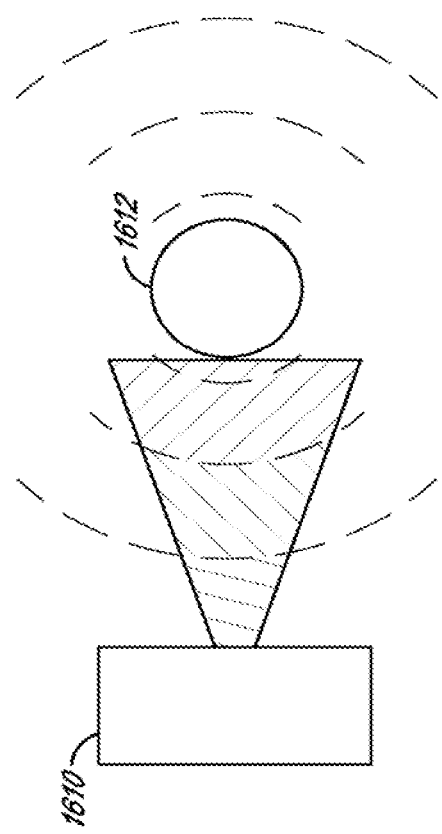
Figure 10C:
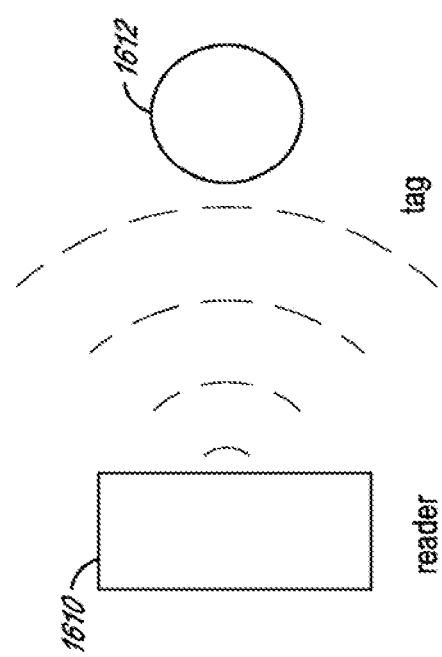
Figure 10D:
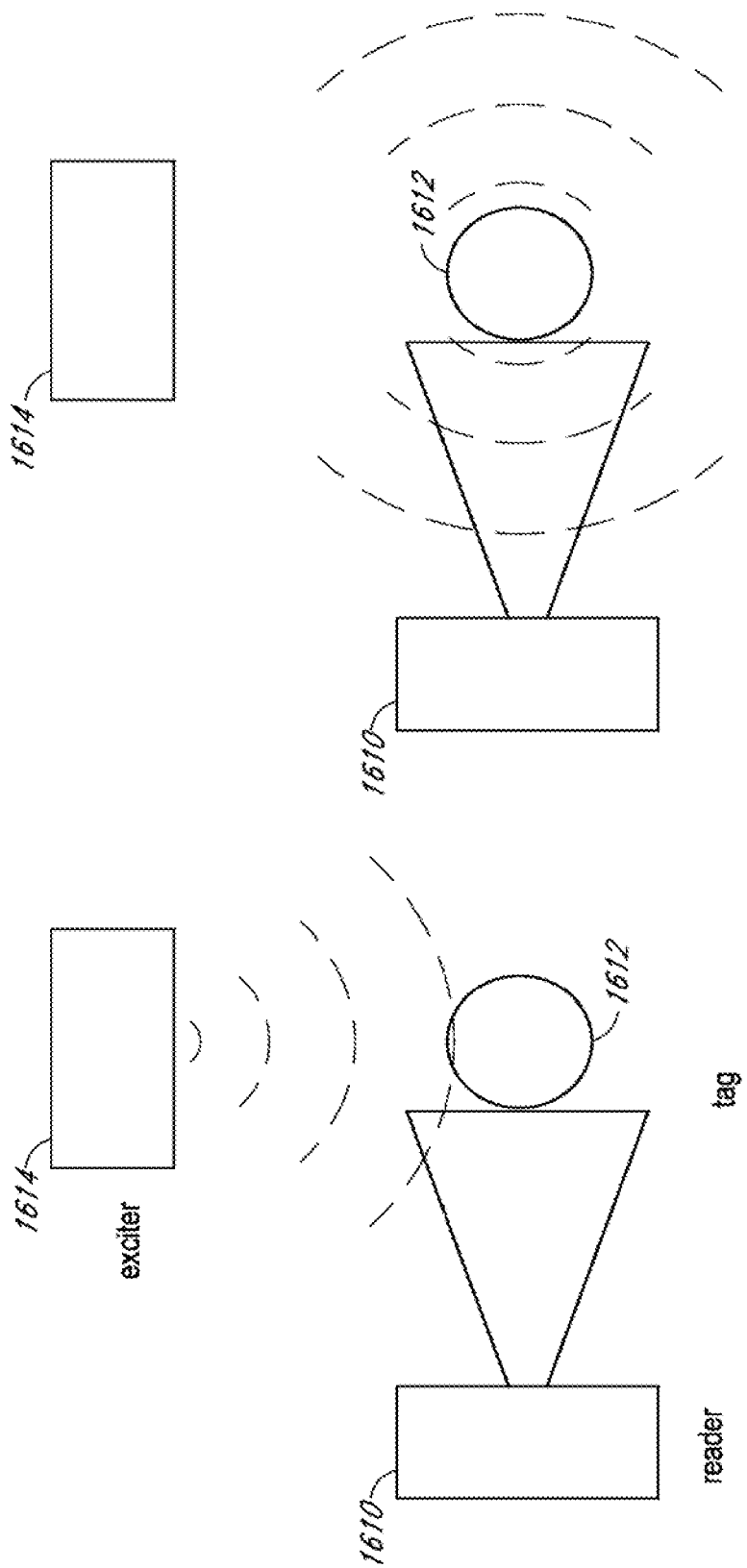
Figure 10E:
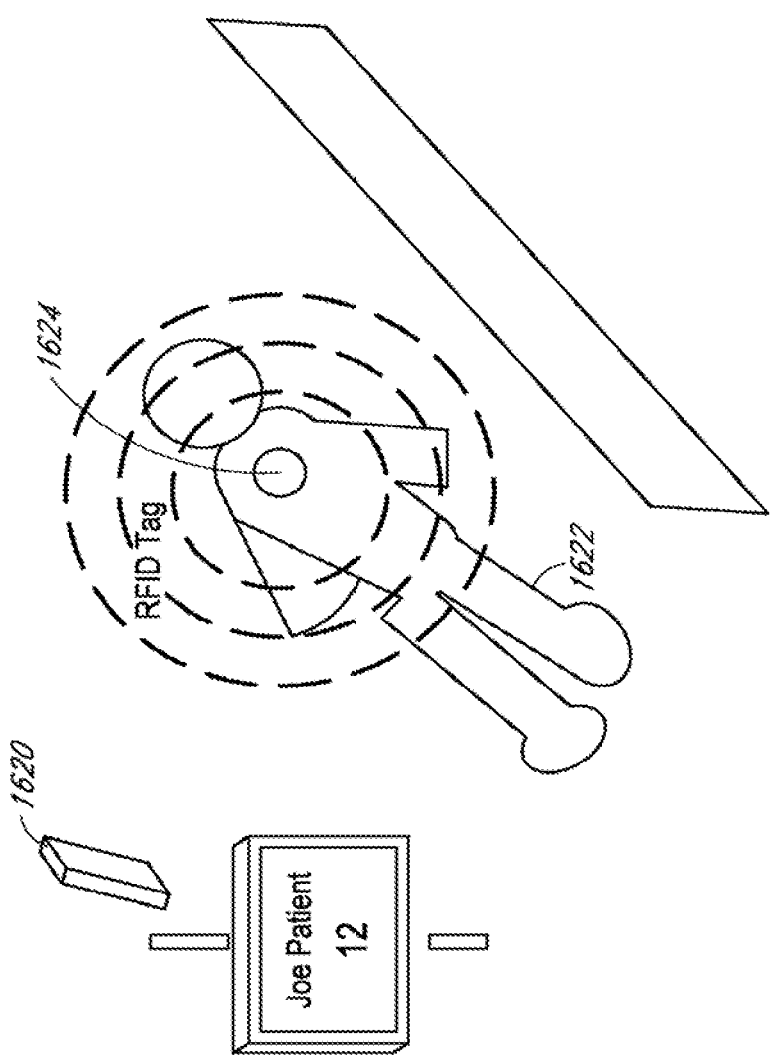
FIG. 10E illustrates a system configured to enabling positive identification using a tag attached to the patient.
Figure 10F:
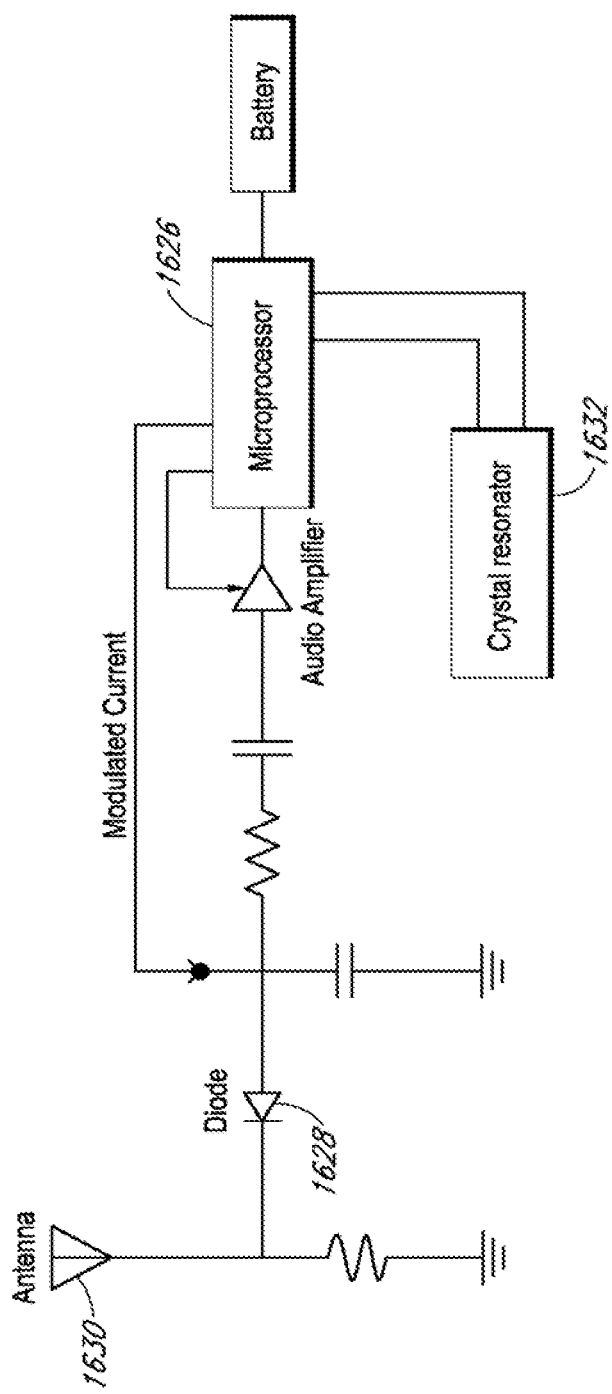
FIG. 10F schematically illustrates an embodiment of a passive transponder RFID technology.
Figure 10G:
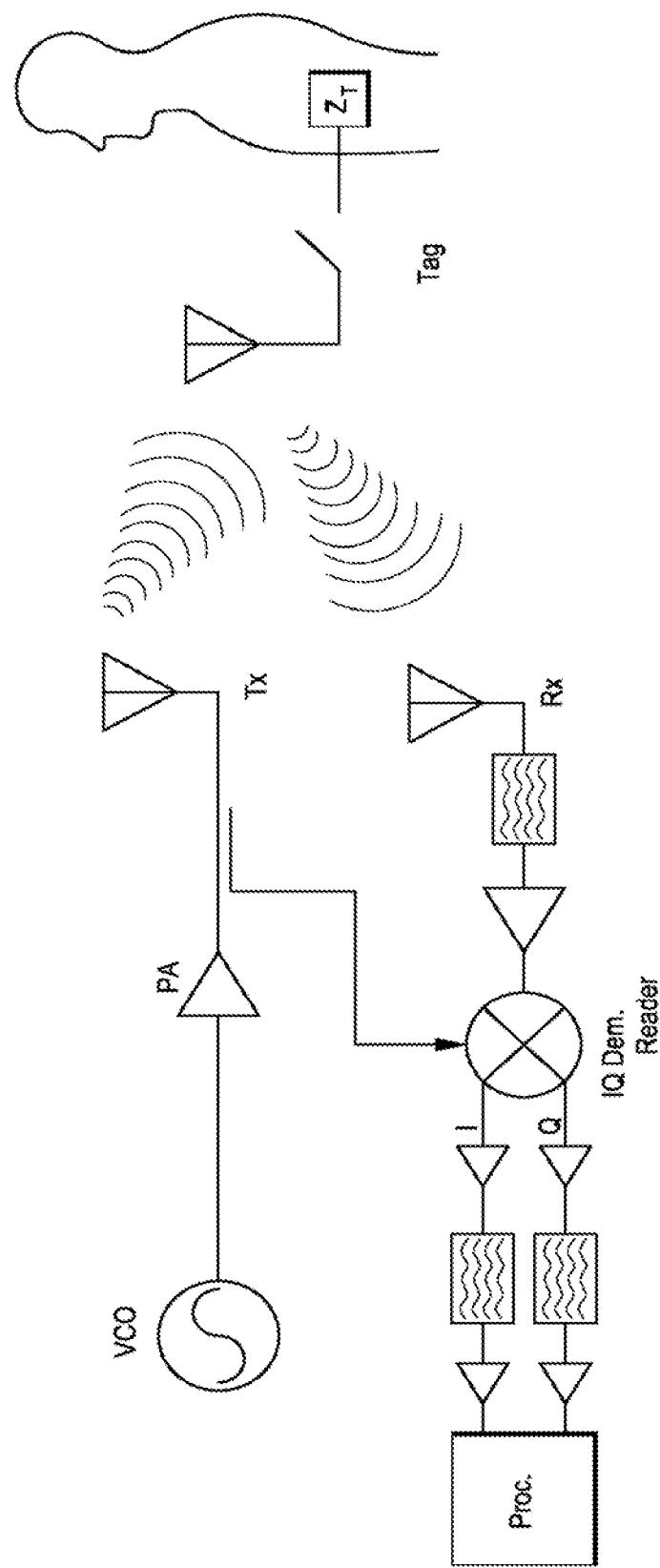
FIG. 10G schematically illustrates an embodiment of a Doppler respiratory and identification reader.
Figure 10H:
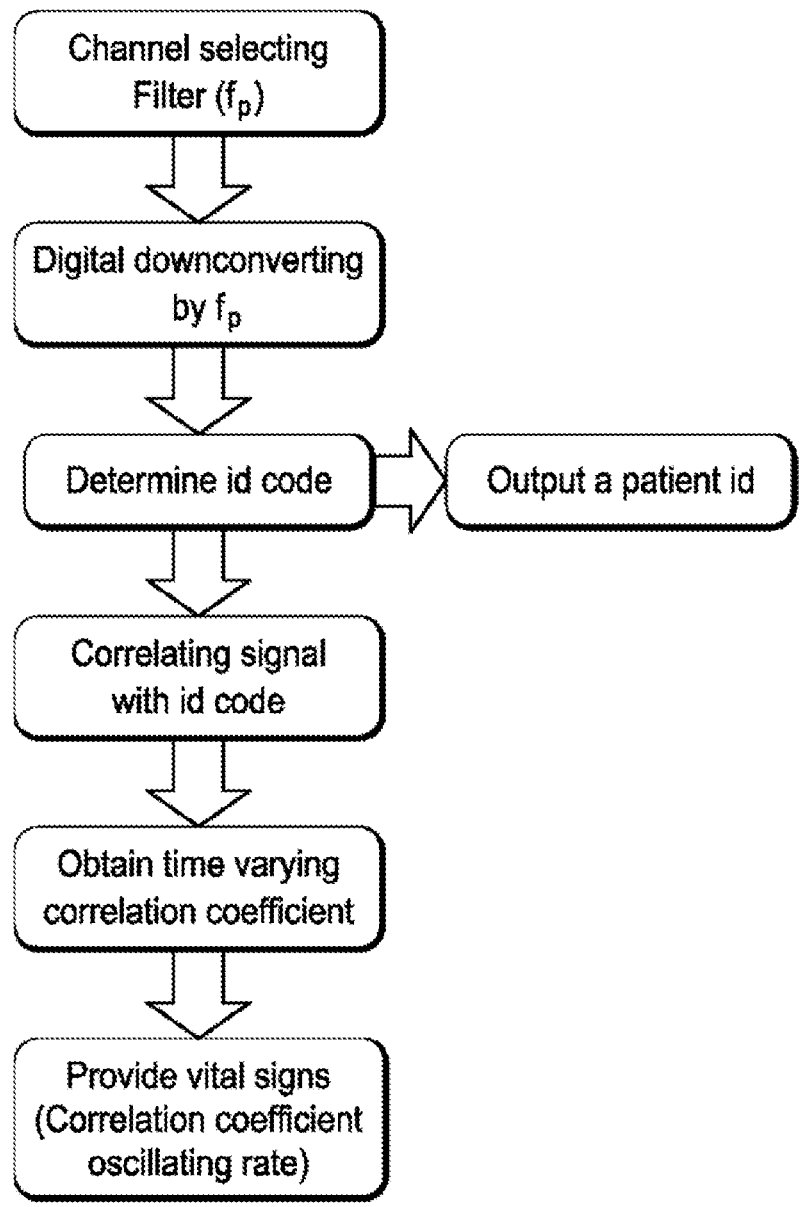
FIG. 10H illustrates an embodiment of a method of identification reading and vital signs signals processing of the sideband signals.
Figure 11:
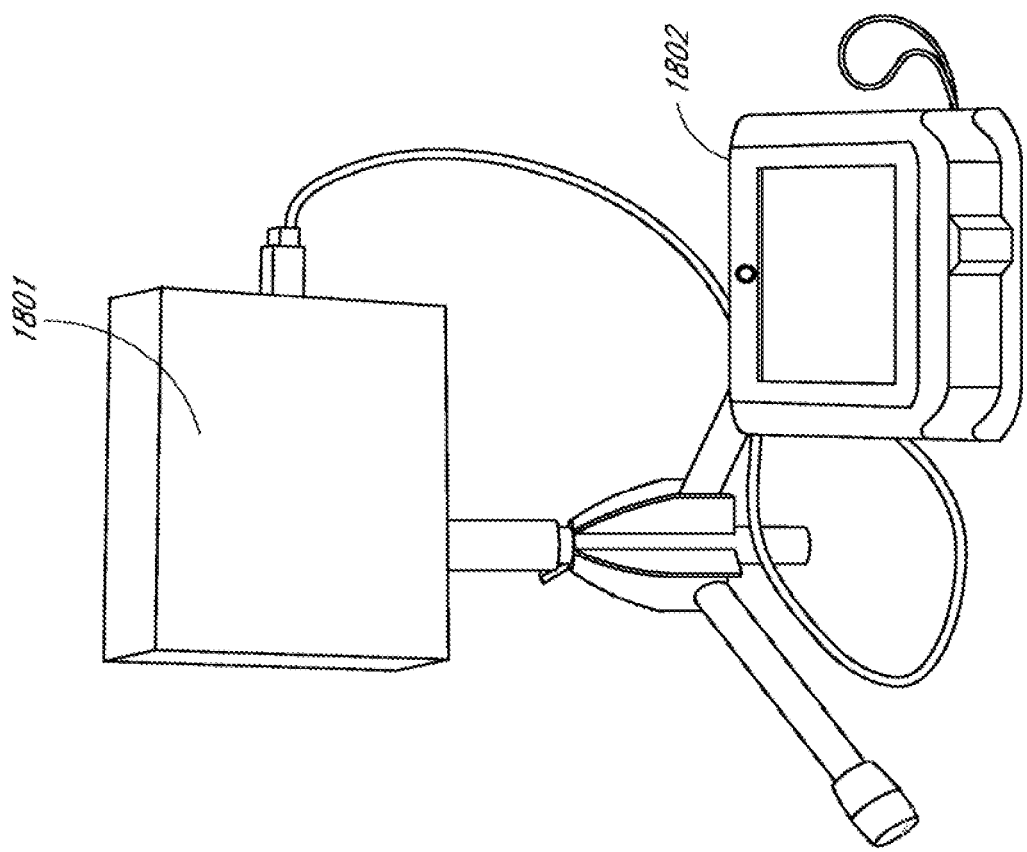
FIG. 11 illustrates an embodiment of the radar-based physiological motion sensor comprising a sensor unit, a computational unit and a display unit.
Figure 12:
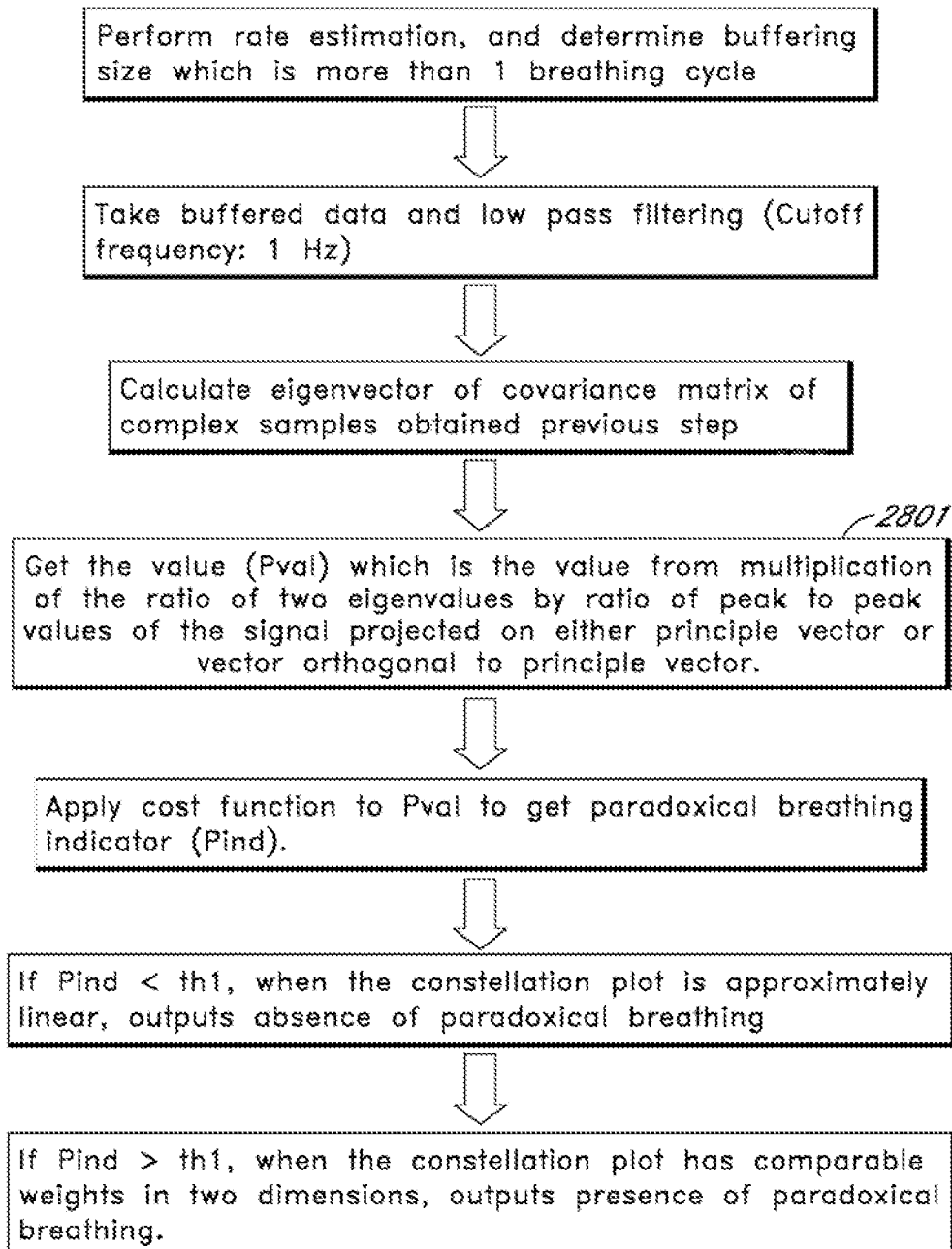
FIG. 12 illustrates an embodiment of a method to determine a paradoxical breathing indicator.

An example of a non-cardiopulmonary motion detection algorithm is further described below and illustrated in FIGS. 9A-9D. The algorithm can be executed by one or more processors and can detect non-cardiopulmonary motion and/or other signal interference by looking at the change in direction of the eigenvectors, the ratio of the eigenvalues and the change of energy in the signal, as shown in block 1201b. As illustrated in FIG. 9A, the algorithm can start in mode 1, as shown in block 1201a, by assuming that no non-cardiopulmonary motion and/or other signal interference is present and can switch to mode 2 as shown in block 1201c in response to detecting any non-cardiopulmonary motion and/or other signal interference. When in mode 2, the algorithm can similarly check the change in direction of the eigenvectors and the ratio of eigenvalues, as shown in block 1201a to determine if the non-cardiopulmonary motion and/or other signal interference has ceased. If motion ceases, then the algorithm can find the earliest time (the retrospect) with no motion, as shown in block 1201e. The algorithm can comprise one or more of the following operations:

1. Mode=1
   a. Compute covariance matrix $C_{M-1}$ of the current input frame $x_{h2}$ filtered with a first filter having a filter function h2, as shown in block 1201f of FIG. 9B. In some embodiments, the first filter can be a low-pass filter.
   b. Using $C_{M-1}$ and the covariance matrices $C_0$ to $C_{M-2}$ of previous frames, compute an A-matrix $$A = \frac{\sum_{i=0}^{M-1} C_i}{M},$$

as shown in block 1201g of FIG. 9B, where M can represent the number of preceding frames to consider and in some embodiments M can be 32. In various embodiments M can be larger or smaller than 32.
   c. Find the eigenvector $v_0$ corresponding to the largest eigenvalue of A, as shown in block 1201h of FIG. 9B.
   d. Compute the absolute value chd of the inner product of $v_0$ and $v_1$, where $v_1$ is the eigenvector found in operation c when performing the algorithm for the previous input frame, as shown in block 1201i of FIG. 9B.
   e. Compute the ratio pc of the largest to the second-largest eigenvalue, as shown in block 1201j of FIG. 9B.
   f. Compute the energy $e_1$ of the input frame $x_3$ filtered with a second filter having a filter function h3. In various embodiments, the second filter can be a high-pass filter, as shown in block 1201k of FIG. 9B.
   g. Compute the average energy per frame $e_2$ of all M−1 previous input frames $x_3$ filtered with h3, as shown in block 1201l of FIG. 9B.
   h. Compute the ratio detectp=$e_1/e_2$, as shown in block 1201m of FIG. 9B.
   i. If (chd<th1 OR pc<thev1 OR detectp>thp1) AND detectp>thp1d), as shown in block 1201b and 1201c then non-cardiopulmonary motion or other signal interference is detected, switch to Mode=2. In various embodiments th1 can have a value between approximately 0.6 and approximately 1. In various embodiments, thev1 can have a value in the ranging from about 4 to 12. In various embodiments, thp1 can have a value ranging from about 4 to 20. In various embodiments, thp1d can have a value between approximately 0.1 and approximately 0.8.
2. Mode=2
   a. Calculate an A'-matrix represented by the equation $$A_{m,n} = \frac{\sum_{i=m}^{n} C_i}{n - m + 1},$$

where $C_i$ can represent a covariance matrix from frame i (frame n being the most recent), as shown in block 1201n of FIG. 9C.
   b. Compute a matrix p of eigenvectors as follows, as shown in block 1201p of FIG. 9C:

```
For j = 0 To SeqM
{
    For i = 0 To SeqM
    {
        i. m = M − (minM + i − 1)
        ii. n = M − j
        iii. ρ_{i,j} = v_{m,n}
    }
}
```

$$\rho = \begin{bmatrix} v_{M-(minM-1),M-1} & \cdots & v_{M-(minM-1),M-SeqM} \\ \vdots & \ddots & \vdots \\ v_{M-(minM-SeqM-1),M-1} & \cdots & v_{M-(minM-SeqM-1),M-SeqM} \end{bmatrix},$$

where SeqM can be about 5 in some embodiments and can correspond to the number of preceding frames to consider, where minM can represent the number of frames prior to current frame to consider and can be about 8 in some embodiments, where $v_{m,n}$ can represent the eigenvector corresponding to the largest eigenvalue of $A_{m,n}$.

c. Compute the ratio $pc_{i,M-1}$ of the largest to the second largest eigenvalue of the matrix $A_{i,M-1}$, as shown in block 1201q of FIG. 9C.

d. Find the minimum chd of the absolute value of the inner product of all pairs of $v_{m,n}$ in ρ, as shown in block 1201r of FIG. 9C.

e. Compute the energy ratio $\sigma_i = \Sigma_{k=0}^{N} x_{h3}^i(k) / \Sigma_{j=i}^{M-1} \Sigma_{k=0}^{N} x_{h3}^j(k)$, where $x_{h3}^i(k)$ can represent sample k from frame i filtered with h3, as shown in block 1201s of FIG. 9D.

f. If (chd>th2 AND $pc_{M-(minM-1),M-1}$>thev2) then non-cardiopulmonary motion and/or other signal interference is indicated to have stopped, switch to Mode=1, as shown in blocks 1201d and 1201e of FIG. 9A. In various embodiments, th2 can have a value between approximately 0.6 and approximately 1. In various embodiments, thev2 can have a value between approximately 4 and approximately 12.

g. Retrospect: Compute 4 indices idx1, idx2, idx3, idx4 as follows, as shown in block 1201t.

idx1: the largest i such that $V_{M-(minM-1),M-1}^H \cdot V_{i,M-1}$<th3.

idx2: the largest i such that $V_{M-(minM-1),M-2}^H \cdot V_{i,M-1}$<th3.

idx3: the largest i such that $pc_{i,M-1}$<thev2.

idx4: the largest i such that $\sigma_i$<thp2.

In various embodiments, th3 can have a value between approximately 0.6 and approximately 1. In various embodiments, thp2 can have a value between approximately 4 and 12. In one embodiment, thp2 can be approximately 5. In one embodiment, th3 can be approximately 0.97.

h. Then, non-cardiopulmonary motion and/or other signal interference is indicated to have stopped during frame index max(idx1, idx2, idx3, idx4), as shown in block 1201u.

In various embodiments, empirical mode decomposition (EMD) algorithms can be used to isolate the signal from motion, including motion due to, but not limited to, non-cardiopulmonary motion by the subject, cardiopulmonary motion of one or more people other than the intended subject, non-cardiopulmonary motion of another person or other people, motion of other objects in the environment, motion of the radar system, or any combination thereof.

An example configuration includes a system 100 configured to operate at a radio frequency of approximately 5.8 GHz with a direct-conversion receiver and DC-offset cancellation. In various embodiments, the system 100 includes a single antenna to transmit radiation and a single antenna to receive radiation. In various embodiments, one or more antennas can be used to transmit and/or receive signals. In various embodiments, the system 100 can include one or more processors configured to execute an arc demodulation algorithm. In some of these embodiments, the one or more processors can execute computer-readable instructions stored in non-transitory memory to perform the algorithm.

II. Apnea Therapy Device

In various embodiments, the physiological motion sensor can include a non-contact vital signs monitoring device, such as a radar-based device that can be configured to detect paradoxical breathing (e.g., when the abdomen contracts as the rib cage expands and/or when the rib cage contracts as the abdomen expands). In some cases, during obstructive apnea paradoxical breathing can be exhibited, although paradoxical breathing may not indicate an airway obstruction. In various embodiments, an indication of paradoxical breathing and of the level of paradoxical breathing can be useful in detecting obstructive apnea. While the following description may be described with reference to apnea for illustrative purposes, any of the principles and advantages can be applied in connection with detecting, generating alarms, and/or performing other actions related to any non-respiration and/or reduced respiration event, as appropriate. For example, any combination of features described with reference to apnea can be applied to hypopnea or any other respiratory condition or breathing pattern, some examples of which are disclosed herein.

In various embodiments, the system 100 can be configured to detect the presence of or the degree of paradoxical breathing, which is a signature of obstructed breathing, respiratory muscle weakness, respiratory failure, or any combination thereof. The system (e.g., a continuous monitor, quadrature continuous-wave Doppler radar system) can monitor the degree of paradoxical breathing based on analysis of the shape of the complex constellation and/or the trace of the plot of the in-phase (I) vs. quadrature (Q) signals from the quadrature radar receiver. An embodiment of a method to determine a paradoxical breathing indicator is illustrated in FIG. 28 and includes one or more of the following operations:

1. The paradoxical factor can be estimated by multiplying the ratio of the biggest eigenvalue to the second biggest eigenvalue by the ratio of the maximum peak-to-peak value of the signal projected on the principal eigenvector to the maximum peak to peak value of the signal projected on the vector orthogonal to the principal vector, as illustrated in block 2801.

2. The paradox index can be calculated as a cost function performed on the paradoxical factor.

3. If the paradox index is compared with one or more thresholds, it can be interpreted as the absence or presence of paradoxical breathing or the degree of asynchronous respiration.

Figure 14A:
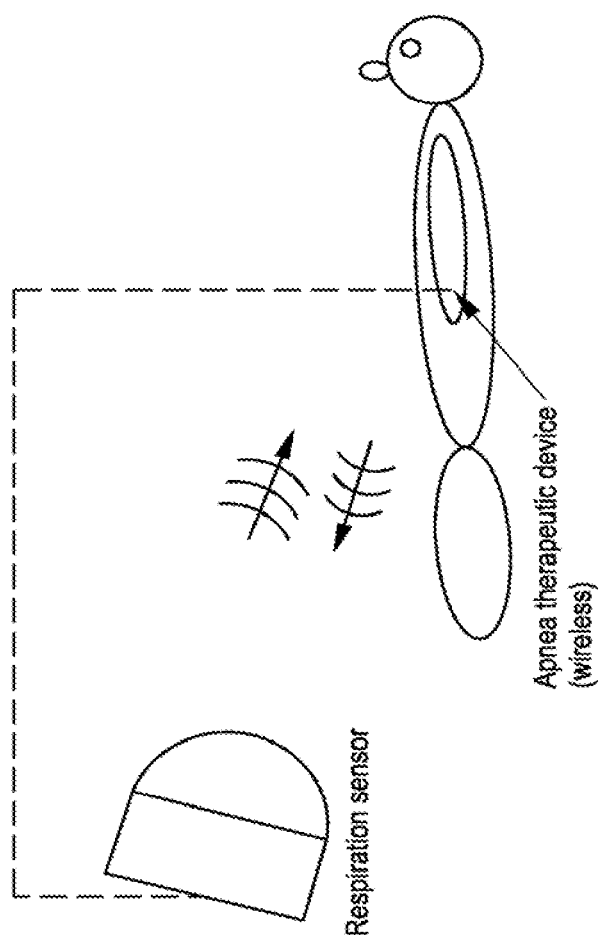
FIG. 14A depicts a wireless respiration sensor configured to measure respiration motion, determine apneic events and send commands to start and stop stimulation to the therapeutic device.
Figure 14B:
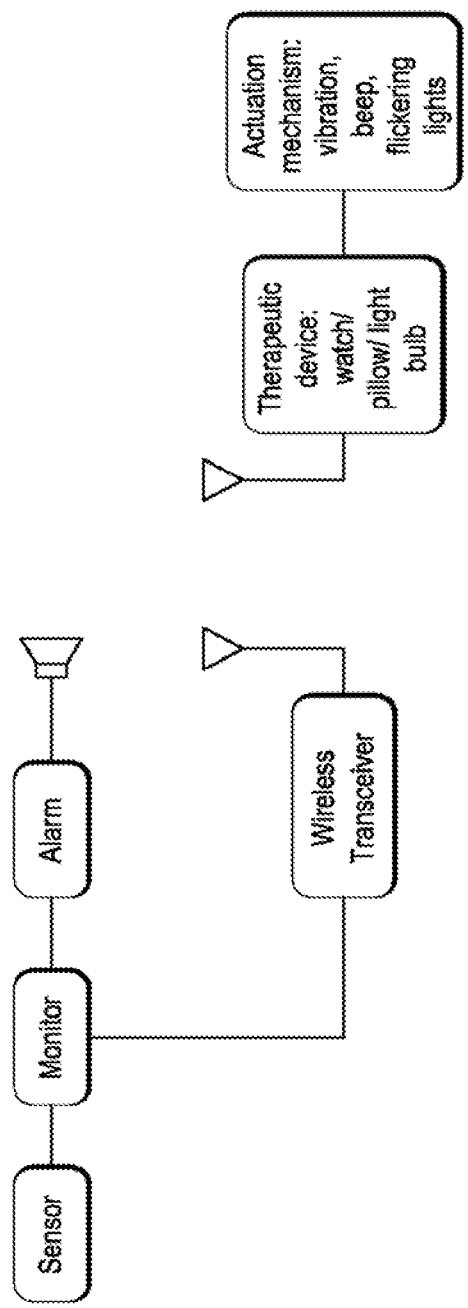
FIG. 14B shows an embodiment of an apnea therapy device and its components.

In various embodiments, a wireless home sleep monitor including one, two, or more sensors, e.g., a radar-based physiological motion sensor can be used as a sleep apnea therapeutic device as an alternative or in addition to other therapeutic devices, as shown in FIG. 14A. The home sleep monitor system can include a sensor and/or monitor configured to detect the apneic events and trigger a separate device (e.g., a module). In one embodiments, the system can be configured to detect a period of apnea, paradoxical breathing, or other parameter that occurs for about or at least about 5 seconds, 7 seconds, 10 seconds, 12 seconds, 15 seconds, 20 seconds, 30 seconds, 45 seconds, 60 seconds, or more in duration. The separate device can include but is not limited to, an audible alarm that can increase in volume, and/or wristwatch, pillow, mattress, clothing items, collars, neck patches, or any combination thereof that can vibrate with increasing intensity and/or electric shock, and/or light sources that flicker with intensity, as show in FIG. 14B. Unlike conventional alarms that are configured to alert a third party, such as a physician, nurse, or other healthcare provider of an apneic, hypopneic, or other adverse respiratory event, alarms in accordance with some embodiments herein are configured to stimulate the patient in order to treat an anatomic or physiologic condition associated with apnea, without necessarily arousing a patient from sleep. One goal is to stimulate the patient in order to treat an anatomic or physiologic condition associated with apnea, such as, e.g., stimulating the hypoglossal nerve region or other nerve region in the subject's neck to restore muscle tone to the genioglossus nerve or other nerve, thereby restoring the upper airway passage of the subject until the subject resumes normal breathing, without affecting or substantially affecting the subject's sleep architecture or without arousing the subject from sleep. In some embodiments, the therapeutic device can invasively or noninvasively, or directly or indirectly stimulate the diaphragm, intercostal muscles, accessory muscles, the brain (including the inspiratory, expiratory, pneumotaxic, and apneustic centers in the brain for example, and the medulla and pons areas of the brainstem), hypoglossal, glossopharyngeal, or vagus nerves. Thereafter, the home sleep monitoring system can send a command to the therapeutic device to stop stimulation and return to its idle or normal state until the next apneic event.

Not to be limited by theory, certain mechanisms describing potential mechanisms of respiratory physiology and sleep apnea will now be described. In some embodiments, one, two, or more therapeutic devices can be utilized to stimulate one, two, or more of the anatomical and/or physiologic systems described below.

During the day, stimulus from the descending reticular activating system creates the drive to breathe. Signals from chemoreceptors are combined in the brain stem to give a regular, rhythmic respiratory pattern. Reduced pressure levels of carbon dioxide (PCO2) during sleep are thought to inhibit ventilation. PCO2 at or below a certain level halts ventilation and causes apnea. An increase in alpha activity can be detected on an EEG indicating a lightening of sleep. Arousals can be associated with direct activation of the sympathetic nervous system creating an increase of adrenaline and noradrenaline in the blood. This lightened sleep stimulates wakeful control mechanisms stimulating ventilation. Rising PCO2 will cause a quick ventilatory response to correct arterial blood chemistry after being detected by medullary chemoreceptors. Breath-to-breath changes in extracellular fluid pH occur at these chemoreceptors and could influence respiratory center output. Low responses to chemical stimuli may result in respiratory pauses during sleep. High chemoresponsiveness produces respiration instability leading to cycling.

Chemoreceptors in blood vessels can quickly detect short term changes in arterial carbon dioxide tension (PaCO2), blood pH, and arterial oxygen tension (PaO2). Chemoreceptors in the brain are thought to be located at the ventral surface of the medulla oblongata, behind the blood brain barrier. Signals from these chemoreceptors are transferred to the respiratory center in the brain stem where they are processed and sent by efferent nerves to the respiratory muscles. One slow, deep breath can be enough to start an episode of periodic breathing; long respirations create slow chemical responses and changes blood pressure tensions.

The genioglossus tongue muscle plays an important role as a respiratory muscle by maintaining an open airspace for breathing. Signals sent to the hypoglossal motor nucleus have a specific effect on the genioglossus muscle. Suppression of the genioglossus muscle occurs during REM sleep because inhibitory neurotransmitters block hypoglossal muscle output to the genioglossus muscle causing the airway to narrow and carbon dioxide to build up in the blood. When an apnea occurs, gas exchange in the lungs is reduced causing a rapid decrease in PO2 and a subsequent rise in PCO2. The arousal that follows increases the respiratory drive exceeding the levels required to normalize breathing. This arousal driven breathing is a reflex response that further perpetuates periodic breathing. The buildup of CO2 in the blood causes reflex stimulation of genioglossus activity. Gamma-Amniobutyric Acid (GABA) is the main inhibitory neurotransmitter for the central nervous system with receptors throughout the medulla. Stimulating the GABA receptors at the hypoglossal motor nucleus suppresses hypoglossal motor output enough to diminish muscle tone.

Central sleep apnea will result if there is a malfunction in the neurons that control breathing during sleep. Nerve-signaling chemicals (neurotransmitters) send signals to nerve cells in the brain to control our sleep-wake cycles. Arousals from sleep have been associated with direct activation of the sympathetic nervous system (SNS). The SNS regulates pulse, blood pressure, and change in muscle tone. When PaO2 levels fall, the SNS alerts the brain to awaken the person enough to tighten the airway muscles, opening the trachea.

Norepinephrine is the primary neurotransmitter for the postganglionic sympathetic nervous system. Sleep apnea activates the sympathetic nervous system causing the release of norepinephrine. As blood oxygen saturation decreases there is an increased release of norepinephrine.

In the light stages of sleep periodic breathing is present and rarely found during REM sleep for most sleep apnea patients. During REM sleep, signals enter the base of the brain at the pons and travel to the thalamus, which relays signals to the outer cerebral cortex, which is responsible for learning and organizing information. Signals from the pons also shut off neurons in the spinal cord, temporarily paralyzing the muscles in the limbs.

Sleep-disordered breathing results from a combination of factors affecting upper airway patency and the control of ventilation. Although positive airway pressure therapy is the primary treatment for patients with moderate to severe obstructive sleep apnea syndrome, poor compliance and/or refusal is an issue in up to 40-50% of these patients. Alternatives to positive airway pressure therapy include mandibular repositioning appliances or surgical procedures that treat either soft tissue (resection, repositioning, or stiffening) or bony anatomy. Both modalities aim to correct specific anatomic abnormalities that may play a role in upper airway narrowing and collapse during sleep. Although the mechanisms underlying upper airway collapse are incompletely understood, there is clearly a decline in pharyngeal neuromuscular activity during sleep compared to wakefulness in obstructive sleep apnea patients. Thus, stimulation of upper airway muscles can be effective.

Various upper airway dilator muscles, especially the genioglossus, play a role in maintaining upper airway patency during sleep. The tensor veli palatini is one possible stimulation target; others include electrical stimulation of upper airway musculature to cause tonic and reflexive activation of the genioglossus muscle during wake and sleep. Consequently, methods have been explored to stimulate selectively upper airway dilator muscles, particularly the genioglossus.

Stimulation Frequency

In some embodiments, stimulation frequency, amplitude and pulse duration should be great enough to produce tetanic contraction of the muscle. In some embodiments, a stimulation frequency of >30 Hz could be used for this purpose. Thereafter, increases in frequency, amplitude, or pulse duration all produce progressively increasing levels of muscle recruitment. Muscle force is almost maximal at stimulation frequencies above 50 Hz. Therefore, in some embodiments, the frequency to obtain maximal airway opening could be between 25 Hz and 100 Hz, such as between 50 and 100 Hz, or at least about 25 Hz, 30 Hz, 35 Hz, 40 Hz, 45 Hz, 50 Hz, 60 Hz, 75 Hz, 100 Hz, or more. In some cases, there has been found to be a frequency-dependent effect of continuous stimulation on upper airway function.

Stimulation Amplitude

In some embodiments, fine wire electrodes or submental stimulation with large amplitudes (10-20 V), a frequency of 50 Hz, and a pulse duration of 0.2 m sec can be utilized. They found that the amplitude needed to induce EEG arousal from sleep was significantly higher than that producing barely tolerable sensation during wakefulness. In some embodiments, high stimulation amplitudes up to 10V, 15V, 20 V, 30 V, 40V, 50V, or more can be used for transcutaneous submental stimulation or intraoral stimulation, or between about 15-40 V. In various implementations, one or more sensory stimulating elements, such as a vibratory motor can be used to stimulate the patient in order to treat an anatomic or physiologic condition associated with apnea. The vibratory motor can have variable vibration amplitudes, displacements, and frequencies. In various embodiments, the frequency of vibration can be, for example, between about 40 Hz and 400 Hz, between about 100 Hz and 300 Hz, or around 220 Hz. Other parameters (e.g. amplitude, displacement, etc.) of the vibratory motor can be adjusted based on the required submental stimulation or stimulation of another anatomical region depending on the desired clinical result.

Pulse Duration

When stimulating skeletal muscles directly, in some embodiments, a marked increase in muscle tension can be obtained with increasing pulse duration to a range of 0.2-1.0 msec, or less than 1.0 msec, 0.8 msec, 0.6 msec, 0.4 msec, 0.2 msec, or less in some embodiments. Pulse duration is limited in some embodiments by the fact that longer pulse duration typically causes discomfort.

Timing of the Stimulation with Respect to the Respiratory Pattern

In some embodiments, an apnea-demand type stimulator was used for timing of surface submental stimulation. Stimulation can begin, for example, 5, 10, 15, or more seconds after apnea onset and switched off when airflow resumed or after 5 sec, 10 sec, or 15 sec, whichever came first. No stimulation was applied during periods of decreased airflow (hypopneas), and the timing of stimulation was not dependent on the respiratory cycle. In some embodiments, surface submental stimulation is applied during apneas. In some embodiments, different phases of the respiratory cycle are stimulated with submental and intraoral electrodes, including during obstructive events or before the onset of events. In some embodiments, intramuscular stimulation at the onset of inspiration can be used to obtain an improvement in airflow. Not to be limited by theory, airflow can return to baseline at offset of stimulation, and there is no hysteresis effect on the upper airway, requiring stimulation with the onset of each inspiratory effort.

Prevention of Awakening

Not to be limited by theory, when patients awaken during stimulation, the observed increase in airflow may be attributed to a generalized activation of the pharyngeal muscles rather than to an isolated recruitment of the stimulated muscle. In some embodiments, hypoglossal nerve stimulation is less likely to produce awakening or sleep interruption because the nerve is pure motor, as opposed to the sensory stimulation associated with direct intramuscular stimulation.

Apnea affects a large percentage of the population, and it would be desirable to monitor as well as treat apnea without surgery or cumbersome devices attached to the subject's body. In various embodiments, a wireless home sleep apnea therapeutic device can provide a more comfortable and/or attractive alternative to those currently on the market (e.g., surgery, oral appliance, various positive pressure devices via face masks or nostril masks with headbands, CPaP and BiPap), which can require bulky, uncomfortable, and/or noisy equipment. These removable devices result in discomfort to the subject and eventual lack of use by the subject, and surgery presents a risk due to the implant system. Thus, there is a need for improved treatment to apnea that can address the discomfort to the existing approaches. This wireless monitor can combine radar-based, non-contact measurement of respiratory effort and may contain other components, such as pulse oximeter(s), nasal or oral airflow sensor(s), acoustic stethoscopes or microphones, chest and abdomen sensors with wired or wireless communications, operating with or without wires on the patient and with or without minimal contact to the patient. In various embodiments, the pulse oximeter, nasal or oral airflow sensor(s), acoustic stethoscopes or microphones, and/or chest and abdomen sensors can be configured to independently send their data wired or wirelessly to the hub. This can provide an advantage over other commercially available home sleep monitors, which require bulky, uncomfortable, and/or noisy CPAP or Bi-PAP type of device.

In various embodiments, it is possible to measure respiratory motion without any contact to the subject with a radar-based system specifically configured to measure physiological motion, and respiratory motion can be derived from the physiological motion signal. In addition to detecting respiratory rates from the motion, respiratory motion can provide a measure of respiratory effort, similar to that provided by chest belts designed to measure respiratory effort. Measurements of respiratory effort can be useful in determining whether an event is a central apnea or an obstructive apnea. Respiratory motion can be measured with a radar-based system overnight, with the subject in any position in the bed.

In various embodiments, the radar-based device or chest and abdomen sensors can be configured to detect paradoxical breathing, when the abdomen contracts as the rib cage expands and/or when the rib cage contracts as the abdomen expands. During obstructive apnea, typically there is paradoxical breathing, although paradoxical breathing does not necessarily indicate an airway obstruction. An indication of paradoxical breathing and/or of the level of paradoxical breathing can be useful in detecting obstructive apnea.

In various embodiments, the radar-based device can also measure motion that is not due to respiration, which can indicate activity such as tossing and turning in bed, wakefulness, involuntary movement during sleep, the like, or any combination thereof. The quality of sleep can be estimated based on level of activity, and the level of activity can be helpful in determining the sleep state of the subject. The radar-based device can also be used to determine when the person is in the bed or out of the bed and/or to track how often the subject is getting out of bed during the night.

In some embodiments, the radar-based device may be configured to generate data related to a number of physiological parameters. For example, the radar-based device can generate data used to measure and/or generate alarms. In various embodiments, the radar-based device may also measure the heart rate. During apneic events, the heart rate can increase substantially, and the heart rate can be used to confirm an apnea that is indicated by other measurements. This can provide a higher confidence level that an apnea event has been detected. In various embodiments, the radar-based device can generate and/or display an indicator of a confidence level of detecting an apneic event.

In various embodiments, the radar-based device may be used to estimate the tidal volume, or the amount of air inhaled and exhaled with each breath. When the tidal volume is accurately measured, the tidal volume can be used to estimate the airflow.

In various embodiments, the radar-based device may include multiple-antenna hardware and software such that it can track the subject as he/she moves in bed during the night. This can provide information about how much the subject is moving within the bed, and can improve the radar-based measurement of respiration and activity.

In various embodiments, the radar-based device may be used in conjunction with one or more other sensors to provide a more complete picture of respiration during sleep. Additional sensors may include but are not limited to the pulse oximeter, nasal or oral airflow sensor(s), acoustic stethoscopes or microphones, and/or chest and abdomen sensors In various embodiments, the nasal/oral airflow sensor, acoustic stethoscope and/or microphone can provide an indication of whether the patient is breathing and/or, with a more advanced sensor, an estimate of the velocity of the airflow. This can be used to accurately detect apnea, and with the more advanced sensors, also detect hypopnea (reduction in airflow). An accurate measurement of airflow can be useful in determining whether an event is a hypopnea or an apnea. The nasal/oral airflow sensor may include one or more thermistors, hot-wire anemometers, pressure sensors, the like, or any combination thereof. For example, there may be more than one when the airflow in each nostril and/or at the mouth are measured independently. It may be difficult to determine whether an apnea is central or obstructive from only a single airflow sensor.

In various embodiments, the pulse oximeter can provide information on the effectiveness of respiration by arterial hemoglobin saturation, an estimate of blood oxygenation. Decreases in blood oxygenation can indicate the severity of an apneic and/or hypopneic event, and can be clinically significant. The pulse oximeter can also provide a heart rate measurement. Pulse oximetry data can be obtained from sensors on the finger or on the ear, but the finger measurements are generally considered more accurate.

In various embodiments, the pulse oximeter, nasal or oral airflow sensor(s), acoustic stethoscopes or microphones, and/or chest and abdomen sensors contact the patient, but in accordance with a number of embodiments described herein the pulse oximeter, nasal or oral airflow sensor(s), acoustic stethoscopes or microphones, and/or chest and abdomen sensors can advantageously transmit data wired or wirelessly to the data recording device. This recording device may be integrated with the radar-based device.

In various embodiments, this wireless home sleep monitor, including the radar-based device, pulse oximeter, nasal or oral airflow sensor(s), acoustic stethoscopes or microphones, and/or chest and abdomen sensors operating wired or wirelessly and with minimal contact to the patient, can provide a detailed picture of respiration during sleep including measurements related to: airflow, respiratory effort, and oxygenation. It can also provide measurements related to one or more of the following: the heart rate, variability in the heart rate, and information about motion during sleep. The pulse oximeter, nasal or oral airflow sensor(s), acoustic stethoscopes or microphones, and/or chest and abdomen sensors can independently send their data wired or wirelessly to the hub. This can provide a significant advantages over other commercially available home sleep monitors, which require wires to the recording device or wires to a single body-worn device with then wirelessly transmits data to the recording device.

Figure 14C:
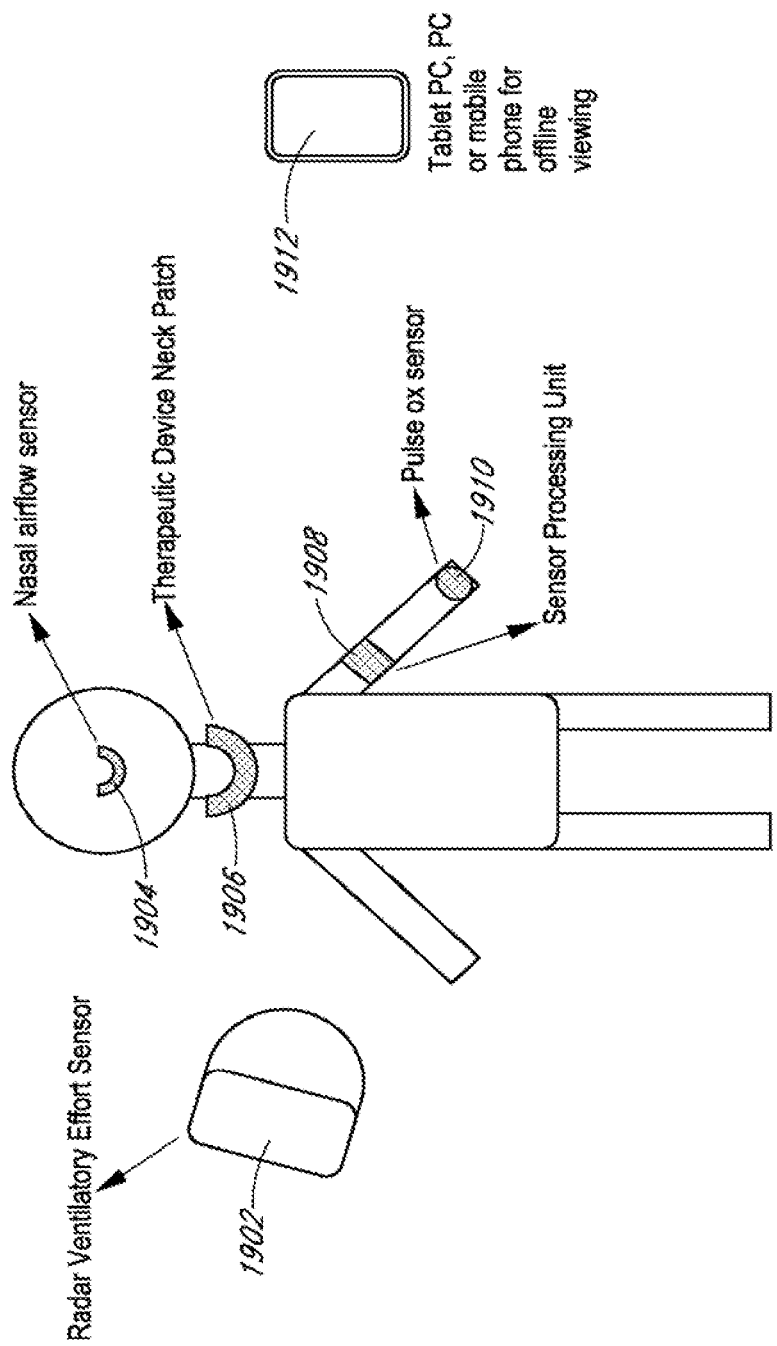
FIG. 14C shows an embodiment of an apnea therapeutic device configured to detect apneic events and send commands to start and stop stimulation to the therapeutic device.
Figure 20A:
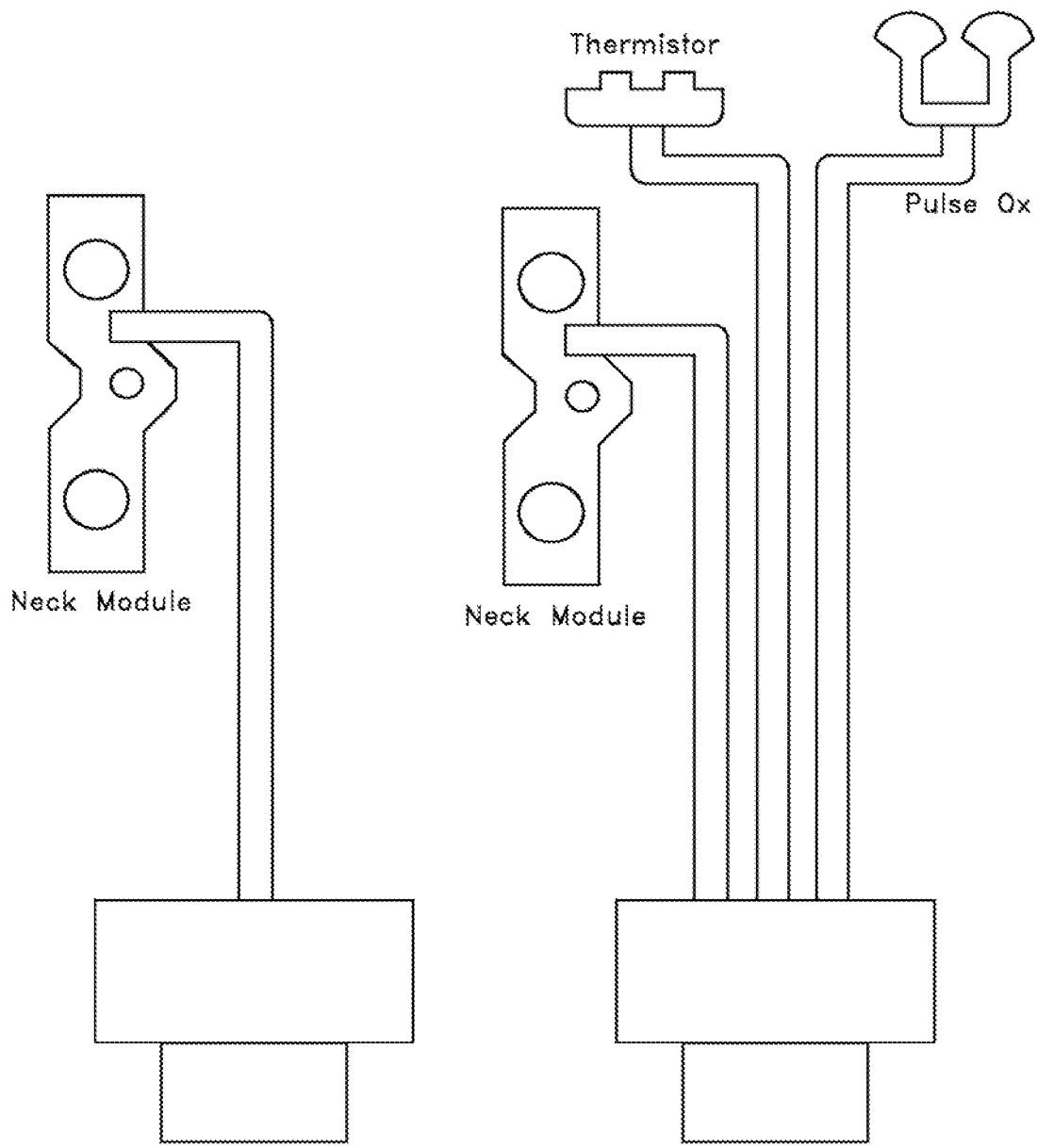
FIG. 20A show a possible cable breakout for connecting the optional sensors to the devices.

In various embodiments, the system can include one or more of a non-contact radar sensor aimed at the chest to detect ventilatory effort, a microphone embedded in the therapeutic device such as a sensor, e.g., a neck patch sensor to monitor airflow, a nasal airflow sensor such as an auxiliary airflow monitor, a pulse oximeter sensor to detect oxygen saturation and heart rate, and/or an accelerometer to detect body motion. FIG. 14C describes a system with a wireless radar sensor 1902, airflow sensor 1904, pulse ox sensor 1910, and therapeutic device neck patch 1906 all attached wired or wirelessly to the sensor 'processing unit 1908 with optional viewing through, for example, a tablet PC, PC, or mobile phone 1912. One or more of the sensors can be coupled with a sensor processing unit 1908 worn on the patient's arm or other location that may detect apneic events. One or more of the sensors may be wired to the sensor processing unit 1908 through possible cable breakouts as shown in FIG. 20A, or may wirelessly communicate to the sensor processing unit 1908. In addition, the sensor processing unit 1908 can include a communications module configured to communicate with a therapeutic device 1906. The therapeutic device 1906 can be configured to perform at least one action related to a sleep apnea state of the subject. The wireless sleep monitor can also include a therapeutic device 1906 comprising a bio-feedback mechanism configured to stimulate the patient in order to treat an anatomic or physiologic condition associated with apnea, e.g., the hypoglossal nerve region in the patient's neck when an apneic event is detected causing the patient to shift position, swallow, cough, move the palate or tongue, or restore muscle tone in the genioglossus muscle in the patient's neck, thereby restoring the upper airway passage. The sensor processing unit 1908 may detect the end of the apnea event and cease any electrical signal and mechanical stimulation in the neck patch 1906. The system may include a web based or PC based, for example application software 1940 for sleep quality analysis.

In various embodiments, the system can include one or more of an acoustic stethoscope or airflow sensor able to detect respiration, airflow and/or respiration rate, contact chest and abdomen sensor or sensors able to detect ventilatory effort, paradoxical breathing, and/or respiration rate, and/or strain gauge or other sensing technology such as PVDF to detect movement in response to stimulation.

In various embodiments, the thresholds to detect an apnea event on the sensor processing unit 1908 may be set by the manufacturer, hospital, healthcare practitioner, or subject.

In various embodiments, the sensor and/or neck patch 1906 may be capacitively coupled to automatically power on when placed in use.

In various embodiments, the neck patch 1906 may include a rechargeable or replaceable battery which may include a blinking light or annunciation of the battery condition.

In various embodiments, the neck patch 1906 and sensor may include storage of data or a web interface.

In various embodiments, the sensor may include its own display, user interface and controls, clock, recording hardware and software, and/or communications hardware and software.

In various embodiments, the neck patch 1906 and/or sensor may be coupled with a smartphone or computer tablet which may include its own display, user interface and controls, clock, recording hardware and software, and/or communications hardware and software.

In various embodiments, the device may include an embedded processor to process the signals and control the inter-sensor communications to relay data to the stand alone devices, such as a sensor, smartphone, or computer tablet.

In various embodiments, the neck patch 1906 may be in disposable form.

In various embodiments, the device may include a web based or PC based application software 1940 to assist the clinician in assessing subject's apnea severity by reporting sleep breathing disorder events and computing and reporting the AHI, event duration, and timestamps.

Figure 14D:
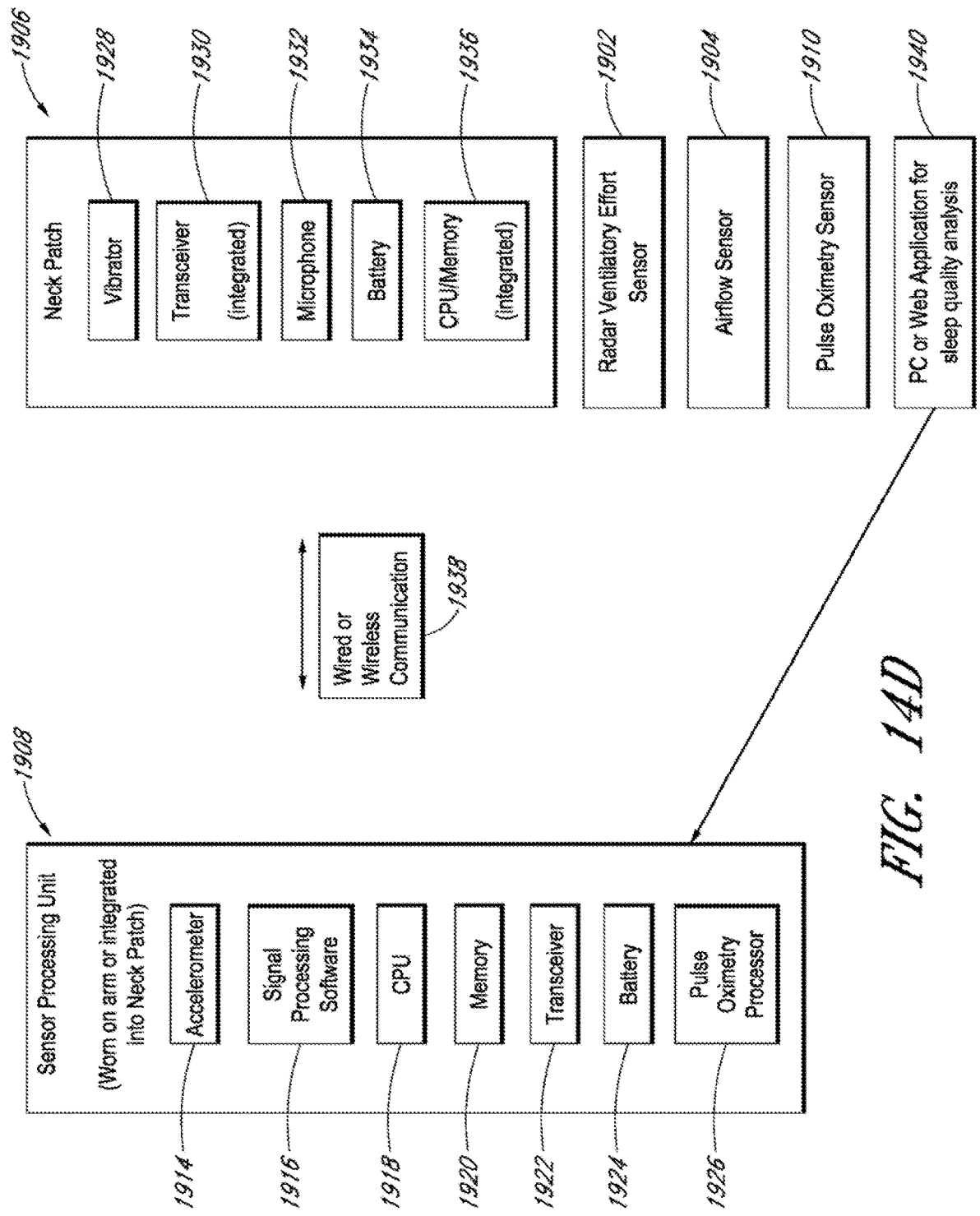
FIG. 14D shows an embodiment of an apnea therapy device and its components.
Figure 20B:
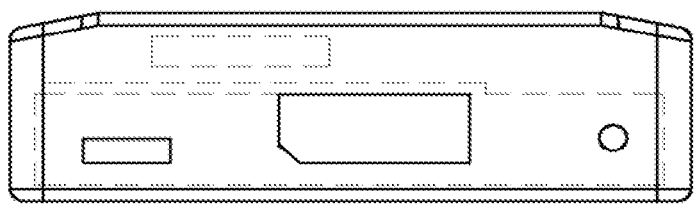
FIG. 20B shows the sensor processing unit's enclosure.
Figure 20B:
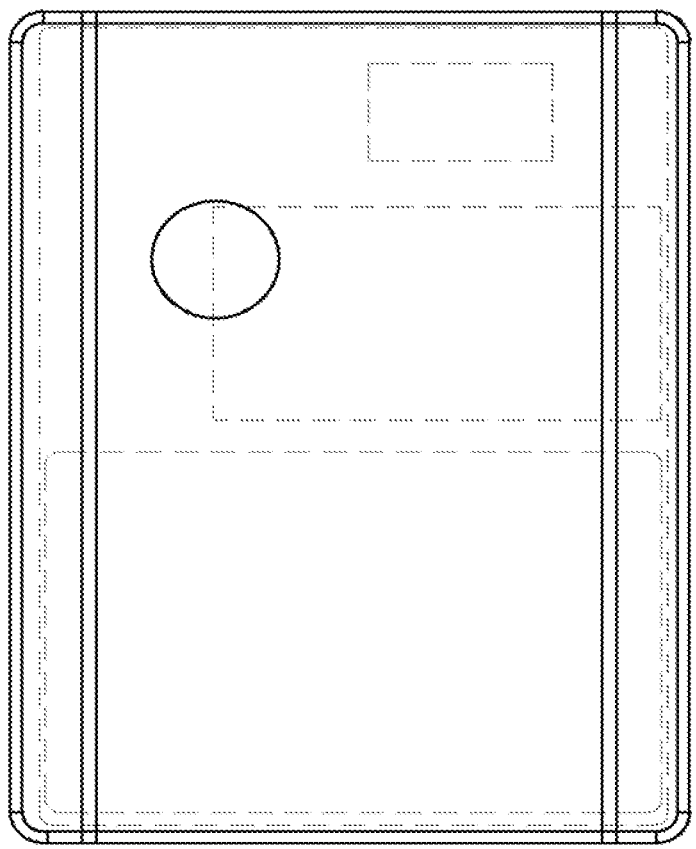
Figure 20B:
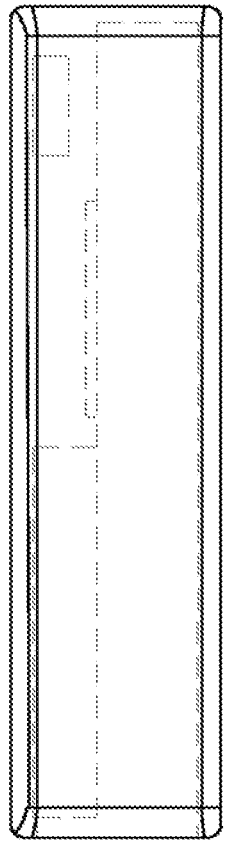
Figure 20B:
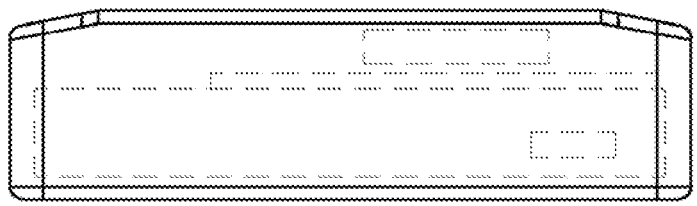

In various embodiments, the sensor processing unit 1908 may be housed in an enclosure worn on the arm or other location and integrated into the neck patch 1906, as shown in FIG. 20B. The sensor processing unit 1908 may include the CPU 1918, memory 1920 to store the respiratory waveforms and events, power management circuitry, rechargeable battery 1924, pulse oximetry processor 1926, a transceiver 1922 to communicate with and collect data from external sensors, and/or a wired connector and cabling 1938 to collect sensor data, as shown in FIG. 14D.

Figure 19:
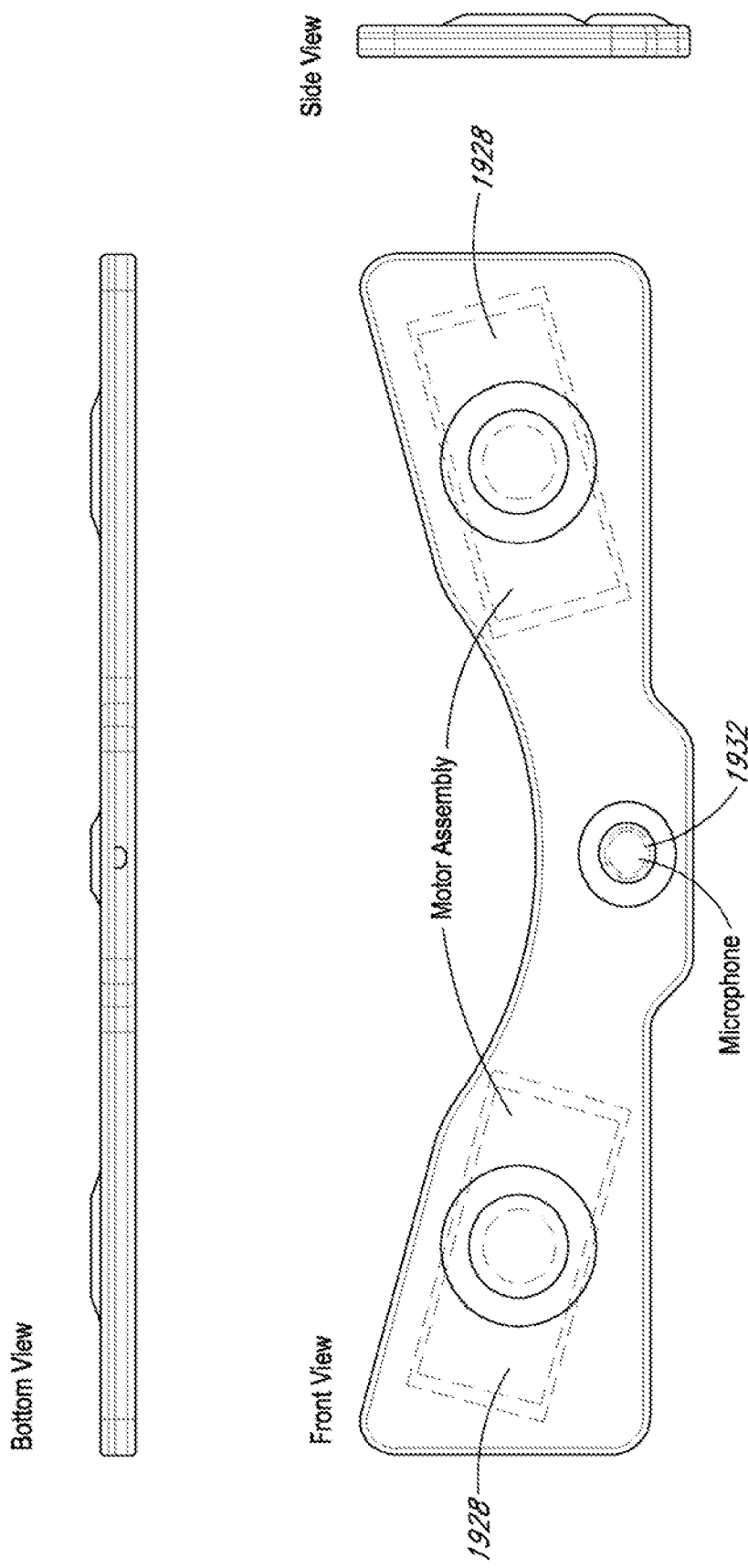
FIG. 19 shows a drawing of the neck patch which includes the vibrating motors and a microphone.

In various embodiments, the anatomical, e.g., neck patch 1906 is constructed from biocompatible materials, including a replaceable substrate with a biocompatible adhesive. The substrate may have an opening for a semi-rigid vibration plate attached to the motor, permitting direct contact of the vibration plate to the skin. The substrate may also have an additional opening permitting the microphone 1932 to be in close proximity to the skin near the larynx. The substrate may include indentations to accommodate the neck patch, sensor processing unit 1908, battery 1934, microphone 1932 and motor 1928. The neck patch cover encloses the components and substrate. The neck patch is shown in FIG. 19.

FIGS. 19A-19J illustrate various embodiments of a neck patch 1906 including a first layer and a second layer, e.g., adhesive and non-adhesive portions and, one, two, or more openings 1950, such as a central opening to which a sensory stimulating element, such as a vibratory motor 1960 can be attached. Motor 1960 could have frequency, amplitude, displacement, and other parameters as described elsewhere herein. The neck patch 1906 can comprise one, two, or more layers of foam, cloth or other biocompatible material. The opening 1950 in the layers of the neck patch 1906 can be used, for example, for retention of the vibratory motor 1960 such that the vibratory motor 1960 can be adhered to the neck region or some other anatomical region to stimulate one, two, or more nerves, muscles, or other structures associated with respiration or the airway, for example. The vibratory motor 1960 can be attached to the opening 1950 by various methods including but not limited to flanges, complementary locking mechanisms, an interference fit, adhesives, or mechanical methods such as a clip 1952, which could be horseshoe-shaped as shown in some embodiments. The adhesive portion, e.g., an inner layer of the neck patch 1906 can be used to secure the neck patch 1906 to the appropriate body part. The neck patch 1906 can have alignment edges 1954a and 1954b that allow the patient to align the neck patch 1906 to the appropriate anatomical region for optimum therapeutic or comfort placement. In some embodiments, first edge 1954a could either be parallel or non-parallel to second edge 1954b. In various implementations, one of the edges (e.g. edge 1955) of the neck patch 1906 can be used as a right or left side angle indicator. The outer layer, e.g., non-adhesive portion of the neck patch 1906 can allow the vibratory motor 1906 to freely move to stimulate the desired anatomical structure(s).

Figure 19A:
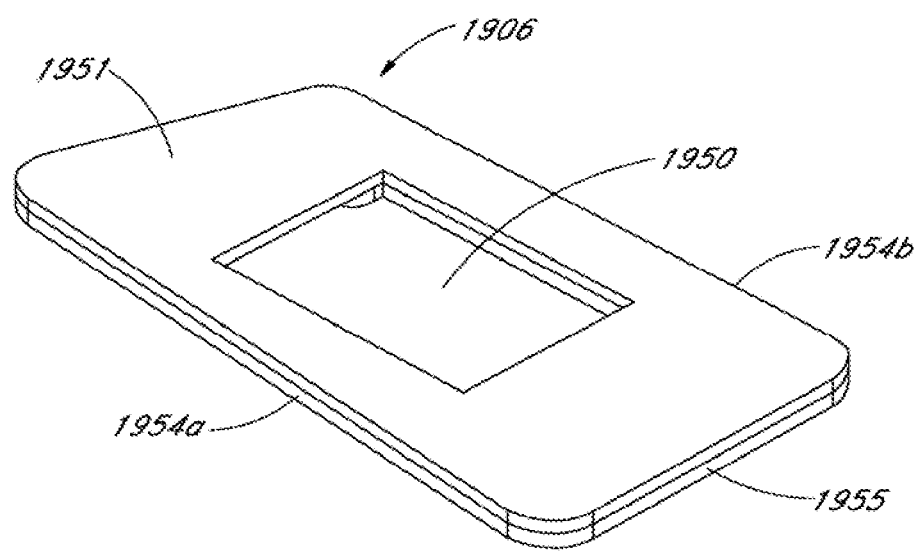
FIGS. 19A-19J schematically illustrate embodiments of a neck patch including adhesive and non-adhesive layers and an opening to which a vibratory motor can be attached.
Figure 19B:
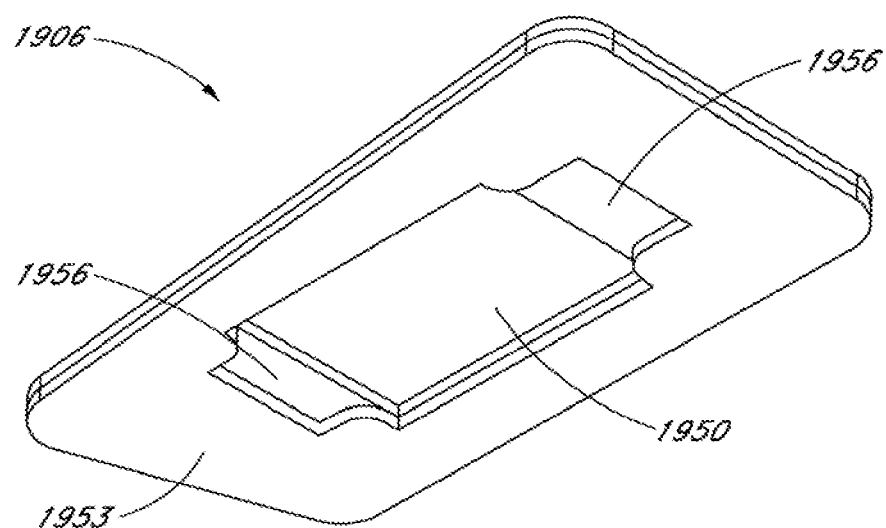
Figure 19C:
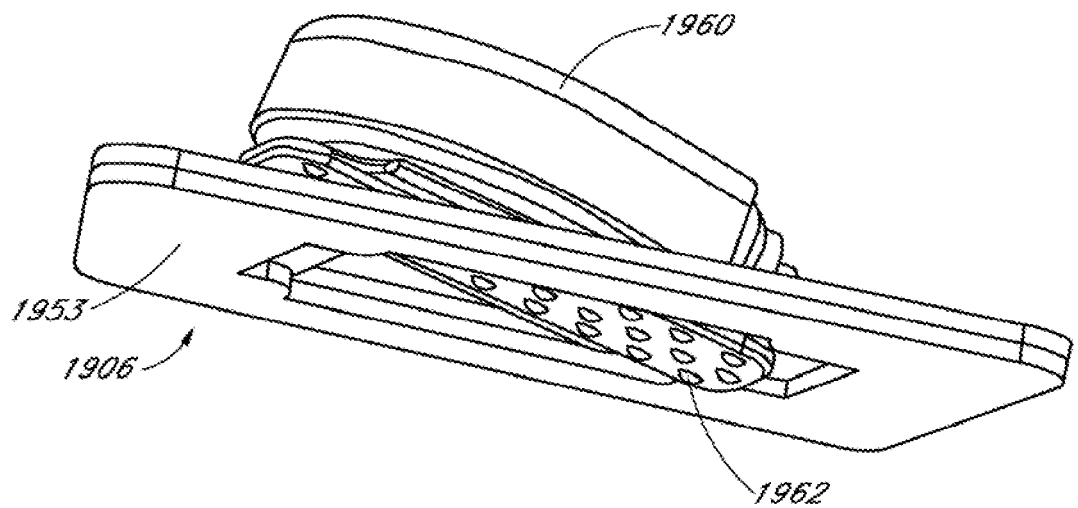
Figure 19D:
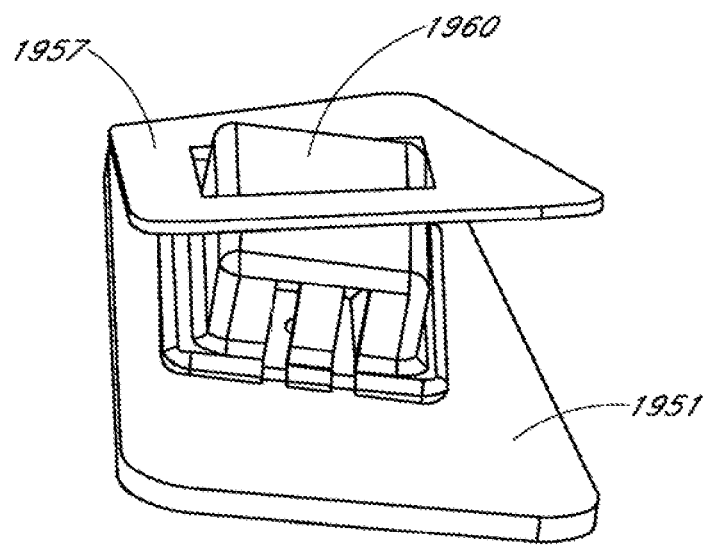
Figure 19E:
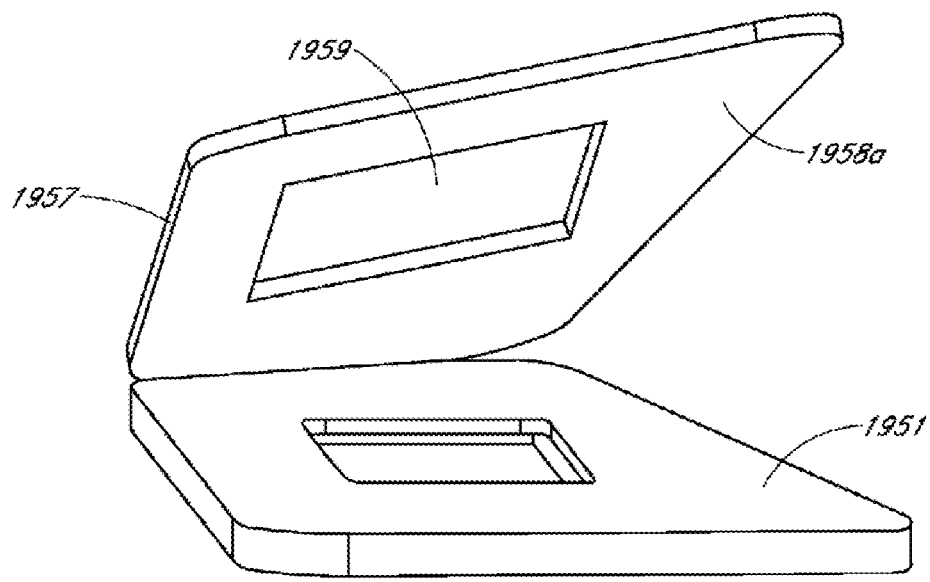
Figure 19F:
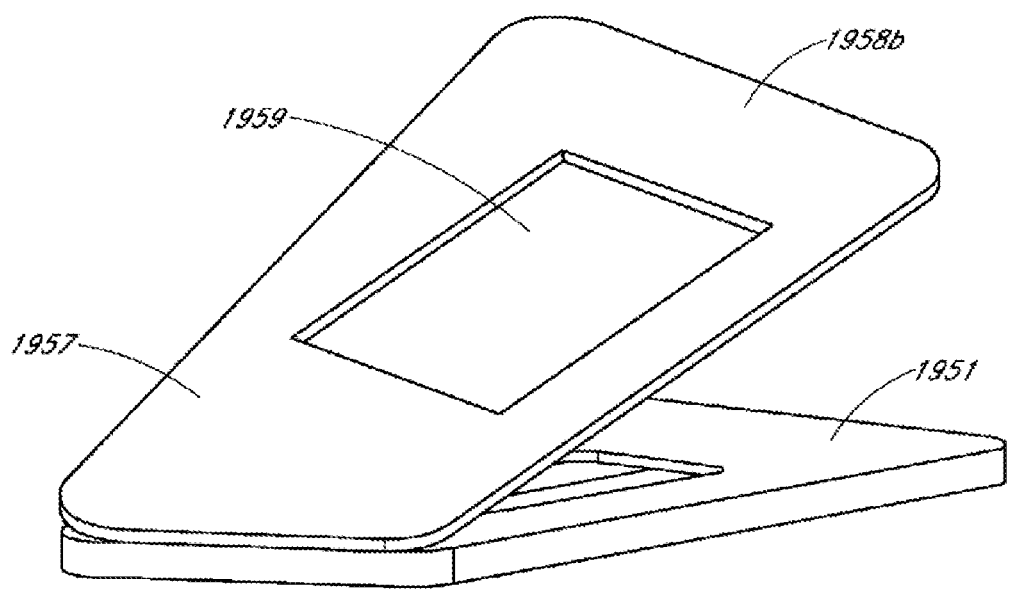
Figure 19G:
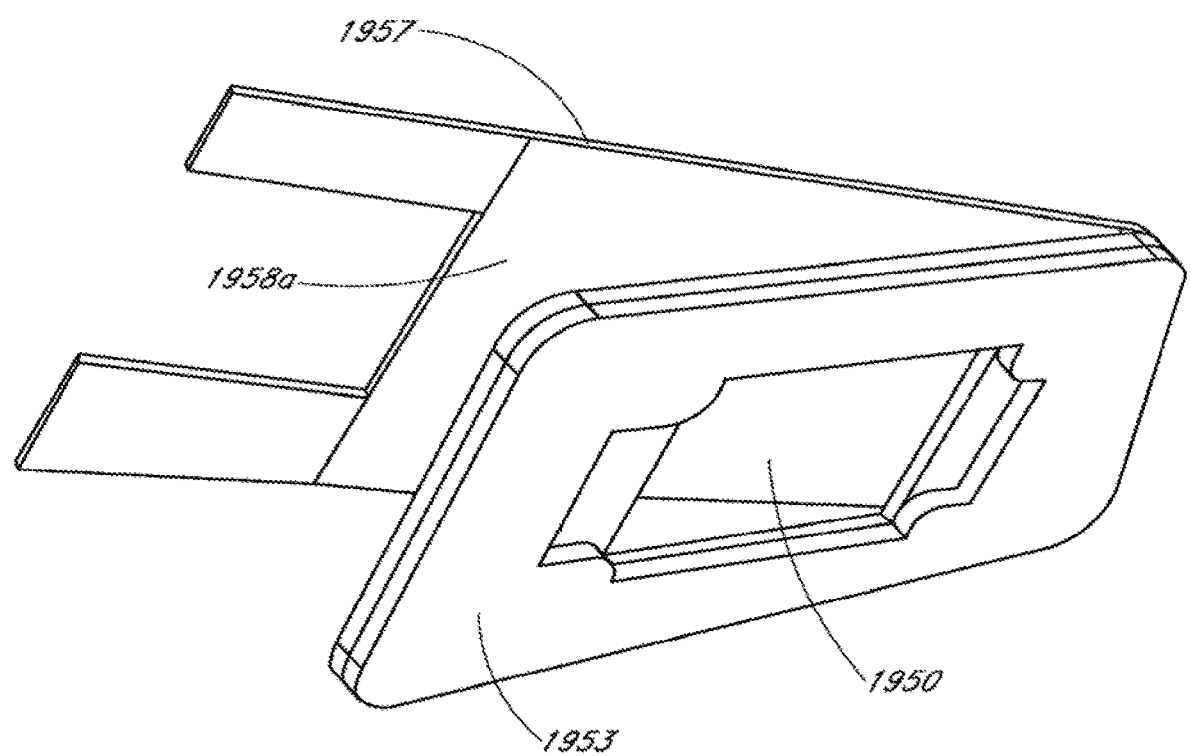

FIG. 19A illustrates the outer-facing surface of an embodiment of the neck patch 1906 which includes a first, e.g., base layer 1951 having a first outwardly facing surface and a second inwardly facing (e.g., toward the patient) surface. The base layer 1951 can comprise an attachment component on a surface, such as the inwardly-facing surface. The attachment component could be, for example, one-sided adhesive foam to attach the neck patch 1906 to the patient's skin. The base layer 1951 can include one, two, or more openings, such as a central opening 1950 through which the vibratory motor 1960 can be inserted and secured such that therapeutic vibrational energy can be effectively transferred to the required anatomical region. Opening 1950 can be square, rectangular, or another shape to accommodate the particular configuration of the sensory stimulation element. Sides of opening 1950 can be, in some embodiments, parallel or substantially parallel to, or angularly offset to that of the peripheral edges of the neck patch 1906. The peripheral edges of the neck patch could be right angles, rounded as illustrated, or another shape. FIG. 19B illustrates the inwardly-facing surface of the embodiment depicted in FIG. 19A which can include an attachment component on a surface, such as an adhesive portion 1953 on the patient-facing surface, a non-adhesive portion 1956, and opening 1950. The non-adhesive portion 1956 can include a clip retention element, a convolusion, or an overhang. The adhesive portion 1953 can include single or double-sided adhesive foam, for example, or another suitable attachment, and in some cases is made of a hypoallergenic or non-allergenic material. The adhesive portion 1953 can be used to secure the neck patch 1906 to the patient's skin. FIG. 19C illustrates the vibratory motor 1960 partially inserted through the opening 1950 of the base layer of the neck patch 1906. The vibratory motor 1960 can have one, two, or more force transfer regions 1962 through which therapeutic energy is delivered to the patient. In some embodiments, the force transfer regions 1962 can be regularly or irregularly spaced projections as illustrated, that could be arcuate, square, rectangular, triangular, or another desired shape. In various implementations, the vibratory motor 1960 has a radially-extending base flange such that the base flange can be secured between layers 1957, 1951 as shown in FIG. 19D. FIGS. 19E-19G illustrate embodiments of the retention layer 1957. The retention layer 1957 can comprise one or more layers made of cloth, foam, plastic, or some other material. In various implementations, the retention layer 1957 can be made of a material that is similar to or the same as other portions of the neck patch 1906, or of different materials. The retention layer 1957 includes an opening 1959. The opening 1959 is adapted to fit over a portion of the vibratory motor 1960 such that the motor 1960 is securely held. In various implementations, the size and the position of the opening 1959 in the retention layer 1957 can be substantially similar to the opening 1950 in the neck patch 1906. In other implementations, the opening 1959 in the retention layer 1957 can be different in size and position from the opening 1950 in the neck patch 1906. One side of the retention layer 1957 has an adhesive portion 1958a which adheres to the outer-facing surface of base layer 1951 of the neck patch 1906 when the retention layer 1957 is secured to the neck patch 1906. In some implementations, the outer-facing surface 1958b of the retention layer 1957 can be non-adhesive. The retention layer 1957 can have alignment edges similar to the alignment edges 1954*a* and 1954*b* that allow the patient to align the neck patch 1906 including the retention layer 1957 to the appropriate anatomical region for optimum therapeutic or comfort placement.

Figure 19H:
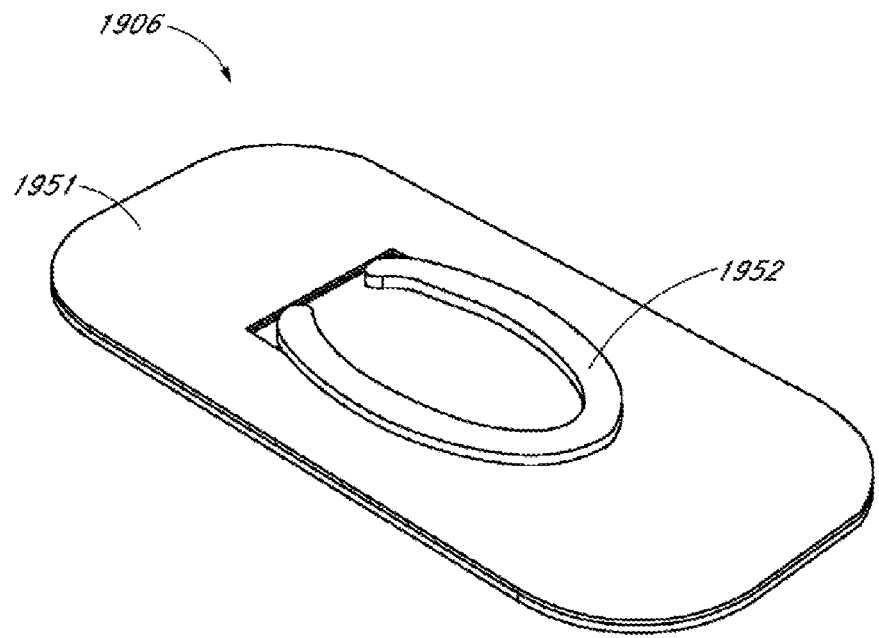
Figure 19I:
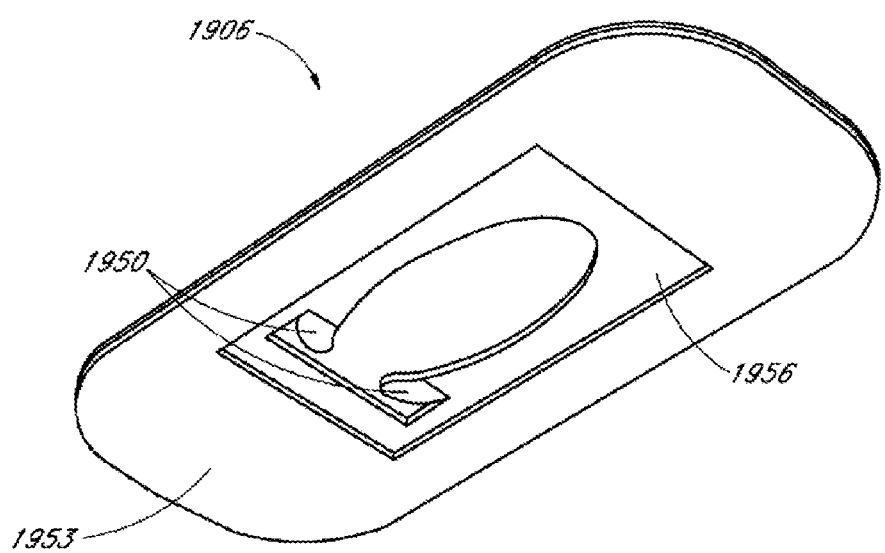
Figure 19J:
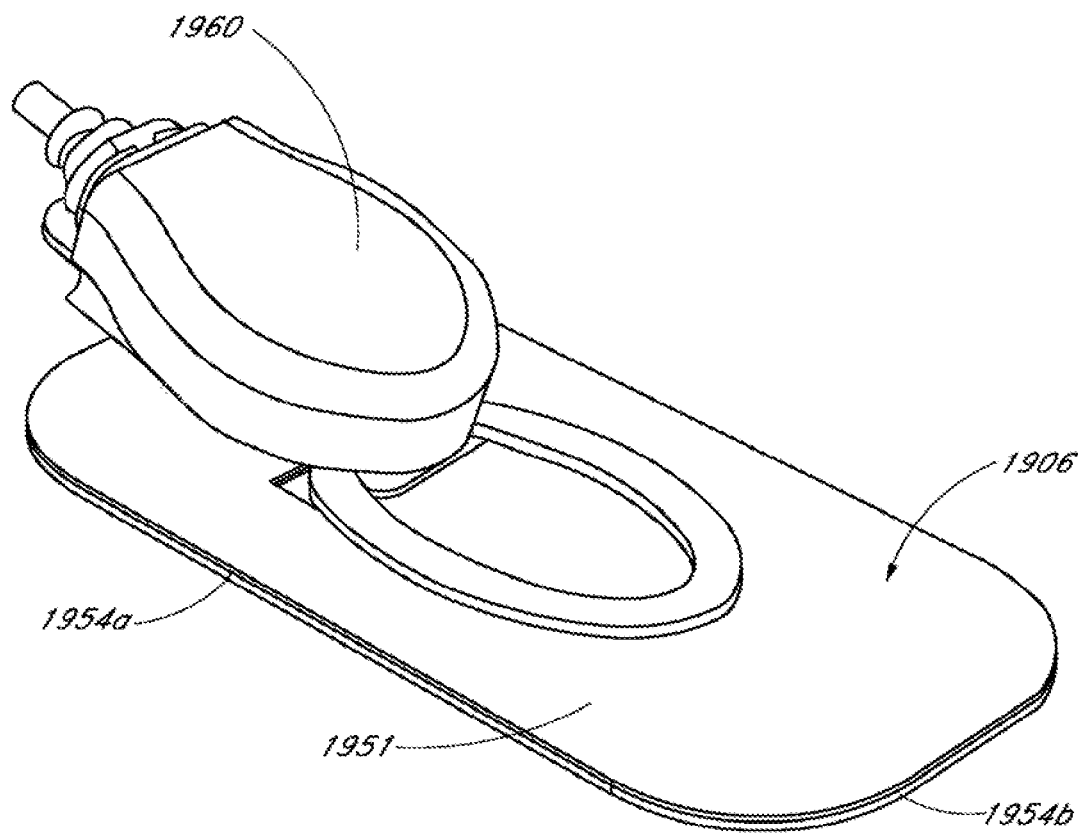

FIG. 19H-19J illustrate various embodiments of a neck patch 1906 including a horseshoe-shaped clip 1952 using which the vibratory motor 1960 can be more securely attached to the neck patch 1906. The clip 1952 can include, for example a semi-rigid material for secure attachment to the vibratory motor 1960. Other attachments mechanisms can also be utilized, some of which have been previously described.

III. Apnea Diagnosis Device

In various embodiments, a wireless home sleep monitor including a radar-based physiological motion sensor can be used as a sleep apnea diagnosis device as an alternative or in addition to other sleep apnea diagnosis devices. The home sleep monitor system can include a sensor and/or monitor configured to detect the apneic events. In one embodiments, the system can be configured to detect a period of apnea, paradoxical breathing, or other parameter that occurs for about or at least about 5 seconds, 7 seconds, 10 seconds, 12 seconds, 15 seconds, 20 seconds, 30 seconds, 45 seconds, 60 seconds, or more in duration.

Figure 17A:
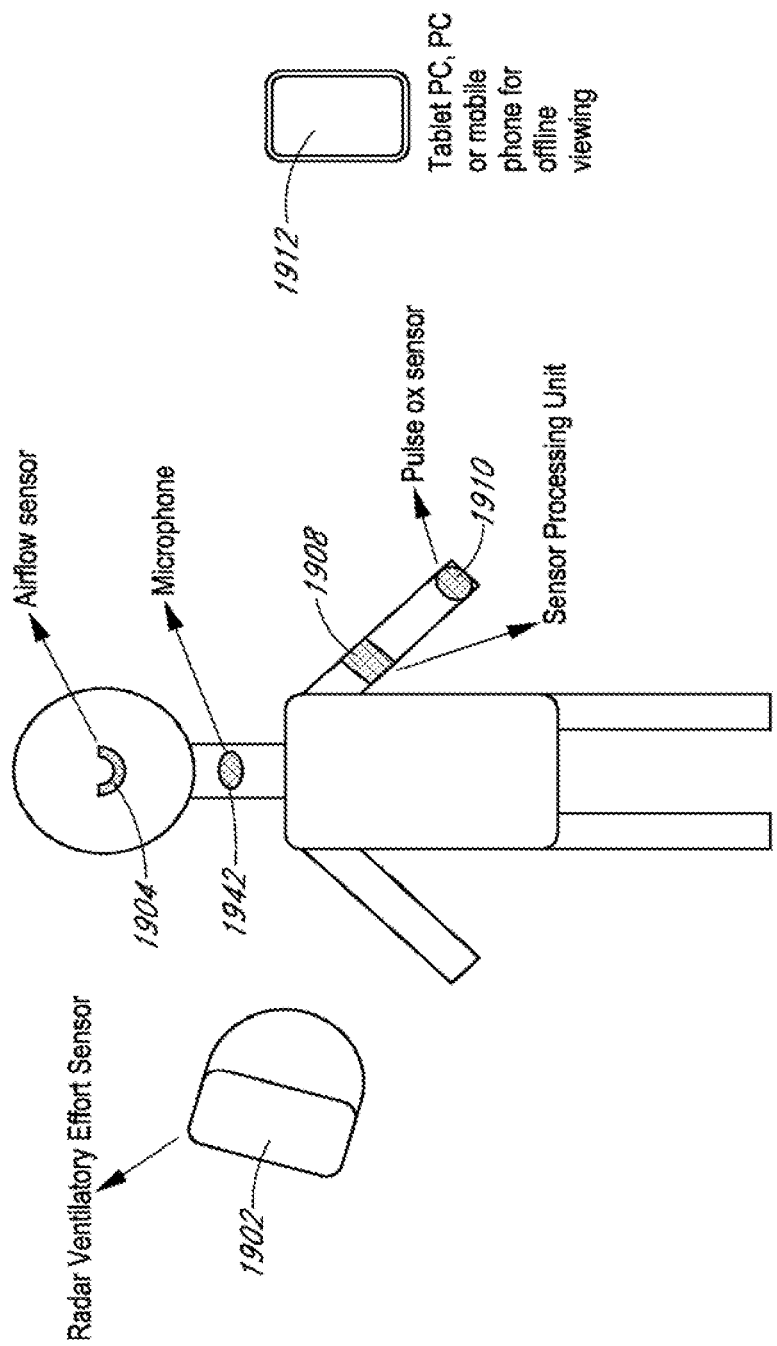
FIG. 17A shows an embodiment of a apnea diagnosis device configured to detect and collect apneic events in assessing a subject's apnea-hypopnea index (AHI)

Apnea affects a large percentage of the population (a majority of which do not know that they have apnea), and it would be desirable to diagnose sleep apnea in the comforts of a patient's home rather than performing a polysomnography study (PSG) which may require an overnight stay at a hospital, sleep study, or other healthcare facility. In various embodiments, a wireless home sleep apnea diagnosis device can provide a more comfortable and/or attractive alternative to those currently on the market which can require bulky, uncomfortable, and/or noisy equipment. This wireless monitor can combine radar-based, non-contact measurement of respiratory effort and may contain other components, such as pulse oximeter(s), nasal or oral airflow sensor(s), acoustic stethoscopes or microphones, and/or chest and abdomen sensors with wired or wireless communications, operating with or without wires on the patient and with or without minimal contact to the patient. FIG. 17A describes a system with a wireless radar sensor 1902, airflow sensor 1904, microphone sensor 1942, pulse ox sensor 1910, all attached wired or wirelessly to the sensor processing unit 1908 with optional viewing through a tablet PC, PC, or mobile phone 1912. In various embodiments, the pulse oximeter, nasal or oral airflow sensor(s), acoustic stethoscopes or microphones, and/or chest and abdomen sensors can be configured to independently send their data wired or wirelessly to the hub.

In various embodiments, it is possible to measure respiratory motion without contacting the subject using a radar-based system specifically configured to measure physiological motion. Respiratory motion can be derived from the physiological motion signal. In addition to detecting respiratory rates from the motion, respiratory motion can provide a measure of respiratory effort, similar to that provided by chest belts designed to measure respiratory effort. Measurements of respiratory effort can be useful in determining whether an event is a central apneic or an obstructive apneic event. Respiratory motion can be measured with a radar-based system overnight with the subject in any position in the bed.

In various embodiments, the radar-based device or chest and abdomen sensors can be configured to detect paradoxical breathing when the abdomen contracts as the rib cage expands and/or when the rib cage contracts as the abdomen expands. Typically, there is paradoxical breathing during obstructive apnea, but paradoxical breathing does not necessarily indicate an airway obstruction. An indication of paradoxical breathing and/or of the level of paradoxical breathing can be useful in detecting obstructive apnea.

In various embodiments, the radar-based device can also measure motion that is not due to respiration, which can indicate activity such as tossing and turning in bed, wakefulness, involuntary movement during sleep, the like, or any combination thereof. The quality of sleep can be estimated based on level of activity, and the level of activity can be helpful in determining the sleep state of the subject. The radar-based device can also be used to determine when the person is in the bed or out of the bed and/or to track how often the subject is getting out of bed during the night.

In some embodiments, the radar-based device may be configured to generate data related to a number of physiological parameters. For example, the radar-based device can generate data used to measure and/or generate alarms. In various embodiments, the radar-based device may also measure the heart rate. During apneic events, the heart rate can increase substantially and/or an atrial or ventricular arrhythmia could occur, thus the heart rate and/or rhythm can be used to confirm an apnea that is indicated by other measurements. For example, the device could detect a measured heart rate increase over baseline of at least 10, 15, 20, 25, 30, 35, 40, or more beats per minute or an absolute heart rate of 100, 110, 120, 130, 140, or more This can provide a higher confidence level that an apneic event has been detected. In various embodiments, the radar-based device can generate and/or display an indicator of a confidence level of detecting an apneic event.

In various embodiments, the radar-based device may be used to estimate the tidal volume, or the amount of air inhaled and exhaled with each breath. When the tidal volume is accurately measured, the tidal volume can be used to estimate the airflow.

In various embodiments, the radar-based device may include multiple-antenna hardware and software such that it can track the subject as he/she moves in bed during the night. This can provide information about how much the subject is moving within the bed and can improve the radar-based measurement of respiration and activity.

In various embodiments, the radar-based device may be used in conjunction with one or more other sensors to provide a more complete picture of respiration and apneic events during sleep. Additional sensors may include but are not limited to the pulse oximeter, blood pressure measurement device, nasal or oral airflow sensor(s), acoustic stethoscopes or microphones, and/or chest and abdomen sensors In various embodiments, the nasal/oral airflow sensor, acoustic stethoscope and/or microphone can provide an indication of whether the patient is breathing and/or, with a more advanced sensor, an estimate of the velocity of the airflow. This can be used to accurately detect apnea, and with the more advanced sensors, also detect hypopnea (reduction in airflow). An accurate measurement of airflow can be useful in determining whether an event is a hypopneic or an apneic event. In some embodiments, reduction in airflow can be determined by a detection of a decrease in airflow of at least about 10%, 20%, 30%, 40%, 50%, or more over baseline. The nasal/oral airflow sensor may include one or more thermistors, hot-wire anemometers, pressure sensors, the like, or any combination thereof. For example, there may be more than one sensor when the airflow in each nostril and/or at the mouth are measured independently.

In various embodiments, the respiratory monitoring device, e.g., pulse oximeter can provide information on the effectiveness of respiration by arterial hemoglobin saturation, an estimate of blood oxygenation. Decreases in blood oxygenation can indicate the severity of an apneic and/or hypopneic event, and can be clinically significant. The pulse oximeter can also provide a heart rate measurement. Pulse oximetry data can be obtained from sensors on the finger or on the ear.

In various embodiments, the pulse oximeter, nasal or oral airflow sensor(s), acoustic stethoscopes or microphones, and/or chest and abdomen sensors contact the patient, but in accordance with a number of embodiments described herein the pulse oximeter, nasal or oral airflow sensor(s), acoustic stethoscopes or microphones, and/or chest and abdomen sensors can advantageously transmit data wired or wirelessly to the data recording device. This recording device may be integrated with the radar-based device.

In various embodiments, this wireless home sleep monitor, including the radar-based device, pulse oximeter, nasal or oral airflow sensor(s), acoustic stethoscopes or microphones, and/or chest and abdomen sensors operating wired or wirelessly and with minimal contact to the patient, can provide a detailed picture of respiration during sleep including measurements related to: airflow, respiratory effort, and oxygenation. It can also provide measurements related to one or more of the following: the heart rate and/or rhythm, variability in the heart rate, and information about motion during sleep. The pulse oximeter, nasal or oral airflow sensor(s), acoustic stethoscopes or microphones, and/or chest and abdomen sensors can independently send their data wired or wirelessly to the hub, such that few or no wires would be required. This can provide a significant advantages over other commercially available home sleep monitors, which require wires to the recording device or wires to a single body-worn device with then wirelessly transmits data to the recording device.

In various embodiments, the system can include one or more of a non-contact radar sensor 1902 aimed at the chest to detect ventilatory effort, a microphone embedded 1932 in a neck patch sensor 1906 to monitor airflow, a nasal airflow sensor 1904 as an auxiliary airflow monitor, a pulse oximeter sensor 1910 to detect oxygen saturation and heart rate, and/or an accelerometer to detect body motion. One or more of the sensors can be coupled with a sensor processing unit 1908 worn on the patient's arm or other location that may process detecting apneic events. One or more of the sensors may be wired to the sensor processing unit or may wirelessly communicate to the sensor processing unit. The system may include, e.g., a web based or PC based application software 1940 to assist the clinician in assessing subject's apnea severity by reporting sleep breathing disorder events and computing and reporting the AHI, event duration, and timestamps.

In various embodiments, the system can include one or more of an acoustic stethoscope or airflow sensor able to detect respiration, airflow and/or respiration rate, contact chest and abdomen sensor or sensors able to detect ventilatory effort, paradoxical breathing, and/or respiration rate, and/or strain gauge or other sensing technology such as PVDF to detect movement in response to stimulation.

In various embodiments, the thresholds to detect an apnea event on the sensor processing unit may be set by the manufacturer, hospital, healthcare practitioner, or subject.

In various embodiments, the sensor may be coupled with a smartphone or computer tablet which may include its own display, user interface and controls, clock, recording hardware and software, and/or communications hardware and software.

In various embodiments, the device may include an embedded processor to process the signals and control the inter-sensor communications to relay data to the stand alone devices, such as a sensor, smartphone, or computer tablet.

In various embodiments, the device may include, e.g., a web based or PC based application software 1940 to assist the clinician in assessing subject's apnea severity by reporting sleep breathing disorder events and computing and reporting the AHI, event duration, and timestamps, and/or other patient information.

Figure 17B:
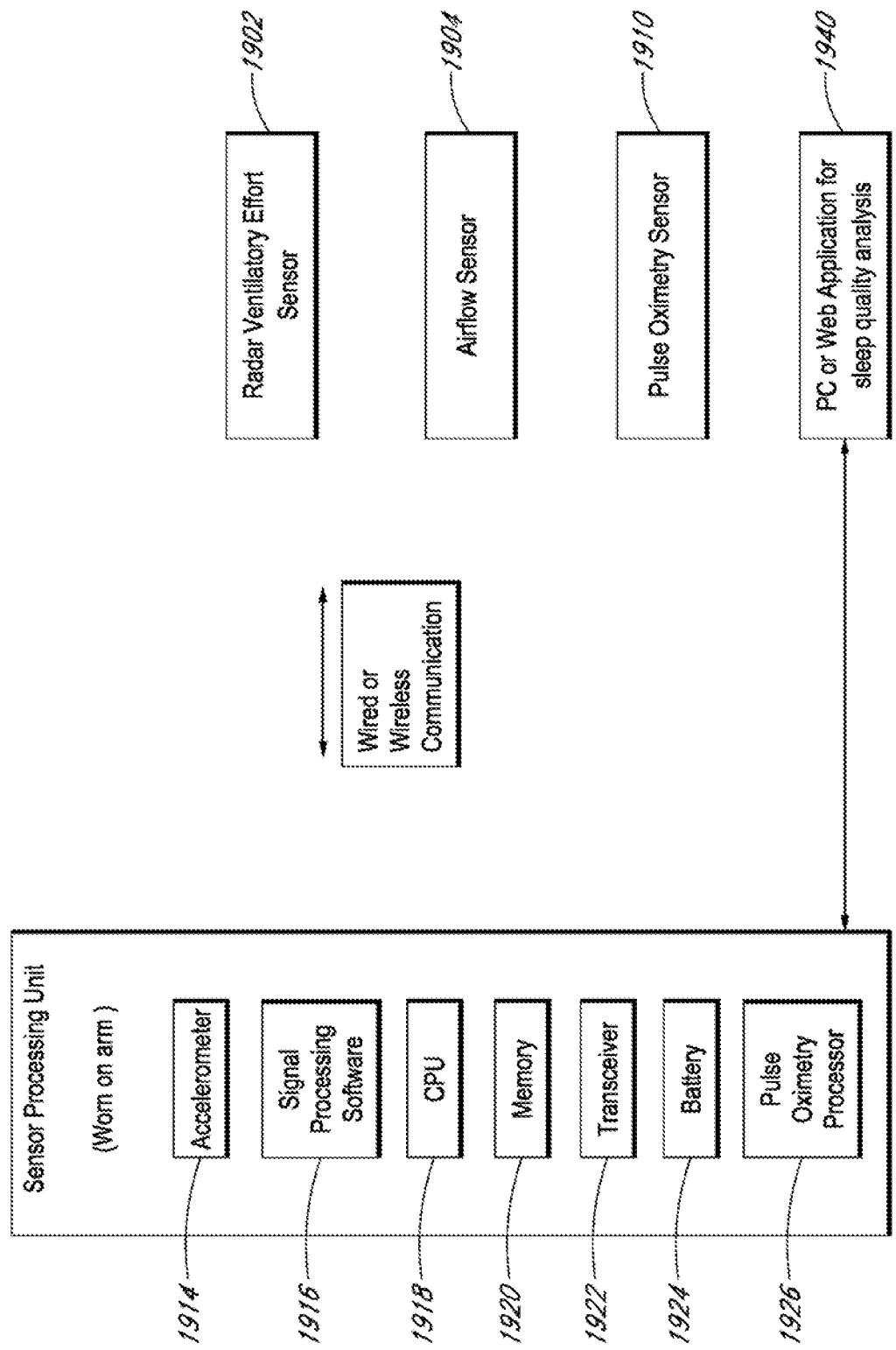
FIG. 17B shows an embodiment of a apnea diagnosis device and its components.

In various embodiments, the sensor processing unit 1908 may be housed in an enclosure worn on the arm or other location. The sensor processing unit 1908 may include the CPU 1918, memory 1920 to store the respiratory waveforms and events, power management circuitry, rechargeable battery 1924, pulse oximetry processor 1926, a transceiver 1922 to communicate with and collect data from external sensors, and/or a wired connector and cabling 1938 to collect sensor data, as shown in FIG. 17B.

IV. Snore Therapy Device

Figure 18A:
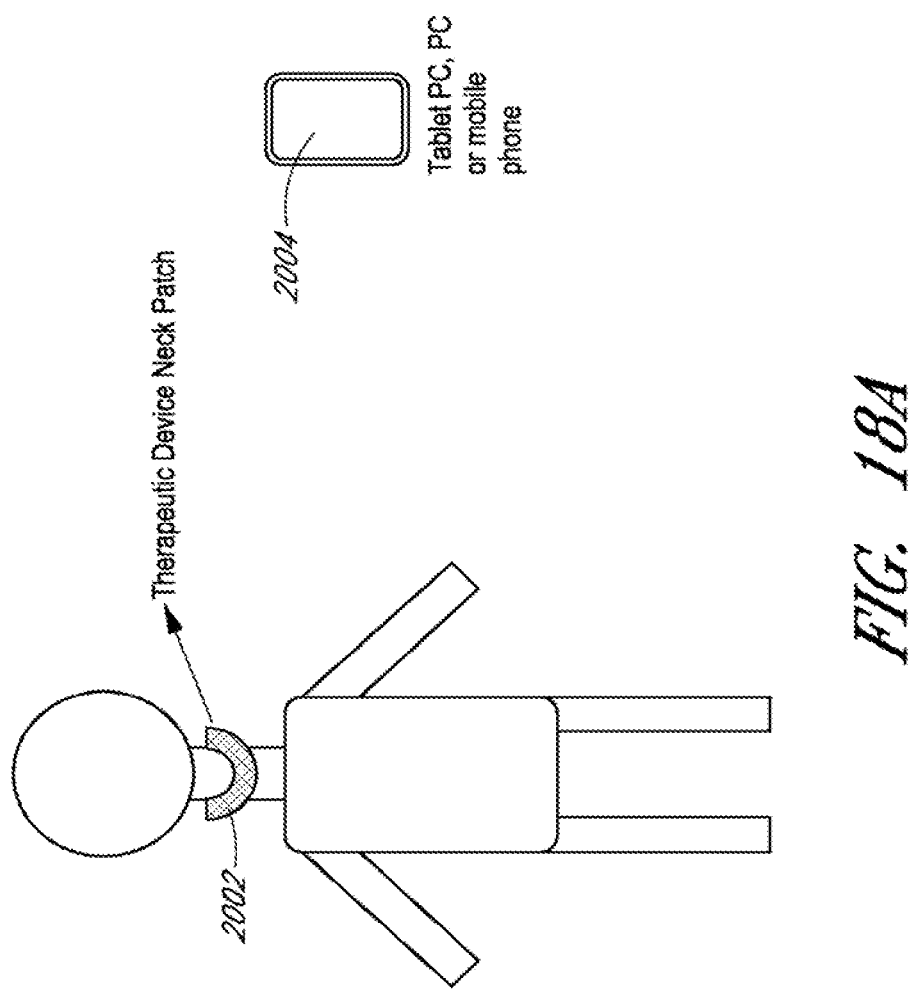
FIG. 18A shows an embodiment of a snore therapy device configured to detect snoring events and start and stop stimulation of the therapy device.

In various embodiments, a system for detecting and treating snoring is provided. The system can include one or more microphones or other transducer which may utilize a snoring detection algorithm to determine the onset of a snoring event. The therapeutic device can be configured to perform at least one action related to detecting and treating a snoring event, which could in some cases signal partial or complete airway obstruction, and/or affect the sleep of others within hearing range of the patient. As shown in FIG. 18A, the therapeutic device 2002 may comprise a biofeedback mechanism configured to stimulate, for example, an anatomical or physiologic sector associated with airway obstruction, including the hypoglossal nerve region in the patient's neck when snoring event is detected causing the patient to shift position, swallow, cough, move the palate or tongue, or restore muscle tone in the genioglossus muscle in the patient's neck, thereby restoring the patency of the upper airway passage and possibly terminating or alleviating the snoring event. The therapeutic device may include electrical, electromechanical, or purely mechanical devices, including but not limited to a vibrating transducer and/or electrodes which can produce electrical signals to produce mechanical stimulation including vibrations to stimulate the subject's neck muscles which will increase in sensation until the snoring event is stopped. The device may be coupled with a separate stand-alone device, such as a sensor, smartphone, or computer tablet 2004 with its own display, user interface and controls, clock, recording hardware and software, and/or communications hardware and software.

In various embodiments, the snore therapy device can be configured to detect a period of snoring, or other parameter that occurs for about or at least about 1 second through 15 seconds, inclusive, or more in duration. One goal is to terminate the snoring event without affecting the subject's sleep architecture or without arousing the subject from sleep at which point the snore therapy device will stop stimulation and return to its idle or normal state until the next snoring event.

Snoring affects a large percentage of the population, and it would be desirable to treat snoring without surgery or cumbersome devices attached to the subject's body. In various embodiments, a contact therapeutic device can provide a more comfortable and/or attractive alternative to those currently on the market (e.g., surgery, oral appliance, etc.). Removable devices currently on the market cause discomfort to the subject and eventual lack of use by the subject, and surgery presents a risk due to the implant system. Thus, there is a need for improved treatment to snoring that can address the discomfort to the existing approaches. This snore therapy device may contain components, such acoustic stethoscopes or microphones, operating with or without wires on the patient and with or without minimal contact to the patient In various embodiments, the acoustic stethoscope and/or microphone(s), or other devices can provide an indication of whether the patient is snoring. This can be used to accurately detect snoring.

In various embodiments, the acoustic stethoscopes or microphones can advantageously transmit data wired or wirelessly to the data recording device.

In various embodiments, the thresholds to detect a snoring event may be set by manufacturer, hospital, healthcare practitioner, or subject.

In various embodiments, the neck patch 2002 may be capacitively coupled to automatically power on when placed in use.

The device may comprise a strain gauge or other sensing technology such as PVDF to detect movement in response to stimulation.

In various embodiments, the neck patch 2002 may include a rechargeable or replaceable battery 2024 which may include a blinking light or annunciation of the battery condition.

In various embodiments, the neck patch 2002 may include storage of data or a web interface.

In various embodiments, the neck patch 2002 may be coupled with a separate stand-alone device, such as a sensor, smartphone or computer tablet which may include its own display, user interface and controls, clock, recording hardware and software, and/or communications hardware and software.

In various embodiments, the device may include an embedded processor to process the signals and control the inter-sensor communications to relay data to the stand alone devices, such as a sensor, smartphone, or computer tablet.

In various embodiments, the neck patch may be in disposable form.

In various embodiments, the device may include a web based or PC based application software to assist the subject in assessing subject's snoring severity by reporting snoring events and computing and reporting the number of events, event duration and timestamps.

Figure 18B:
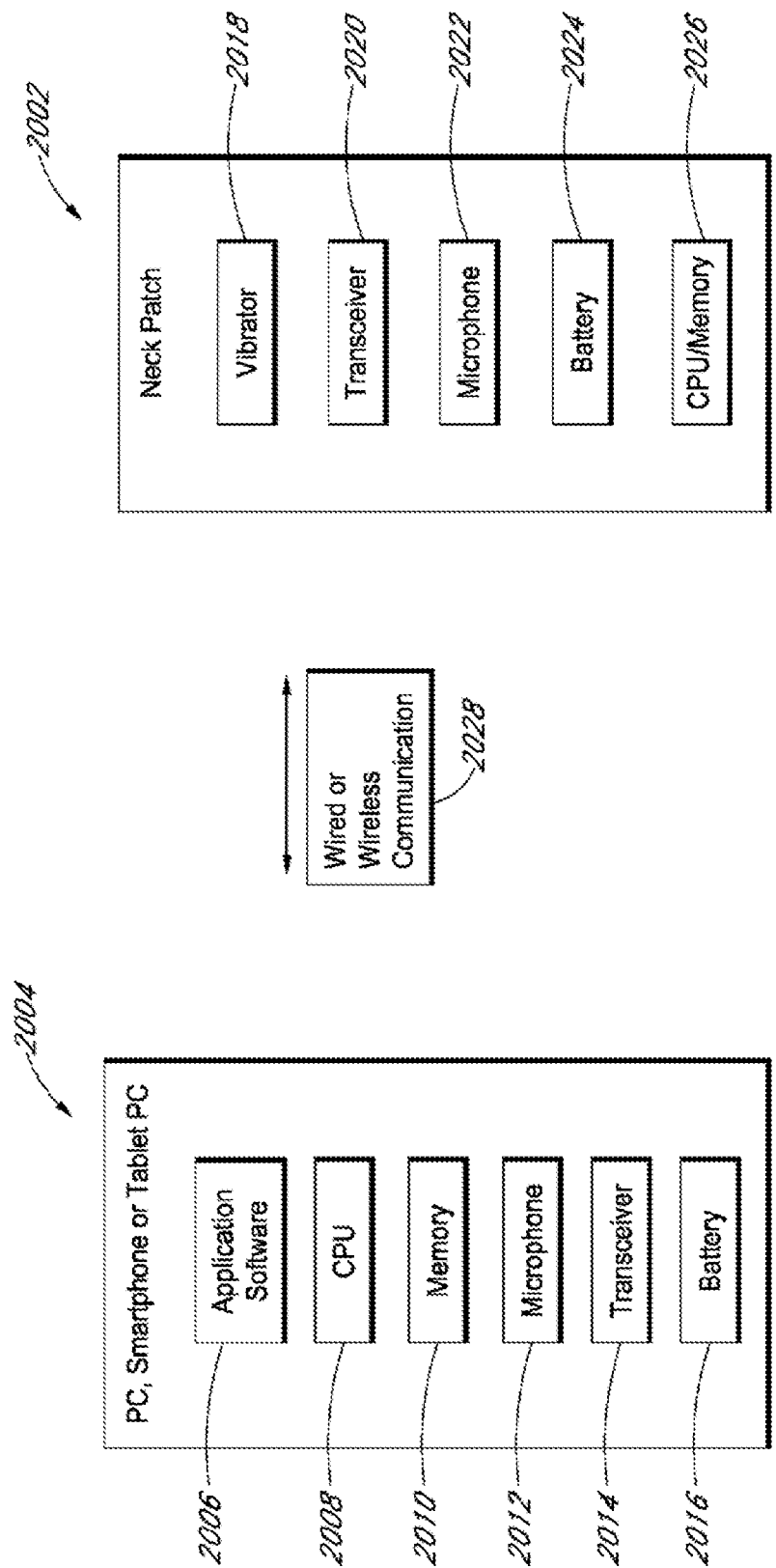
FIG. 18B shows an embodiment of a sleep therapy device and its components.

In various embodiments, the neck patch 2002 is constructed from biocompatible materials, including a replaceable substrate with a biocompatible adhesive. The substrate has an opening for a semi-rigid vibration plate attached to the motor, permitting direct contact of the vibration plate to the skin. The substrate has an additional opening permitting the microphone to be in close proximity to the skin near the larynx. The substrate has indentations to accommodate the neck patch sensor processing unit 2026, battery 2024, microphone 2022, and motor 2018, as shown in FIG. 18B. The neck patch cover encloses the components and substrate.

In various embodiments, PC, smart phone, or tablet PC 2004 may include one or more of following: the application software 2006, CPU 2008, memory 2010 to store the snoring events, microphone 2012, rechargeable battery 2016, a transceiver 2014 to communicate with and collect data from external sensors, and/or a wired connector and cabling to collect sensor data 2028, as shown in FIG. 18B.

V. Sway Cancellation

One potentially significant source of interference in measuring the respiration and/or heart signals of a human subject while standing can be the back and forth sway of the standing subject. A system including two, three, four, five, or more sensors can be used to detect and/or cancel out sway motion. The two or more sensors can be positioned in any suitable location to detect motion of a subject, such as a patient. The two or more sensors can include two or more radar sensors. For example, the system can include a first sensor configured to detect sway motion of a patient at a first location, and a second sensor spaced apart from the first sensor configured to detect sway motion of a patient at a second location. The first sensor and the second sensor can be positioned, for example, at opposing sides of the subject. More specifically, in some embodiments, the system can include a first sensor at the front of a subject and a second sensor at the back of the subject. Alternatively or additionally, in some embodiments, the system can include a first sensor at a right side of a subject and a second sensor at a left side the subject. While sensors can be oriented about 180 degrees apart with respect to the subject, an angle between the first sensor, the subject/patient, and second sensor can be between about 160 and 220 degrees, between about 150 and 210 degrees, between about 100 and 260 degrees, or other angles for example depending on the desired clinical result.

Although some features are described with reference to a system with a first sensor at the front of the patient and a second sensor at the back of the patient for illustrative purposes, any combination of the principles and advantages of the system can be applied to any other system with two or more sensors configured to generate sway data related to two or more locations of a patient, for example, as described above. In some embodiments, a system with two or more radar sensors can be used to detect a subject's motion from both the front and back at substantially the same time. When the subject is swaying, the motion signals from the radar sensors can represent a combination of swaying and respiration motion. A subject's swaying motion can generate a signal in the back sensor with the opposite polarity of the signal generated in the front sensor. However, since cardiopulmonary motion can cause expansion and contraction of the subject's torso, such that all sides move towards the body's center or away from the body's center, cardiopulmonary motion can generate signals with the same polarity that will be the same in the front and back sensors. In some embodiments, the signals from the front and back sensors may be added to minimize the swaying motion, while approximately doubling the amplitude of the cardiopulmonary signal. In some embodiments, an additional benefit of this method is an increased signal-to-noise ratio (SNR), indicating a stronger signal relative to noise, because the summation of two independent outputs can reduce white Gaussian noise, thus resulting in higher SNR.

In some embodiments, a linear combination of the signals from the two sensors can be calculated to cancel the swaying motion, when the amplitude of the two signals is not equal. In some embodiments, this linear combination may be calculated using an adaptive filter. In some embodiments, the adaptive filter may be based on a least mean squares algorithm. In some embodiments, an additional sensor signal that detects sway but not respiration, such as a laser sensor fixed on a part of the body that sways but does not move with respiration, or a signal from a load cell may be used as a reference input for the adaptive filter. In some embodiments, the linear combination of the two radar signals may be calculated to minimize the signal power, in which the weighting factors for each signal can be positive such that the respiratory signal is not likely to be cancelled. In some embodiments, the linear combination may be calculated using demodulated signals. In some embodiments, a linear combination of the quadrature signals may be calculated before demodulation. In some embodiments, the signals may be rotated in the I/Q plane and the radii adjusted such that the lines or arcs on which they are projected are co-located and then a least mean square adaptive filter may be applied to the quadrature representation of the signals: Q+jI.

In some embodiments, the powers of the first and second signal can be different as the radar cross section of a subject's front and back may vary. The signals from the front and back sensor may also be affected by different delays. In some embodiments, a complex weight factor may be used to compensate these effects, as represented by the following expression:

$Ae^{j\theta}$, where A can represent power and $\theta$ can represent phase.

In some embodiments, the complex weight factor can be selected by solving for A and $\theta$ to minimize undesired signal power for the sum of the front and back signal. In some embodiments, the undesired signal power may be that of a certain bandwidth. In some embodiments, the undesired signal power may be some specific frequency such as that of the swaying motion. In some embodiments, MMSE estimation may be used to solve for A and $\theta$. In some embodiments, LSE may be used to solve for A and $\theta$.

In some embodiments, the sway signal may be isolated from the respiratory signal using independent components analysis, or blind source separation algorithms applied to the signals from the two sensors. In some embodiments, empirical mode decomposition algorithms may be applied to the signals from the two sensors to separate the respiratory signal from the swaying signal. In some embodiments, after an algorithm is applied to isolate the two signals, the respiratory signal can be determined using an algorithm that uses signal features to identify whether or not a signal corresponds to respiration. In some embodiments, after an algorithm is applied to isolate the two signals, the swaying signal can be determined as the one that most closely matches the signal from another sensor used to detect swaying without detecting respiratory motion.

In some embodiments, a third sensor can be used to help identify if a subject is swaying or not swaying, or otherwise moving. In some embodiments, the sensor may be a load cell. It can be desirable for the load cell to have enough resolution to determine a weight shift of the subject as he or she sways forward and backward. Such a sensor may also identify whether a swaying motion is periodic and, if so, what determine a frequency of motion. In some embodiments, if no swaying is detected, the signal from the front sensor can be used to obtain a subject's cardiopulmonary motion. In some embodiments, the back sensor may be used. In some embodiments, both signals may be considered and the stronger signal is used. In some embodiments, both signals may be considered and the signal having lower noise and/or interference may be used. In some embodiments, both signals may be considered and the signal with less non-cardiopulmonary motion identified can be used. In some embodiments, both sensors can function as a diversity system; thus simple summation of the sensors outputs can be used to obtain a subject's cardiopulmonary motion with higher SNR. In some embodiments, each sensor may demodulate incoming signals independently followed by adaptive filtering to maximize cardiopulmonary motion signals.

In some embodiments, the third sensor used to identify subject swaying can be an optical sensor such as that based on a laser. In some embodiments, this optical sensor can be focused on an area of the body that may sway without having significant respiratory motion, such as the legs and/or the head. In some embodiments, the third sensor used to identify subject swaying can be an ultrasound sensor.

Figure 15A:
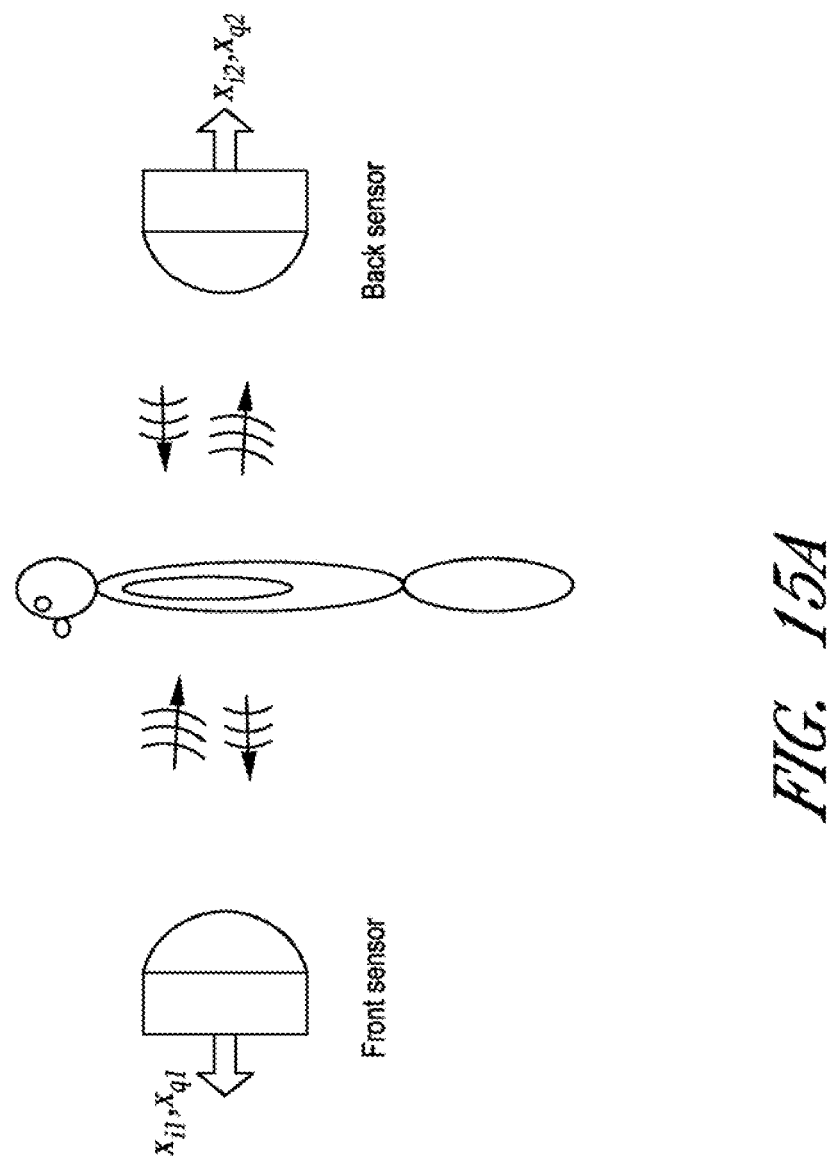
FIG. 15A shows an embodiment of an a system for vital signs measurement for a standing subject using two Doppler radar sensors.

In some embodiments, a dual sensor approach with sensors 1 and 2 placed in front of and behind the standing subject can be used to record and cancel the sway movement and recover the physiological signals, with sample results shown in FIG. 15A.

Figure 15B:
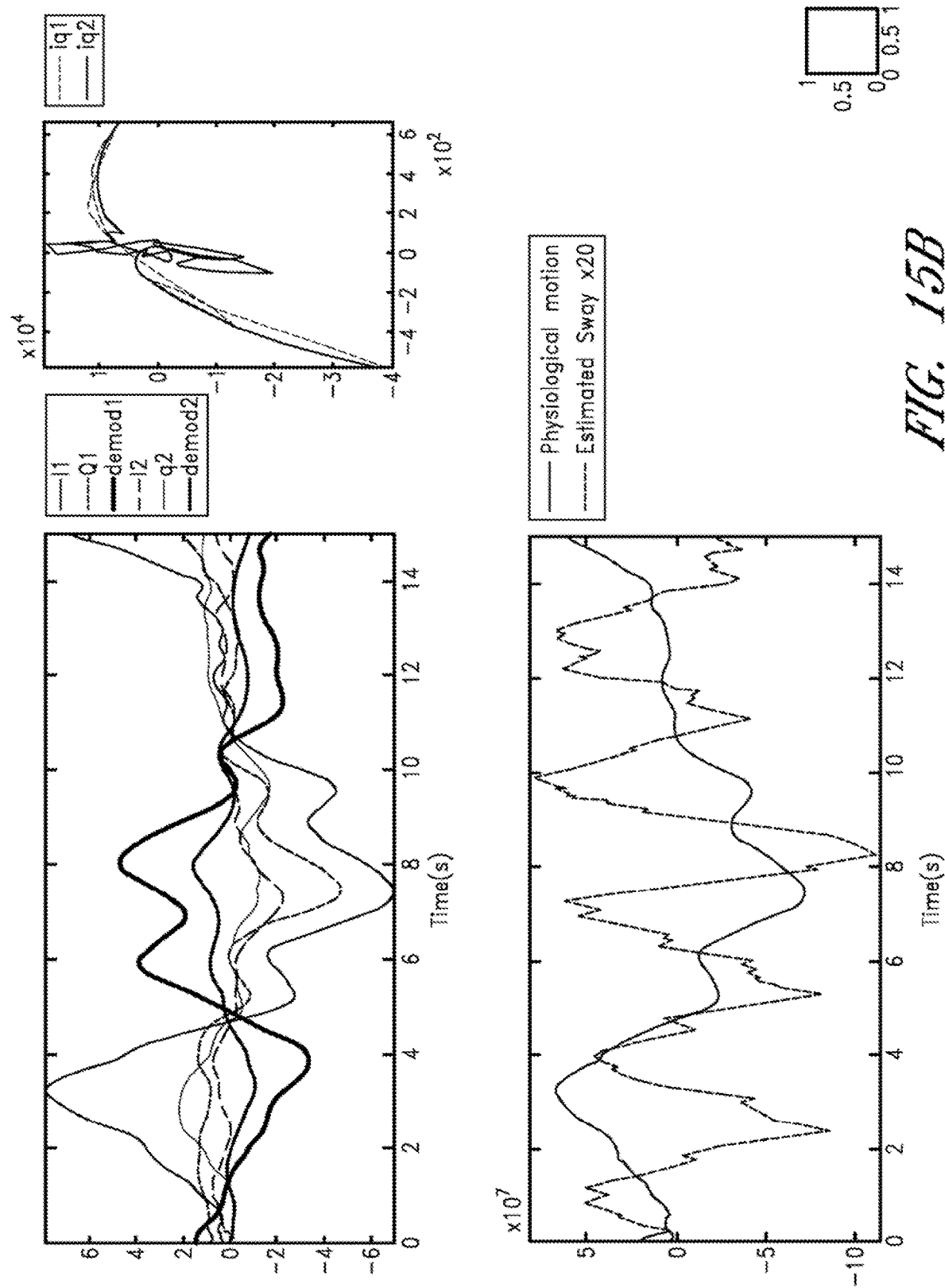
FIG. 15B shows plots of signals acquired from two sensors that have been processed, yielding physiological motion and estimated sway signal.

In some embodiments, as shown in FIG. 15B, one or more of the following operations can be performed on the signals obtained from both of the sensors:
1. Acquire time synced I and Q signals from both of the sensors. $x_{i1}$, $x_{q1}$ from sensor 1 and $x_{i2}$, $x_{q2}$ from sensor 2.
2. Perform Principal Component Analysis (PCA) on $x_{i1}$, $x_{q1}$ and call the result D1
3. Perform Principal Component Analysis (PCA) on $x_{i2}$, $x_{q2}$ and call the result D2
4. Perform PCA on D1 and D2. Choose the output with the smaller eigen value as a physiological signal and the output with larger eigen value as the sway component.

V. Detection of Apneic Events and Cessation of Breath

The subset of frames can include samples obtained over a period of time longer than the expected period of respiration. In some embodiments, the subset of frames can include samples obtained over a period of time longer than the expected cycle period of irregular respiration. The method can also include using a wavelet transform function to create an index of repeating patterns in a respiration signal. In some embodiments, the irregularity of the breath-to-breath interval, or breath duration, can be estimated from one or more of the following: the standard deviation of the breath-to-breath interval, the frequency of apneaic events, the coefficient of variation of the breath-to-breath interval, the standard deviation of the respiratory rate, and the coefficient of variation of the respiratory rate. In some embodiments, the irregularity of the amplitude of a breath and/or the depth of breath, and/or breath duration, can be estimated from the standard deviation of the breath depth, the coefficient of variation of the breath depth, the standard deviation of the respiratory signal amplitude, the coefficient of variation of the respiratory signal amplitude, or any combination thereof. Information regarding the irregularity or regularity of respiration can include assessment of whether irregular breathing is periodic. This assessment can include estimating each breath-to-breath interval, and storing it with the time point at the end of the interval in which it was calculated; interpolating between these breath-to-breath intervals to create a waveform; performing the Fourier transform, performing the autocorrelation function, and/or calculating the power spectral density of the waveform; determining whether there are significant peaks of the Fourier transform, the autocorrelation function, and/or the power spectral density of the waveform; and determining that if significant peaks exist, the breathing is irregular and periodic, or any combination thereof. The assessment can also include interpolating between these breath-to-breath intervals to create a waveform; identifying peaks of the waveform; determining the time between the peaks; calculating the coefficient of variation of the time between the peaks; determining if the coefficient of variation of the time between the peaks is low, the breathing is irregular and periodic; and determining if the coefficient of variation of the time between the peaks is low, the breathing is irregular and is not periodic, or any combination thereof. In some embodiments, the assessment of whether irregular breathing is periodic comprises one or more of the following: identifying apneaic events; determining the time of cessation of apneaic events; estimating the interval between the cessation of each consecutive pair of apneaic events; determining whether the interval between the cessation of each consecutive pair of apneaic events is consistent by calculating the coefficient of variation of the interval between the events by calculating the coefficient of variation; determining if the coefficient of variation is below a threshold, breathing is periodic; and determining if the coefficient of variation is above a threshold, breathing is irregular and not periodic. In some embodiments, assessment of whether irregular breathing is periodic comprises one or more of the following: calculating the envelope of the respiratory waveform; performing the Fourier transform, performing the autocorrelation function, or calculating the power spectral density of the waveform; and determining whether there are significant peaks of the Fourier transform, the autocorrelation function, or the power spectral density of the waveform. In some embodiments, the envelope is calculated by interpolating between the peak amplitudes, or squaring the signal and applying a low-pass filter.

In some embodiments, features that highlight the core aspects of a breathing signal can be extracted from a database of breaths. In some embodiments, these features can include the inhale time to exhale time ratio, the length of pauses in breathing, the ratio of the length of a pause in breathing to the breathing period, the depth of breath, the inflection points of the breath, and/or the mean, variance and kurtosis of the breath, or any combination thereof. In some embodiments, these features can include particular coefficients in the wavelet decomposition of the signal or particular coefficients of the Fourier transform of the signal. In various embodiments, the same features extracted from the database of breathing signals can be again extracted from the new signal being considered. In some embodiments, the new signal features can be compared to the database of features, and if a match is found, then the signal can be labeled as a breath. In some embodiments, the peak of the breath can be identified based on information in the database.

Various embodiments of the respiratory regularity assessment algorithm can determine whether irregular breathing is periodic. In various embodiments, one or more of the following methods can be used to determine whether irregular breathing is periodic:

Interpolate between the breath-breath interval calculations (with the data set encompassing the length of the interval vs. time, with the time point at the end of the breath for which the interval in which it was calculated) and perform the Fourier transform and/or calculate the power spectral density of the resulting waveform. Determine if it has a significant periodic component.

Interpolate between the breath-breath interval calculations (with the data set encompassing the length of the interval vs. time, with the time point at the end of the breath for which the interval in which it was calculated) and perform an autocorrelation. Determine if it has a significant periodic component.

Interpolate between the breath-breath interval calculations (with the data set encompassing the length of the interval vs. time, with the time point at the end of the breath for which the interval in which it was calculated) and determine peaks of the resulting waveform. Determine if the difference between the peaks is consistent by calculating the coefficient of variation of the difference between the peaks and determining whether it is low enough to indicate periodic breathing.

Identify the cessation of apneaic events, and determine the cessation-of-apnea to cessation-of-apnea intervals. Determine whether the difference between the cessation of apneas is consistent by calculating the coefficient of variation of the difference between the events and determining whether it is low enough to indicate periodic breathing by comparing to a threshold.

Identify the cessation of apneaic events, and determine the cessation-of-apnea to cessation-of-apnea intervals. Calculate the average time difference between the cessation of apneas as the cycle length of periodic breathing.

Figure 8A:
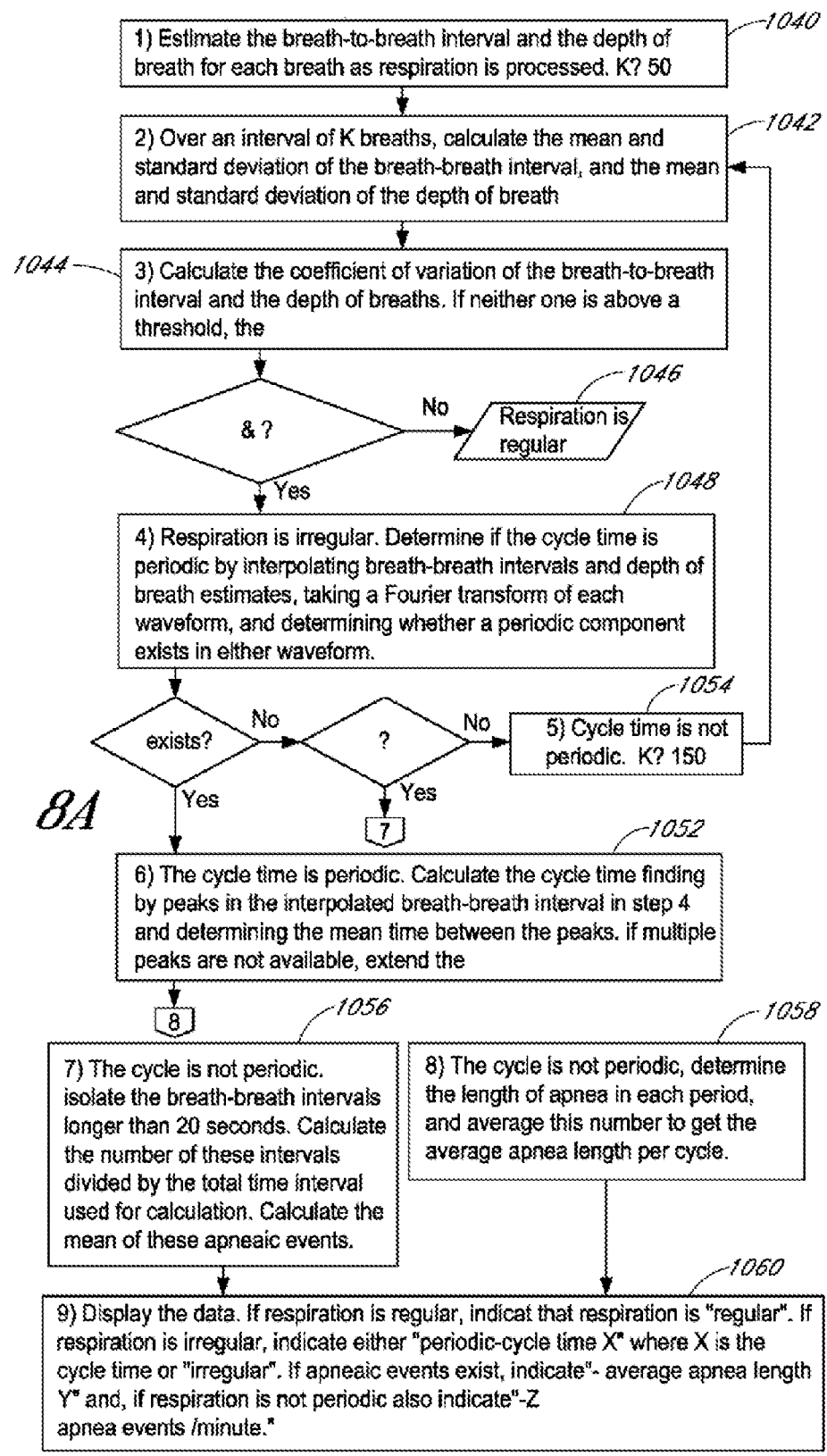
FIG. 8A illustrates an embodiment of an algorithm to assess the regularity of respiration.

FIG. 8A illustrates a flow chart of a method that is used to assess the regularity of respiration. The method can comprise one or more of the following operations:

1. Estimate the breath-to-breath interval and the depth of breath for each breath as respiration is processed as shown in block 1040.
2. Over an interval of 50 breaths, calculate the mean and standard deviation of the breath-breath interval, and the mean and standard deviation of the depth of breath as shown in block 1042.
3. Calculate the coefficient of variation of the breath-to-breath interval and the depth of breath as shown in block 1044. If neither one is above a threshold, the respiration can be considered regular as shown in block 1046. If the coefficient of variation of either the breath-breath interval or the depth of breath is above a threshold, the respiration can be considered irregular as shown in block 1048, and additional processing is performed. In some embodiments, the threshold can be 25%.
4. If the respiration is detected as irregular, determine whether the cycle time is periodic by interpolating between breath-breath intervals and depth of breath estimates, taking a Fourier transform of each waveform, and determining whether a periodic component exists in either waveform as shown in block 1048. If a periodic component exists in at least one of the waveforms, the cycle time can be indicated as periodic as shown in block 1052. If a periodic component does not exist in either waveform, the cycle time is not indicated as periodic as shown in block 1054.
5. If the cycle time is not indicated as periodic, repeat operation 2 with a longer interval of breaths (150 breaths). If the cycle time is still not indicated as periodic, skip to operation 7.
6. If the cycle time is indicated as periodic, calculate the cycle time finding by peaks in the interpolated breath-breath interval in operation 4 and determining the mean time between the peaks as shown in block 1052. If multiple peaks are not available, extend the interval used for this operation.
7. If the cycle is not indicated as periodic, isolate the breath-breath intervals longer than 20 seconds as shown in block 1056. Calculate the number of these intervals divided by the total time interval used for calculation. Calculate the mean of these apneaic events.
8. If the cycle is indicated as periodic, determine the length of apnea in each period, and average this number to get the average apnea length per cycle as shown in block 1058.
9. Display the data as shown in block 1060. If respiration is detected as regular, indicate that respiration is "regular". If respiration is detected as irregular, indicate either "periodic—cycle time X" where X is the cycle time or "irregular." If apneaic events exist, indicate "– average apnea length Y" and, if respiration is not periodic also indicate "–Z apneaic events/minute."

Figure 8B:
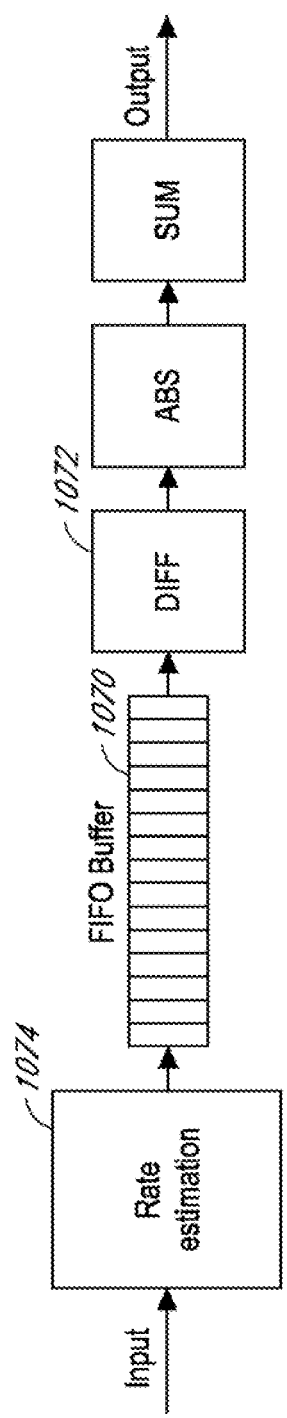
FIG. 8B illustrates a system configured to determine the regularity of respiration.

In some embodiments, the following algorithm can be used to provide indication of irregularity. Rates calculated by the rate estimator 1074 can be stored in a FIFO buffer 1070 of length N, where N is an integer. N can represent the amount of data used to calculate the irregular breathing index. The sum of the absolute value of the differences of the rate values stored in the FIFO buffer 1070 can then be taken, as shown in FIG. 8B. For elements 1 to N of buffer x, the block DIFF 1072 will return [x2–x1 x3–x2 . . . xn–xn–1]. The output of this calculation can be the irregular breathing index. This index can then be compared with a predetermined threshold such that if the irregular breathing index is greater than the threshold, a subject's respiratory pattern can be considered irregular.

Obstructive apnea can be defined as an 80-100% reduction in airflow signal amplitude for a minimum of 10 seconds with continued respiratory effort. The rib cage and abdomen can move out of phase as the patient tries to breathe, but the airway can be blocked. A quadrature Doppler radar system, such as the one described above, can monitor this paradoxical breathing based on the complex constellation due to the target's chest and abdomen motion. Since a human's physiological signal such as breathing is a very narrow band signal (less than 1 KHz) compared to the radar carrier signal, all the reflected signals will be phase modulated on a coherent carrier signal. Therefore, if human body parts, for example the chest and abdomen, are expanding or contracting simultaneously, the received reflecting signals from different paths (reflecting from different body parts) may only shift the phasor of the carrier signal but not the phase modulated narrow band carrier signals. Shift of the phasor of phase modulated narrow band carrier signals can also occur when different body parts are moving at the same frequency but with different amplitude or phase delay, as is the case in paradoxical breathing. Consequently, in the former case, the shape of the complex plot at the baseband due to the respiration may not change and can form a fraction of a circle (an arc) which can be similar to the one from the a single source, while in the latter case the phasor of the baseband signal changes during the periodic motion (such as breathing), resulting in distortion of the complex constellation. This fact can be used to detect paradoxical breathing.

The paradoxical factor can be calculated as the ratio of the largest eigenvalue to the second largest eigenvalue multiplied by the ratio of the maximum amplitude of the signal projected on the principal vector to the maximum amplitude of the signal projected onto the vector orthogonal to the principal eigenvector. A cost function can convert the paradoxical factor to a paradox indicator, which can be used to indicate paradoxical breathing.

The input to the cost function can be the paradoxical factor and the cost function can transform the paradoxical factor to a value which is between 0 and 1. In some embodiments, the cost function can be represented by the following equation $$\text{Cost(input)} = \frac{1}{v \times \sqrt{2\pi}} \int_{x1}^{x2} \exp\left(\frac{-(\text{input}-m)^2}{2 \times v^2}\right) dx,$$

where x1, x2 can represent a range of the paradoxical factor, which can be 0 and 1, while m and v can represent boundary input values between paradoxical and non-paradoxical and v can represent emphasizing factor of paradoxical factor. For example, if m is close to x1 then paradoxical indicator threshold can be set to lower paradoxical factor. On the other hand, as v increases paradoxical indicator can changes more dramatically as paradoxical factor changes. If the paradoxical indicator is near one, it can be likely that there is paradoxical breathing; if the paradoxical indicator is near zero, it can be unlikely that there is paradoxical breathing. A threshold can be set on the paradoxical indicator to provide a yes/no output, or two thresholds can be applied to achieve a green-yellow-red output corresponding to likely paradoxical breathing, uncertain output, and unlikely paradoxical breathing.

In one embodiment, m can be set to approximately 0.3 and v can be set to approximately 0.04.

In some embodiments, the realization of respiration cessation monitor can be based on estimating the relative amplitude of the breathing waveform during the times of no motion artifact. The amplitude samples can be used to create a histogram which can then be used to determine the threshold for cessation of breath.

Figure 16:
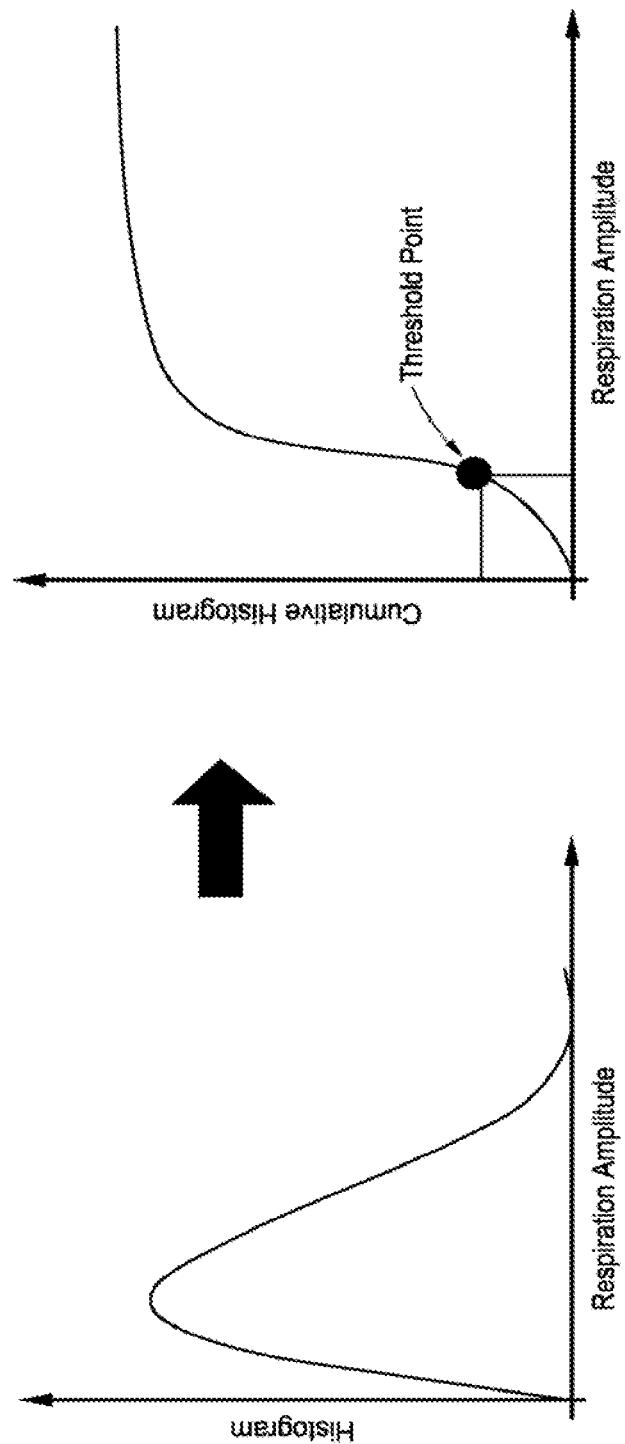
FIG. 16 graphically illustrates a respiration amplitude histogram, a cumulative histogram and a threshold point used in detection of cessation of breath.

In some embodiments, the method for realization can include one or more of the following:
1. Determine the time spans of no motion (fidgeting or activity). On the time spans that are more than L1 seconds, perform the following, with sample results shown in FIG. 16:
   a. Calculate the instantaneous amplitude (envelope) vs. time of the breathing signal by squaring the signal and passing it through a moving average filter of length L2 seconds.
   b. Generate the cumulative histogram of the amplitude obtained in a.
   c. Set the thresholds for low breathing amplitude based on the cumulative histogram.
   d. Within the 'no motion' time span, find apnea timespans as those when the instantaneous amplitude drops below the threshold.
2. Report the timestamps of the apneic events obtained from (a)-(d) and redo the operation for the next time span.

VI. Multi-Parameter Vital Signs Measurement Systems

In various embodiments, the nasal/oral airflow sensor can provide either an indication of whether the patient is breathing, and/or, with a more advanced sensor, an estimate of the velocity of the airflow. A number of respiratory events, such as non-respiration and/or reduced respiration events, can be detected based on the data generated by such sensors. For example, this data can be used to accurately detect apnea, and with the more advanced sensors, it can also be used to detect hypopnea (reduction in airflow). An accurate measurement of airflow can be useful in determining whether an event is a hypopnea or an apnea. The nasal/oral airflow sensor can include one or more thermistors, hot-wire anemometers, pressure sensors, or any combination thereof. In some embodiments, a nasal/oral airflow sensor can be provided to measure the air flow through each nostril and the mouth independently. In a number of embodiments, an airflow sensor alone may encounter difficulties determining whether an apnea is central or obstructive.

Figure 4A:
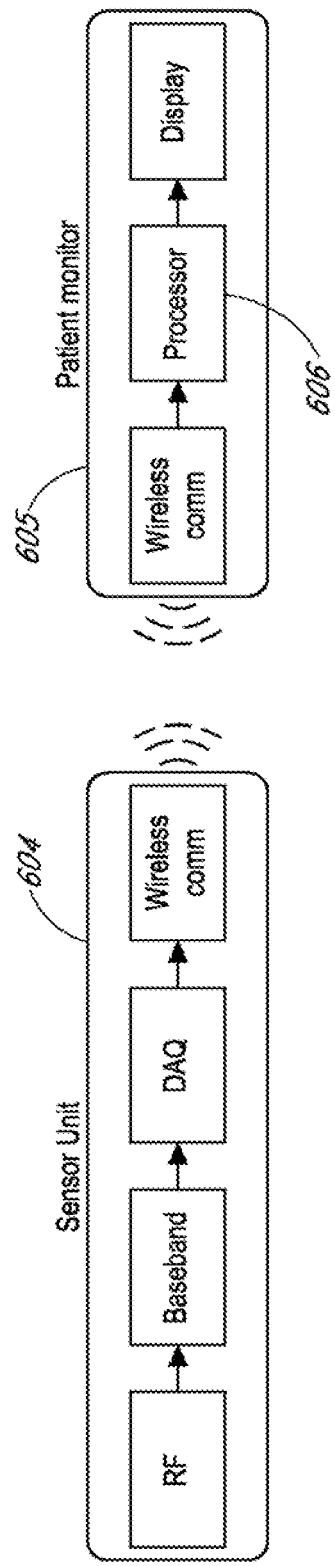
FIGS. 4A-4B schematically illustrate various embodiments of a radar-based physiological motion sensor that is configured to wirelessly communicate with a patient monitor.

As shown in FIG. 4A, some embodiments of the system 100 can include a sensor unit 604 that is wirelessly linked with a patient monitor 605. The patient monitor 605 can be located in any suitable location. For example, in some embodiments, the sensor unit 604 can be located in relatively close proximity to the patient monitor 605, such as in the patient's room. The system 100 can be configured to wirelessly transmit the digitized signals from the sensor unit 604 to the patient monitor 605 in the patient's room and/or in other locations. The patient monitor 605 can include a processing unit 606 that can be configured to process the signals from the sensor unit 604. The processing can include, but is not limited to, DC compensation, filtering, demodulation, motion-detection, rate-finding, possible calculation of other variables, or any combination thereof.

Figure 4B:
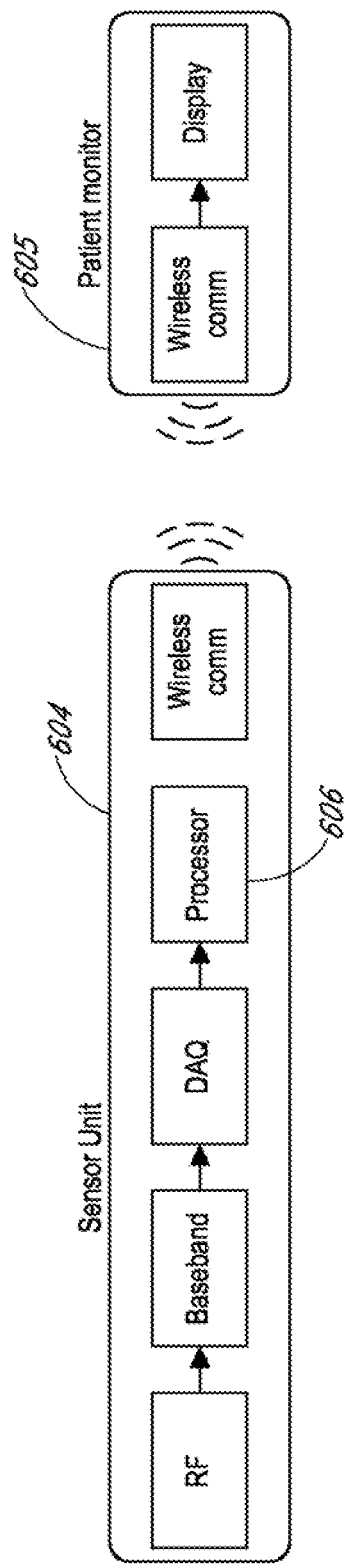

As illustrated in FIG. 4B, in various embodiments, the sensor unit 604 can include the processing unit 606 and associated digital components such that the sensor unit 604 is configured to process the digital signal, including perform DC compensation, filtering, demodulation, and/or motion detection, and transmit a processed signal to the patient monitor 605. In various embodiments, the processing unit 606 in the sensor unit 604 can be configured to perform rate estimation and/or calculation of other respiratory variables, or, alternatively, the patient monitor 605 can perform rate estimation and/or calculation of other respiratory variables from the processed signal. In those embodiments in which the patient monitor 605 is configured to perform rate estimation, the patient monitor 605 can use the same rate-estimation algorithm used for other respiratory waveforms it can input, including, for example, impedance pneumography.

Figure 5:
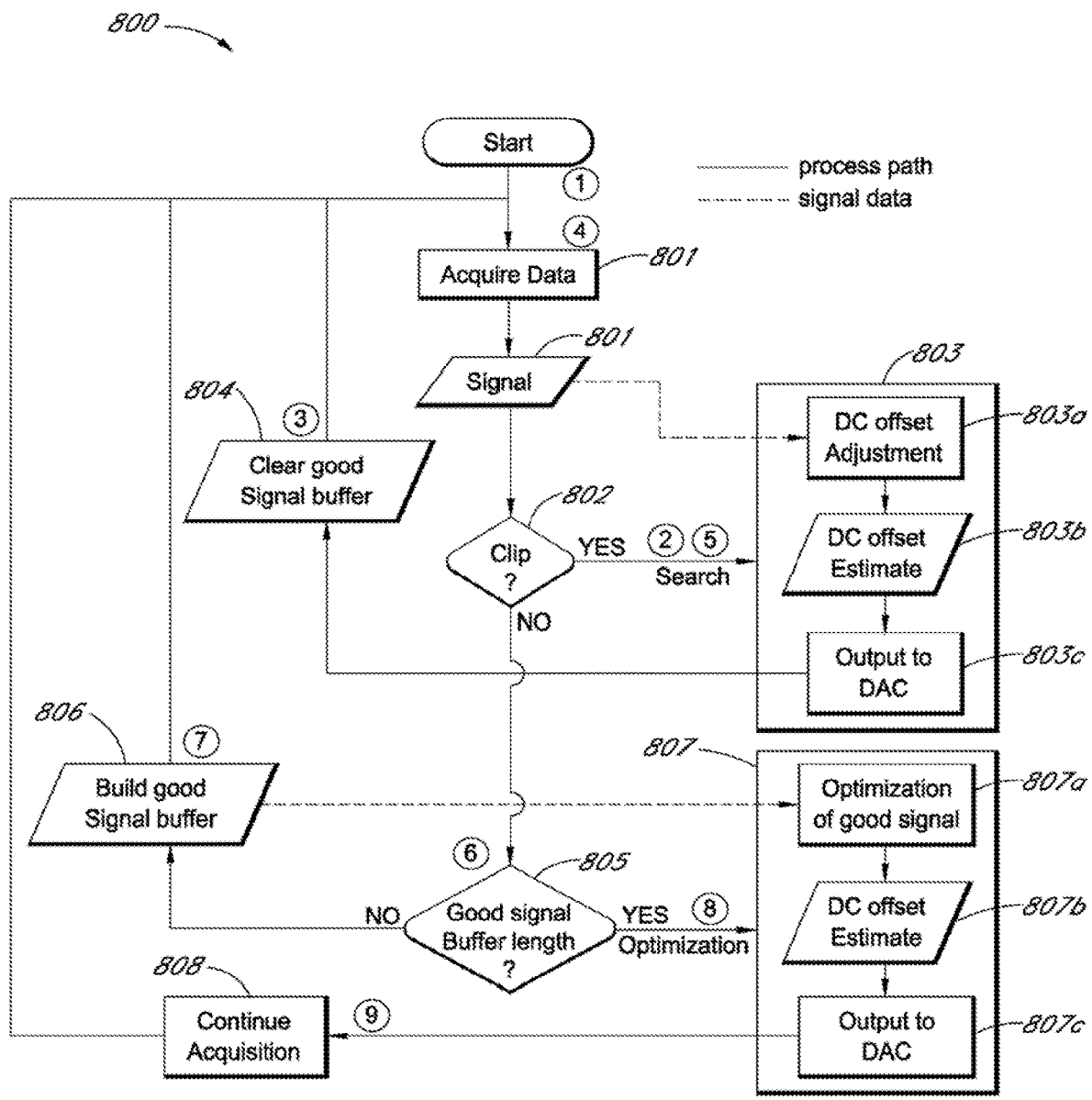
FIG. 5 illustrates a flowchart of an embodiment of a method configured to perform DC cancellation.

FIG. 5 illustrates a flowchart of an embodiment of a method for performing DC cancellation 800. At the beginning, an analog-to-digital converter (ADC) can acquire the motion signal obtained by transforming the Doppler shifted received signal as shown in block 801. If in block 802, it is determined that the signal is being clipped, then the method can proceed to block 803. In block 803, the estimated DC offset can be adjusted depending on at least one or more of the following factors: gain of the system, input range of the ADC and various other factors as shown in blocks 803a and 803b. The estimated DC offset value can be output to a digital-to-analog converter (DAC) as shown in block 803c. A good signal buffer configured to store continuously acquired signal that has no clipping or negligible clipping can be cleared as shown in block 804, the method can return to block 801 and the signal is re-acquired.

Figure 13:
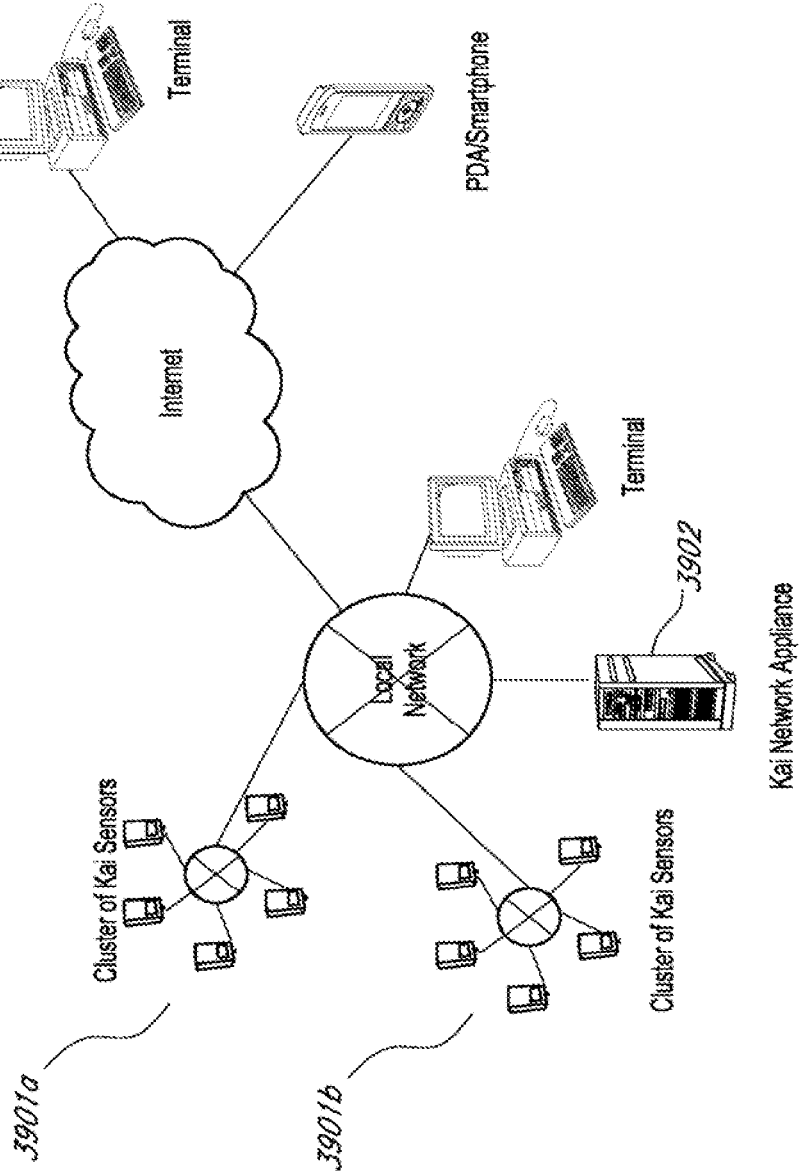
FIG. 13 illustrates an embodiment of a network topology of a plurality of clusters that include radar-based physiological motion sensors.

In various embodiments, a sensor network including a plurality of "thin" cardio pulmonary sensors can work in conjunction with a centralized processing appliance. FIG. 13 illustrates a centralized topology such that a plurality of "thin" non-contact cardiopulmonary sensors form clusters 3901a and 3901b. In some embodiments, the clusters 3901a and/or 3901b can include at least 2, 3, 4, 5, 6, 7, 8, 9, 10, or even more sensors. The sensor clusters can be controlled by a network appliance 3902 where all or substantially all processing can take place. Embodiments of this topology can be useful where sensors can be deployed in a relatively dense area (for example, one per hospital bed). In this case, rather than having each sensor be a full fledged cardio pulmonary monitor, each sensor may only possess minimal hardware, in some embodiments, only enough for data acquisition and forwarding a data stream. In various embodiments, each sensor can include a data acquisition module and a network module. Data can be transferred from one or more devices in the clusters 3901a and/or 3901b via a network, such as a local network, intranet, the Internet, or any combination thereof. In various embodiments, raw data can be streamed to the network appliance 3902 where further processing can be performed. In various embodiments described above, the system can process the raw data internally. In various embodiments, processing can include the demodulation of the IQ channels, any DOA processing for tracking, respiration rate, etc. In various embodiments, the calculated statistics and processed data can then be stored on the network appliance 3902 and/or they can be forwarded to an electronic health record server and/or other non-transitory computer memory. A remote client can then access this data via any suitable electronic device, such as a computer, tablet computer, mobile phone, PDA, etc. The data can also be viewed via a terminal locally and/or remotely in various embodiments. FIG. 39B shows an alternate embodiment of FIG. 13 showing the direction of information flow between the sensor cluster 3901a, the network appliance 3902 and various other components of the network.

Patient monitoring devices can be used in medical settings to monitor a patient's physiological waveforms, including, but not limited to, electrocardiogram, respiratory effort, respiratory airflow, pulse, blood oxygenation as well as vital signs, including but not limited to heart rate, pulse rate, respiratory rate, blood oxygenation, end-tidal CO2, or any combination thereof. Vital signs measurement devices can be used in medical settings to measure a patient's vital signs at a point in time and/or at regular intervals, including, but not limited to heart rate, pulse rate, respiratory rate, blood oxygen, temperature, end-tidal CO2, blood pressure, or any combination thereof. Some embodiments are directed to a Doppler radar-based device that provides a non-contact sensor of physiological motion that is integrated into a patient monitoring device and/or a vital signs measurement device. The physiological motion signal obtained with the Doppler radar-based device can be analyzed to provide one or more of: respiratory rate, heart rate, other respiratory parameters, other heart parameters, and physiological signatures, including, but not limited to, respiratory pattern and heart pattern. These signatures may be used to determine the physiological state of the subject, which may be used for medical applications. The device can distinguish valid measurement of heart and respiratory activity, and provide continuous, point in time, intermittent and/or piecemeal data from which rates, signatures, and key variations can be recognized. This device can operate with no contact and can operate at a distance from a subject. The device can operate on subjects in any position, including lying down, reclined, sitting, or standing.

Non-contact physiological motion sensors, according to some embodiments, may be used to obtain respiratory rate, heart rate, and/or physiological waveforms that can be analyzed to help assess the physiological state of the measurement subject. The physiological information may be used for many applications, including but not limited to various medical applications.

Embodiments of the device operate with no contact and work at a distance from a subject. The device can operate on subjects that are in any position, including lying down, reclined, sitting, or standing. The device can operate at various distances from the subject, from, for example, approximately 0.1 to 4.0 meters.

In some embodiments, the device can be positioned in various locations relative to the subject, including but not limited to, in front of the subject, behind the subject, above the subject, below the subject, to the side of the subject, or at various angles to the subject.

In some embodiments, physiological waveforms that may be obtained include, but are not limited to, respiratory effort, chest wall movement due to the underlying heart, peripheral pulse movement, or any combination thereof. Information derived from these waveforms may include, but is not limited to, one or more of the following:

Respiratory
Rate
Inhale time
Exhale time
Inhale time to exhale time ratio
Frequency, depth, and length of gasps
Frequency, depth, and length of sighs
Depth of breath
Degree of paradoxical breathing
Tidal volume
Abdominal excursion to chest excursion ratio
Harmonic content of breathing signal
Shape of the breathing waveform
Heart and pulse
Average Rate
Beat-to-beat interval
Heart Rate Variability
Blood pressure
Pulse transit time
Cardiac output
Other
Correlation between heart and respiratory rates or waveforms
Frequency, duration, and amount of activity
Frequency, duration, and amount of fidgeting or restlessness In some embodiments, the variability of these variables in various frequency bands can also be subject to analysis, including heart rate variability and respiratory rate variability, but also variability of changes of the shape of the heart and/or respiratory waveform, changes in the depth of breathing, and changes in the degree of paradoxical breathing. These may be monitored at specific times related to questions being asked, statements being made, and/or specific tasks being performed. Alternatively or additionally, they may be monitored in subjects going about their normal activities.

In some embodiments, the device can distinguish valid measurement of motion related to heart and/or respiratory activity as distinct from other detected motion of the subject being measured and from motion of the background.

In some embodiments, the Doppler radar-based device operates as a standalone unit, and can simply be co-mounted with the vital signs measurement device and/or patient monitoring device. In some embodiments, the Doppler radar-based device is capable of operating as a standalone unit, but communicates its outputs to the vital signs measurement device and/or patient monitoring device. In some embodiments, the Doppler radar-based device is capable of operating as a standalone unit, but it is controlled by and communicates its outputs to the vital signs measurement device and/or patient monitoring device. In some embodiments, the Doppler radar-based device does not have a user interface and is typically used in conjunction with the vital signs measurement device and/or patient monitoring device, which can control the device and communicates the outputs of the device to the users.

In some embodiments, the Doppler-radar based device is self-contained, with the antennas, radio components, digitization, and processing contained in the sensing unit. In some embodiments, the processing is performed on a separate circuit board that is included in the vital signs measurement device and/or patient monitoring device. In some embodiments, the processing is performed on one or more processors in the vital signs measurement device and/or patient monitoring device that is used to process information related to other physiological measurements as well.

In some embodiments, the cable that connects the Doppler radar-based device to the vital signs measurement device and/or patient monitoring device is a USB cable. In some embodiments, a custom cable connects the Doppler radar-based device to the vital signs measurement device and/or patient monitoring device. In some embodiments, the cable is captive in the Doppler radar-based device, and in some embodiments, the cable can be plugged into and removed from the device. In some embodiments, the Doppler radar-based device is powered over the same cable that provides communications connectivity. In some embodiments, separate cables are used for power and communication.

The Doppler radar-based device can cause data to be transferred between a variety of electronic devices. In some embodiments, the Doppler radar-based device may communicate its outputs to the central nurses' station. In some embodiments, the Doppler radar-based device may communicate its outputs to personal digital assistants (PDAs) and/or cellular phones, such as smart phones, that have been programmed to receive the results. In some embodiments, the Doppler radar-based device may communicate its outputs to a Doctor's office. In some embodiments, the Doppler radar-based device may be controlled by any suitable electronic device, for example, from a central nurses' station, personal digital assistants, cellular phones, a computer at a Doctor's office, or any combination thereof.

In various embodiments, the Doppler radar-based device may communicate wirelessly with a protocol such as WiFi, Bluetooth, Zigbee, and/or via cellular networks to another device, such as a patient monitoring device and or a vital signs measurement device, and/or to a central station, computer, or database. In some embodiments, the Doppler radar-based device may communicate results to a central database and/or computer, which in turn communicates the results to a patient monitoring device and/or a vital signs measurement device that is configured to monitor the same patient.

In some embodiments, raw data may be streamed from the sensor to one or more central computing devices and processed in the one or more central computing devices. In some embodiments, some or all of the processed data and other outputs of the processing may be stored on the one or more central computing devices. In some embodiments, some or all of the processed data and other outputs of the processing may be streamed back to a device that is local to the patient or nurse for display. In some embodiments, the device that is local to the patient or nurse may be the Doppler radar-based device. In some embodiments, the device that is local to the patient or nurse may be a vital signs measurement device and/or patient monitoring device. In some embodiments, the device that is local to the patient or nurse is a tablet PC. In some embodiments, the device that is local to the patient or nurse is a monitor configured to display various physiological and vital signs parameters.

In some embodiments, the same radio that is used for Doppler radar-based sensing can also be used for communications with other local devices or central systems.

In some embodiments, the outputs of the Doppler radar-based device can be forwarded from device to device until reaching a central system.

The Doppler radar-based device can advantageously be faced towards the patient for a measurement. In various embodiments, the Doppler radar-based device may be mounted with the vital signs measurement device and/or patient monitoring device in a number of ways, including mounting directly or indirectly to the cart that the vital signs measurement device and/or patient monitoring device is on, mounting directly or indirectly to the vital signs measurement device and/or patient monitoring device, mounting to the bed rail, mounting to the ceiling, mounting to the wall, mounting to another pole, and/or mounting to the foot of the bed.

In some embodiments, the mounting mechanism may have a quick-release mechanism so it can be moved from one mounting position to another. In some embodiments, the mounting may be magnetic, such that it can attach to any metallic surface. In some embodiments, the mounting may be magnetic, such that it can easily attach to any mounting designed to mount with it. In some embodiments, the mounting may include a suction cup. In some embodiments, the mounting may include a clamp. In some embodiments, the mounting may include a quick release plate on the Doppler radar-based sensor and a mating piece on the mounting point.

In some embodiments, the mounting may be easy to move into a number of different positions. In some embodiments, the mounting may include a goose neck. In some embodiments, the mounting may include a universal joint. In some embodiments, the mounting may include a semi-rigid tube. In some embodiments, the mounting may include a grip such that when the grip is squeezed, the sensor may be moved into a number of different positions, but when the grip is released, the sensor can be locked into a current position.

In some embodiments, the device may be connected directly or indirectly to the patient monitoring device and/or vital signs measurement device. In some embodiments, this connection may be via a universal joint.

In some embodiments, the mounting between the patient monitoring device and/or vital signs measurement device may be configured such that when the device is properly mounted, the power and communications are automatically configured such that no additional cables are necessary. In some embodiments, this mounting can include a locking socket with a USB connection over which power and communications can be configured. In some embodiments, the mounting can include inductive power and communication can be performed wirelessly, such that the unit can perform all or substantially all communication wirelessly. In some embodiments, a battery is included in the mounting hardware, and this battery can power the Doppler radar-based device.

In some embodiments in which the Doppler radar-based device mounts to the same pole as the patient monitoring device and/or vital signs monitor, the mounting may include a pole clamp that clamps to the stand, an arm that reaches around the vital signs measurement device and/or the patient monitoring device and a joint such that the Doppler radar-based device is beside or above the vital signs measurement device and/or the patient monitoring device. In some embodiments, it may be possible to move this mounting from side to side or behind the vital signs measurement device and/or the patient monitoring device. In some embodiments, the arm that reaches around the vital signs measurement device and/or the patient monitoring device may include a telescoping pole such that the Doppler radar-based device may be moved up and down relative to the vital signs measurement device and/or the patient monitoring device. In some embodiments, the arm that reaches around the vital signs measurement device and/or the patient monitoring device may include a sliding track such that the Doppler radar-based device may be moved up and down relative to the vital signs measurement device and/or the patient monitoring device.

In some embodiments, the mounting for the Doppler radar-based device may be a tension-balanced arm that can be moved to any position. In some embodiments, the mounting for the Doppler radar-based device may be a hinged arm similar to that of a desk lamp.

In some embodiments, the mounting arm may be powered, utilizing a screw, hydraulics, cables, and/or a motor to automatically move the Doppler radar-based device into position.

In some embodiments, the Doppler radar-based device may automatically face towards the subject using beam steering, direction of arrival algorithms, a motorized rotation, or any combination thereof. In some embodiments, the optimum direction may be estimated by sensing the direction and/or relative position of a thermometer, arm cuff, or other part of the patient monitoring device and/or vital signs measurement device that is configured to contact the patient during a measurement. In some embodiments, there may be a physical attachment between the arm cuff and the Doppler radar-based sensor unit such that this attachment pulls the device towards the patient to aim the device.

In some embodiments, a custom bed frame may be used that the sensor can easily mount to.

In some embodiments, the Doppler radar-based device can be permanently mounted in the bed or on the ceiling and/or wall and communicates with a central station and/or a local vital signs measurement device and/or patient monitoring device.

In some embodiment, Doppler radar-based devices that include the ability to read RFID tags may be placed throughout the hospital such that they can track the location of patients and measure the patients vital signs as they move throughout the hospital.

In some embodiments, a totally wireless unit can be implemented by providing wireless power and wireless communications.

In some embodiments, the device is solar powered. In some embodiments, the device is powered kinetically.

In various embodiments, the device's display may be co-located with the radar unit, or it may be separate such that the orientation and/or position of the display may be changed independently of that of the radar unit. In various embodiments, the device may use the display of an associated vital signs and/or patient monitoring device. In various embodiments of a spot check device, which can display a point-in-time respiratory rate, it may be possible to alternate between the respiratory rate and the respiratory waveform used to obtain the rate. In embodiments that utilize a touch-screen, this may be achieved by touching the number where the rate is displayed. Alternatively, a separate button may be used to toggle between the rate and the trace, or waveform. In various embodiments, it may be possible to zoom in and out on the waveform or trace. In various embodiments, the zoom may utilize a multi-touch screen. In various embodiments the zoom may utilize zoom in and zoom out buttons.

In various embodiments, a waveform may be displayed and the user may select the portion of the waveform to use to determine the rate in a spot check scenario. In some embodiments, the real-time waveform may be continuously displayed and the user may touch a button to freeze the waveform and select an interval in which to determine the rate. In some embodiments, the waveform can un-freeze after a pre-determined time.

In various embodiments, when the waveform associated with a spot check is displayed, the device may display only the portion of the waveform used to obtain the rate (possibly with portions with motion removed), it may display the full obtained waveform with the portion of the waveform used to obtain the rate highlighted. In some embodiments, the waveform display may include dots on peak inhalations used to obtain the rate or other parameters.

In various embodiments, the device may allow the user to manually input a counted rate.

In various embodiments, the device may have a button or touch screen that the user hits at each peak inhalation, and the device estimates a respiratory rate based on the peak inhalation times indicated by the user.

In various embodiments, the height of the wave form on the screen may auto scale such that the user can see the most detail. In various embodiments, the height of the waveform on the screen may be absolute or to scale, such that the user may adjust the aiming of the device to make the waveform amplitude higher. In various embodiments in which the depth of breath is calculated, the height of the waveform on the display may be absolute relative to the depth of breath. In various embodiments, the scale on the x-axis (signal power or depth of breath) and the scale on the y-axis (time) may be selected via the touch screen or via zoon-in or zoom out buttons.

In various embodiments, a histogram of recent breath rates may be displayed. In various embodiments, the number of recent breath rates or the amount of time included in the histogram may be selected by the user. In various embodiments the histogram display may be selected by pressing a button on the device.

In various embodiments, the device may display trends in the respiratory rate on a graph that has the rate on the y-axis and time on the x-axis. In various embodiments, the device may also indicate the mean and standard deviation of the rate. In various embodiments, the device may indicate the mean and standard deviation of the rate by shading a bar that fills the area between the mean plus one standard deviation and the mean minus one standard deviation.

In various embodiments the device, the associated patient monitor, vital signs device, or any combination thereof may calculate and display an integrated respiratory status index or an integrated patient health index.

In various embodiments, the device may determine a baseline rate and provide information about changes in the rate from the baseline rate. In various embodiments, the device may request the user to enter the baseline rate and then provide information about changes in the rate from the baseline rate obtained from the user.

In various embodiments, the device may provide the percentage change and/or absolute change in rate and/or average rate from measurement to measurement and/or at specific time intervals.

In various embodiments, trends in the respiratory rate and/or other physiological variables may be displayed using Sparklines. Sparklines for respiratory rate may include the words "respiratory rate" or "respiration rate", a number indicating the most recently measured respiratory rate value, a line showing the path of the most recent readings or measurements of respiratory rate, a band showing the normal range of respiratory rate, or any combination thereof. In various embodiments, a dot may be placed on the most recent value, and this dot may be color coordinated with the number indicating the most recent respiratory rate reading. In various embodiments, the normal range of respiratory rate may be based on population averages or may be specific to the patient being measurement. In various embodiments, the normal range of respiratory rates may be based on values entered by the user for the patient being measured. In various embodiments, the normal range of respiratory rates may be based on patient history.

In various embodiments, the display may highlight features of interest, including changes in the waveform, inhale-time to exhale time ratio, or rate of breathing.

In various embodiments, the device may detect whether or not the subject is sleeping. In various embodiments the sleep state may be included on the display and in the historical data.

In various embodiments the device may detect and display heart rate in addition to respiratory rate.

In various embodiments the device may display an activity index. In various embodiments the activity index may be calculated from the amount of motion occurring over time.

In various embodiments, the device may automatically reposition and/or electronically steer the radio beam to track a patient. In various embodiments, the device may reposition and/or electronically steer the radio beam after each motion event. In various embodiments the device may reposition and/or electronically steer the radio beam at predefined intervals.

In various embodiments, the device may include a camera that can be used for aiming the device. In various embodiments, the device may include a display that shows the camera image such that when the patient's torso fills the display, the user knows that the device is positioned properly. In various embodiments, a silhouette or outline of a body may be included in the display to help with aiming. In various embodiments, the device may include a camera and use image recognition software to determine the patient positioning and/or the patient orientation. In various embodiments, the device may use image recognition to determine motion of the subject. In various embodiments the device may utilize image recognition software determining the patient position or orientation to provide feedback on aiming and/or to automatically reposition the device or perform electronic beam steering.

In various embodiments, different measurements, indicators, or methods of display may be displayed in different sections, such as quadrants or sextants, of the screen, and by touching one section, the selected section can expand to full screen. In various embodiments, it may be possible to change the orientation of windows including different measurements, indicators, or methods of display, including but not limited to columns, quadrants, and rows.

VI. Patient Identification Tag

In various embodiments, the desired target can wear a tag that can be used for aiming and/or identification of the desired target. In some embodiments, the signal strength from the tag can be used to aid with aiming or otherwise positioning one or more elements of a system. In some embodiments, a tag can be used in conjunction with DOA processing to determine the direction of the tag and to focus the receive beam of a multiple-receiver system in this direction. In some embodiments, the tag can provide a harmonic of the transmitted signal or a modulated version of the transmitted signal. In some of these embodiments, the signal can be obtained from the tag signal rather than the overall Doppler signal, to ensure that the signal comes from the desired source. In some embodiments, a retro-directive antenna can send the signal back in the same direction using a phased array or corner antennas.

In various embodiments, an identification (ID) system can be configured to provide positive patient identification in conjunction with remote vital signal sensing as illustrated in FIG. 16C. Various embodiments of an ID system can include two basic components: a reader 1610 and a tag 1612. The tag 1612 can be a device placed on or near the patient that emits and/or re-emits a signal. Emitted and/or re-emitted signals can be modulated in such a way that the signals are encoded with unique identification that marks that signal as being from a specific tag. In some embodiments, this unique identification indicates a patient identification number that corresponds to a patient identifier used in medical records. The reader 1610 can be a device that receives the modulated signal from the tag 1612 and identifies the coded information. In some embodiments, the reader 1610 can also provide the source signal that the tag 1612 can be configured to modulate and re-emit. In order for an identification system to link the vital-sign assessment to a particular patient, it can be sufficient to ensure that the patient is located within the area in which the direction-sensitive and range-sensitive sensor can measure. For example, some direction-sensitive and/or range-sensitive sensors can obtain reliable measurements within a radius of no more than about 1,000 feet, 500 feet, 200 feet, 100 feet, 50 feet, 25 feet, or 10 feet. In some embodiments, direction sensitivity in a remote-sensing radar can be achieved through use of a directional antenna that can be insensitive and/or unresponsive to signals outside of a limited angle range in two dimensions. For example, the limited angle range can be less than about 270, 240, 210, 180, 150, 120, 90, 60, 45, 30, 20, 15, 10, or less degrees. In various embodiments, range sensitivity can be limited through power sensitivity and/or range-gating of pulse signals. A location-specific ID system can typically have an active area within of this three dimensional space of sensor sensitivity.

In some embodiments, the tags can be encoded with a patient identification number and/or another unique identifier of the patient. In some embodiments, the vital signs monitor can access patient information (such as name, etc.) based on information obtained from this tag and display patient information for the patient being measured on the display. In some embodiments, the vital signs monitor can transmit vital signs information with the patient identification number such that in a central nursing station, the vital signs are displayed with the patient identification number, and/or such that the vital signs are stored within or associated with the patient's electronic medical record.

In some embodiments, at the initiation of a continuous measurement, the nurse can synchronize the vital signs monitor with the tag worn by the patient, such that the monitor can only monitor, display, transmit, and/or record vital signs when that tag is in the field of view, until a new measurement is initiated, with a new tag.

FIG. 16D shows an embodiment of an active tag 1612 emitting a signal modulated with a unique ID signature that is received by the reader device 1610. In this embodiment, the reader 1610 has a directional antenna that detects the tag's 1612 signal from a specific angle range. In various embodiments, the power of the tag 1612 can be adjusted to limit the range in which the tag can be sensed such that the ID area is the same area sensed by the vital-sign monitor.

FIG. 16E shows a tag 1612 receiving a signal and either re-emitting the signal modulated with unique ID information (passive) or emitting a new signal (active). In various embodiments, in order for the ID to be location specific, the transmit and/or the receive apparatus can be directional. In various embodiments, the tag 1612 can either emit or re-emit in an omni-directional fashion or utilizing a retro-directive method such as a corner reflector or a phased array.

In some embodiments, a signal can be transmitted by an exciter, received by the tag, re-emitted in an omni-directional direction, with the signal modulated by the tag in such a way that there is identifiable information in the signal, and then detected by a receiver. In some embodiments, the tag can reflect the signal back to the source using, for example, a retro-directive array or a corner reflector. In some embodiments, the exciter can be co-located with the receiver. In some embodiments, the exciter and receiver both included within a transceiver architecture. In some embodiments, modulation can include amplitude modulation, phase modulation, frequency modulation, or any combination thereof of the carrier signal. In some embodiments, the tag can return a signal that has orthogonal polarization for linear polarization or counter rotation, for circular polarization. In some embodiments, the tag can return a signal that is a harmonic of the carrier signal. In some embodiments, digital information can be modulated by methods including, but not limited to one or more of: pulse width, pulse delay, pulse amplitude, and pulse density.

FIG. 16F is similar to FIG. 16E in which the tag is configured to receive a signal and emits or re-emits a modulated signal with a unique ID. However, FIG. 16F is a more general form in which the exciter 1614 and the reader 1610 are separate and not necessarily co-located. In this case both the exciter 1614 and the reader 1610 can be directional in order to make the affective area specific to the area sensed by the vital-sign monitor. In some embodiments, the exciter and the reader may not be co-located.

In some embodiments of an active tag, a battery-operated RFID tag can be sensed by a reader with a directional antenna co-located with vital-sign sensor.

In some embodiments, an infra-red LED tag pulses a unique ID, which can be read by an IR-sensitive camera. This camera data can be analyzed to restrict vital-sign sensing to periods when the LED is in a specific area in the camera's view. In various embodiments, the camera can be either ceiling mounted or co-located with the sensor.

In some embodiments, an ultra-sonic tag can be utilized which has a modulated sonic signal at a frequency above that which humans can hear. In some embodiments, ultrasonic microphones can be placed for triangulation to position of tag, and the tag position can be analyzed to indicate whether it is within the range and angle from which the radar-based vital signs sensor can operate.

In some embodiments, the reader is located with the patient and identifies coded information in an RF signal associated with the vital-sign sensor. The reader can respond with an omni-directional signal indicating proper ID acquisition. In various embodiments, this response signal can be in accordance with communication protocols that include, but are not limited to: IEEE 802.11 (wifi), Bluetooth, zigbee, ultra-sonic, infra-red and/or ISM band RF radiation.

In some embodiments, a tag can re-emit RF radiation from the vital-sign sensor's transmitter modulated based on its unique ID. In various embodiments, the reader, with a directional antenna, can be ceiling-mounted, floor mounted, or co-located with the vital-sign sensor. In some embodiments, the reader can have a directional antenna. In some embodiments, the tag can re-emit an omni-directional signal.

In some embodiments, a camera can be mounted on the ceiling or co-located with the sensor, and use facial recognition algorithms to indicate whether the patient is in specific areas of a hospital room before recording vital-signs. In some embodiments, when the healthcare practitioner initiates the measurements, he or she can synchronize the sensor with the face of the patient.

In some embodiments, a camera is mounted on the ceiling or co-located with the sensor, and the patient's tag and/or hospital gown can have a unique pattern that can be deduced by the image-processing algorithms.

Some embodiments of the system can use a Doppler radar-based identification system that can provide positive patient identification while acquiring vital sign signals. In some embodiments, the identification system can provide alternative ways of acquiring physiological signals. FIG. 16G illustrates the concept of enabling positive identification (ID) using a tag attached on the patient. The tag reader, or reader unit 1620, can transmit a continuous wave (CW) signal towards the subject 1622 using a somewhat directive antenna beam illuminating the subject 1622. As the signal is reflected from the subject's thorax, its phase can be modulated proportionally to the thorax's cardiac and/or respiratory motion. When this signal is received and downconverted, there can be a baseband Doppler signal at or around the cardiopulmonary signal frequency. In various embodiments, the ID tag 1624 can be attached to the patient's upper body, either attached to the clothing or adhered to the skin of the patient with an adhesive. In some embodiments, the tag 1624 can be battery operated; however, it can be passive in the sense that it cannot generate transmit signals on its own, but when the signal transmitted by the reader unit 1620 illuminates the tag 1624, the tag 1624 can modulate the backscatter by changing the reflection coefficient from the antenna at a programmed frequency. In some embodiments, the reflection coefficient from the antenna can be changed by periodically connecting the antenna to a load by controlling the bias current of a diode connecting the antenna and a load, resulting in generation of sidebands that carry ID information. In some embodiments, a local battery on the tag can facilitate the periodic connection of the antenna to a load.

One embodiment of the passive transponder RFID technology is shown in FIG. 16H. The illustrated embodiment is a crystal 1632 based two-way radio powered by a watch battery. This tag is passive in the sense that it does not typically generate a signal by itself, however a battery is typically used to power a microprocessor 1626 and provide a modulating current to the diode. The backscatter from the tag can be modulated by the bias current to the diode 1628, which can change the impedance "seen" by the tag antenna 1630, and thus the power reflected from the antenna. The modulating current can be produced by a microprocessor 1626 driven by a low frequency clock, (in some embodiments, the clock is in the 10 kHz range). Thus, the modulated backscatter can appear at the sideband frequency (in some embodiments, in the 10 kHz range), and can be easily separated from the baseband Doppler signal through filtering in the digital domain. The data acquisition sampling rate can advantageously be greater than twice the sideband frequency range (in some embodiments, 20 kHz) to avoid aliasing in accordance with Nyquist's Theorem. In some embodiments in which a low-IF architecture is used, the sampling rate can be selected considering that the sampling rate is preferably at least double the low IF frequency+double the sideband frequency. In some embodiments, the tag antenna 1630 is omni-directional to ensure that the backscatter can be detected by the reader if the subject changes position. In some embodiments, multiple tags can be used to provide signal diversity, for example, on the front and back of the subject, but in other embodiments, only one tag is utilized. In some embodiments, the tag can convey a unique identifier of a patient on carrier signal and/or reflected signal by one of several methods, including but not limited to: frequency modulation, frequency shift keying (FSK), pulse width modulation, and phase shift keying (PSK). In some embodiments, these modulated reflected signals are then demodulated and converted to binary identification numbers.

In some embodiments, unique identifier associated with a patient, such as the patient's ID number, can be encoded on the reflected carrier signal by using conventional modulation methods including but not limited to PSK or FSK modulation. In some embodiments, codes can be set by several bits including pilot bits for both cases. In some embodiments, pilot bits can let the system know the first bit of the patients' ID number and can be consecutive three bits with value one or high. In case of PSK, a fixed offset frequency of more than one cycle can comprise one bit of code bit. In some embodiments, the value of each bit can be assigned by shifting the phase of modulated signal from 0 to 180 degree. In some embodiments using the system illustrated in FIG. 16H, PSK can be achieved by switching the load attached to the antenna via the diode to provide the phase shift. In some embodiments, the bit values can change whenever the current bit phase is 180 degrees different from the previous bit. In some embodiments utilizing FSK, two different frequencies can be used for modulating the reflected signal, one of which represents zero while the other does one. In some embodiment using the system illustrated in FIG. 16H, this can be achieved by switching the diode at the crystal frequency and half the crystal frequency for a fixed period. In other embodiments using the system illustrated in FIG. 16H, four frequencies can be used to provide 2-bit data. In other embodiments using the system illustrated in FIG. 16H, more than 4 frequencies can be used.

In some embodiments, the same radar front-end can be used to detect both the ID information appearing in the sidebands, and the Doppler shift generated by the subject's physiological motion, from the portion of the signal reflected by the thorax and not the tag as shown in FIG. 16I. One difference between the ID information and the Doppler shift generated by physiological is the bandwidth, which can affect the required sampling rate. The sampling rate for the combination radar sensor-ID reader is preferably adequate for detection of the sidebands generated by the tag and for the baseband Doppler shift generated by the subject's physiological motion. After complex down-conversion, the sidebands can appear at a low IF frequency (in some embodiments, this can be in the 10-kHz range—the same or substantially the same frequency as the crystal) that can be digitized and further demodulated in digital domain. The baseband Doppler shift can be near DC, at frequencies below 10-Hz. The baseband signal conditioning can be essentially the same for both the tag reader and the direct-conversion Doppler radar sensor of physiological motion, but in the tag reader system, it may need to accept signals that are sufficiently wideband to include both the baseband Doppler signal and the sidebands generated by the tag. In some embodiments, the signal generated by the tag can have a much lower power than that reflected from the torso, in which case the dynamic range of the receiver is preferably adequate to detect both signals. In various embodiments, this can include one or more of the following methods: AC-coupling the signal to remove DC offsets before amplification and using a high-resolution analog-to-digital converter; applying a method of DC cancellation or DC compensation in analog processing before a high-gain stage and using a high-resolution analog-to-digital converter; separately processing the sideband and the baseband Doppler signal such that each has appropriate gain and filtering; and/or using a high resolution analog-to-digital converter.

In some embodiments, in addition to the identification signals provided by the tag, it is also possible to obtain signals about physiological motion from the Doppler shift of the sideband signals generated by the tag, referred to herein as the sideband Doppler signal. Once the signal is digitized, the sideband signals (those generated by the motion of the tag) can be separated from the baseband Doppler signals (those reflected by the thorax without the tag). In some embodiments, the sideband Doppler signal can be digitally downconverted to baseband, and processed substantially the same way that the baseband Doppler signal is processed. Since the ID tag itself can be attached to the moving surface, signals reflected from the tag antenna can contain a similar Doppler shift as that produced by the moving chest. If there were no modulation on the tag, these two signals would add and it would be challenging to separate them. However, since the tag backscatter can be shifted in frequency by modulating diode bias current, the Doppler shift, as well as the ID information, can appear on these sidebands. Since the modulated backscatter from the tag (sideband Doppler shift) can originate only from the chest region physically attached to the tag, and the carrier Doppler shift results from the illumination of a larger area that can include the hands, arms, shoulders, and legs, it is expected that two signals can exhibit subtle differences. In some cases, the modulated backscatter can be more immune to fidgeting motion, since there can be fewer potential sources of non-cardiopulmonary motion attached to the tag. In some embodiments, the Doppler-shift signal obtained from the tag can be compared with the Doppler shift signal obtained from the non-tag reflections. In some embodiments, significant differences in the two signals can indicate non-cardiopulmonary motion in the signal obtained with the non-tag reflections. In some embodiments, the two signals can be compared with a cross correlation function, and the degree of correlation between the signals can be used to determine whether or not to indicate non-cardiopulmonary motion. In some embodiments, the Doppler-shift signal obtained from the tag reflection can be used for physiological processing. An additional advantage of the sideband signals can be that they typically do not suffer from distortion due to AC coupling, in embodiments where an AC-coupled receiver is used, and they can also be less affected by 1/f noise.

In some embodiments, a desired or designated subject can be continuously monitored within a predefined boundary. For example, the desired or designated subject can be continuously monitored in a home environment or any portion thereof. This can be accomplished, for example, when there is adequate coverage of all rooms with one or more reader and the subject is wearing a tag.

FIG. 16J is a flow chart illustrating an embodiment of the identification-reading and vital signs signals processing of the sideband signals. In this embodiment, the ID code is encoded on the signal by the RFID tag, using fixed-length PSK codes at a fixed offset frequency. In this embodiment, the encoded signal can be modulated on the signal reflected by the RF tag's microprocessor, resulting in a sideband signal offset from the carried frequency by the frequency of the PSK modulation. Since the amplitude of the correlation coefficient can be proportional to the position or delay of the reflected encoded signal, the amplitude variation of the correlation coefficient can be used to provide vital signs which can be used for information diversity or confirmation when obtaining vital signs from the baseband Doppler signal One embodiment of a respiration rate spot checker is illustrated in FIG. 18. The system includes a radar-based physiological sensor 1801 similar to the various embodiments described above, a computational unit, and a display unit. In various embodiments, the computational unit and the display unit can be housed together in single housing 1802 (e.g., a laptop, a handheld computer, a PDA, etc.). The sensor 1801 can communicate with the computation unit and/or the display unit wirelessly or over a wired connection using the various communication protocols discussed above. In various embodiments, the sensor 1801, the computation unit and the display unit can be housed together in a single housing. In certain embodiments, the sensor 1801 and the computational unit can be housed together in single unit and the display unit can be separate.

In various embodiments, after the signal is sampled by the analog to digital converter (ADC), it can transmitted over a wired or wireless communication link (e.g., Bluetooth, USB, etc.) to one or more processors that performs signal processing.

In some embodiments, the radar sensor can include multiple antennas, each with a receiver, such that it can determine the direction of a signal source. In some embodiments, this can be used to determine the direction of the target and to provide feedback to the user on how to better aim the device toward the target. In some embodiments, this multiple-receiver sensor can be used in conjunction with a radio-frequency tag, such that the sensor can determine the direction of the tag and provide feedback to the user on how to better aim the device toward the tag. In some embodiments, a multiple antenna sensor used in conjunction with a radio frequency tag can differentiate or separate the desired target's signal from interference with a software defined smart antenna technique.

In some embodiments, the tag can be constructed using a commercially available Bluetooth module for the tag and the reader. A liquid resistant housing can be designed to encase the Bluetooth module, coin cell battery, voltage upconverter/regulator, LED indicator, an activation circuit, or any combination thereof. The housing can have a slot on either side of the tag so that the housing can be securely clipped to the patient's clothing or worn with a wrist strap. In some embodiments, the activation circuit can preserve the coin cell battery until the tag is activated by pressing a water resistant, indented button, for example, with a pen tip. In some embodiments, the tag can also have a single, 3 color LED that flashes blue when it has a Bluetooth connection, flashes green every 10 seconds when the tag is activated and flashes red every 10 seconds when the battery is low.

VII. Terminology

Conditional language used herein, such as, among others, "can," "could," "might," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm operations described in connection with the embodiments disclosed herein can be implemented as electronic hardware, computer software, firmware, or combinations of the same. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the same. A software module can reside in RAM memory, flash memory, ROM memory, EPROM memory, EEPROM memory, registers, a hard disk, a removable disk, a CD-ROM, or any other form of computer-readable storage medium known in the art. An illustrative storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope. Although certain embodiments and examples are disclosed above, inventive subject matter extends beyond the specifically disclosed embodiments to other alternative embodiments and/or uses and to modifications and equivalents thereof. Thus, the scope of the claims appended hereto is not limited by any of the particular embodiments described. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures, systems, and/or devices described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein. Thus, the invention is limited only by the claims that follow.

The invention claimed is:

1. A method for monitoring of one or more physiological parameters of a subject, the method comprising:
sensing motion of a subject with motion sensing apparatus having different radar views of the subject, wherein sensing motion of the subject comprises: transmitting, with one or more transmitters, radio frequency electromagnetic radiation towards the subject, and receiving, with one or more receivers, reflected radio frequency electromagnetic radiation scattered least by the subject;
compensating for the different radar views of the subject using a weight factor and motion signals from the motion sensing apparatus;
processing of motion signals from the motion sensing apparatus to cancel a sway motion of the subject;
deriving one or more physiological parameters of the subject from the processed motion signals; and
generating output with an output system based on the one or more physiological parameters.

2. The method of claim 1, wherein the processing comprises combining motion signals from a plurality of sensors of the motion sensing apparatus.

3. The method of claim 2, wherein the combining comprises adding the motion signals.

4. The method of claim 3, wherein the motion sensing apparatus detects sway motion of the subject at a first location with a first sensor, and detects sway motion of a patient at second location with a second sensor, wherein the second sensor is spaced apart from the first sensor.

5. The method of claim 4, wherein the first sensor and second sensor are positioned at opposing sides of the subject.

6. The method of claim 4, wherein the first sensor and second sensor are oriented at an angle with respect to the subject, the angle being between about 100 and 260 degrees.

7. The method of claim 6, wherein the angle is between about 150 and 210 degrees.

8. The method of claim 1, wherein the processing comprises:
receiving signals generated by two or more sensors including at least a first sensor and a second sensor, wherein the received signals include at least one of demodulated signals and signals associated with an I path and a Q path; and
performing a linear combination of the received signals such that signal power associated with the received signals is substantially minimized.

9. The method of claim 8, wherein performing the linear combination comprises calculating the linear combination with an adaptive filter.

10. The method of claim 9, wherein the adaptive filter comprises a least mean squares process.

11. The method of claim 10, further comprising rotating signals of the I path and Q path in a plane with a radii by projecting the signals on a line or arc.

12. The method of claim 1, further comprising generating a sway signal representative of the sway motion of the subject.

13. The method of claim 12, performing a principal component analysis on the motion signals.

14. The method of claim 13, further comprising performing another principal component analysis on a result of the principal component analysis.

15. The method of claim 14, further comprising determining one of a physiological signal and a sway signal by selecting an output of the another principal component analysis based on a comparison of eigen values.

16. The method of claim 15, wherein the physiological signal is determined by a smaller eigen value of the eigen values.

17. The method of claim 15, wherein the sway signal is determined by a larger eigen value of the eigen values.

18. The method of claim 15, wherein the physiological signal is a respiratory signal.

19. The method of claim 1, wherein the weight factor is derived according to the expression: $Ae^{j\theta}$
where A represents power and $\theta$ represents phase.

20. The method of claim 1, further comprising computing empirical mode decomposition on the motion signals to separate a respiratory signal from a swaying signal.

21. The method of claim 1, further comprising determining sway of the subject using any of a load cell, an optical sensor, a laser and an ultrasound sensor.

22. The method of claim 1, wherein the one more physiological parameters comprises any of a respiratory parameter and a cardiac parameter.

23. The method of claim 1, wherein the one more physiological parameters comprises a respiratory parameter, the method further comprising detecting an apnea based on the respiratory parameter.

24. The method of claim 1, wherein the output system comprises one or more of a display, an audible system or an external medical system.

25. A system for monitoring of one or more physiological parameters of a subject, the system comprising:
motion sensor apparatus configured to sense motion of a subject and having different radar views of the subject; wherein the motion sensor apparatus is configured to sense motion of the subject by: transmitting, with one or more transmitters, radio frequency electromagnetic radiation towards the subject, and receiving, with one or more receivers, reflected radio frequency electromagnetic radiation scattered least by the subject an output system; and
a processor, the processor in electrical communication with the motion sensor apparatus and the output system, the processor configured to:
process motion signals from the motion sensing apparatus to cancel a sway motion of the subject;
use a weight factor and the motion signals to compensate for the different radar views of the subject;
derive one or more physiological parameters of the subject from the processed motion signals; and
generate output with an output system based on the one or more physiological parameters.

26. The system of claim 25, wherein the processor is configured to process the motion signals to cancel the sway motion by combining motion signals from a plurality of sensors of the motion sensing apparatus.

27. The system of claim 26, wherein the combining adds the motion signals.

28. The system of claim 27, wherein the motion sensor apparatus is configured to detect sway motion of the subject at a first location with a first sensor, and to detect sway motion of a patient at second location with a second sensor, wherein the second sensor is spaced apart from the first sensor.

29. The system of claim 28, wherein the first sensor and second sensor are positioned at opposing sides of the subject.

30. The system of claim 28, wherein the first sensor and second sensor are oriented at an angle with respect to the subject, the angle being between about 100 and 260 degrees.

31. The system of claim 30, wherein the angle is between about 150 and 210 degrees.

32. The system of claim 25, wherein to cancel the sway motion the processor is configured to:
receive signals generated by two or more sensors including at least a first sensor and a second sensor, wherein the received signals include at least one of demodulated signals and signals associated with an I path and a Q path; and
perform a linear combination of the received signals such that signal power associated with the received signals is substantially minimized.

33. The system of claim 32, wherein, to perform the linear combination, the processor is configured to calculate the linear combination with an adaptive filter.

34. The system of claim 33, wherein the adaptive filter comprises a least mean squares process.

35. The system of claim 34 wherein the processor is further configured to rotate signals of the I path and Q path in a plane with a radii by projecting the signals on a line or arc.

36. The system of claim 25, wherein the processor is further configured to generate a sway signal representative of the sway motion of the subject.

37. The system of claim 36, wherein the processor is further configured to perform a principal component analysis on the motion signals.

38. The system of claim 37, wherein the processor is further configured to perform another principal component analysis on a result of the principal component analysis.

39. The system of claim 38, wherein the processor is further configured to determine one of a physiological signal and a sway signal by selecting an output of the another principal component analysis based on a comparison of eigen values.

40. The system of claim 39, wherein the physiological signal is determined by a smaller eigen value of the eigen values.

41. The system of claim 39, wherein the sway signal is determined by a larger eigen value of the eigen values.

42. The system of claim 25, wherein the physiological signal is a respiratory signal.

43. The system of claim 25, wherein the weight factor is derived according to the expression: $Ae_{j\theta}$ where A represents power and $\theta$ represents phase.

44. The system of claim 25, wherein the processor is further configured to perform empirical mode decomposition on the motion signals to separate a respiratory signal from a swaying signal.

45. The system of claim 25, wherein the processor is further configured to determine sway of the subject using a signal from any of a load cell, an optical sensor, a laser and an ultrasound sensor.

46. The system of claim 25, wherein the one more physiological parameters comprises any of a respiratory parameter and a cardiac parameter.

47. The system of claim 25, wherein the one more physiological parameters comprises a respiratory parameter, and wherein the processor is further configured to detect an apnea based on the respiratory parameter.

48. The system of claim 25, wherein the output system comprises one or more of a display, an audible system or an external medical system.

* * * * *